(12) United States Patent
Jones et al.

(10) Patent No.: US 7,618,801 B2
(45) Date of Patent: Nov. 17, 2009

(54) STREPTOMYCES PROTEASE

(75) Inventors: Brian E. Jones, Leiden (NL); Marc Kolkman, Leiden (NL); Chris Leeflang, Leiden (NL)

(73) Assignee: Danison US Inc., Palo Alto, CA (US)

( * ) Notice: Subject to any disclaimer, the term of this patent is extended or adjusted under 35 U.S.C. 154(b) by 117 days.

(21) Appl. No.: 11/929,817

(22) Filed: Oct. 30, 2007

(65) Prior Publication Data

US 2009/0111161 A1 Apr. 30, 2009

(51) Int. Cl.
*C12N 9/48* (2006.01)
(52) U.S. Cl. ...................................... 435/212
(58) Field of Classification Search ........................ None
See application file for complete search history.

(56) References Cited

U.S. PATENT DOCUMENTS

| | | | |
|---|---|---|---|
| 3,840,433 A | 10/1974 | Aunstrup et al. |
| 3,986,926 A | 10/1976 | Monsheimer et al. |
| 4,435,307 A | 3/1984 | Barbesgaard et al. |
| 4,533,359 A | 8/1985 | Kondo et al. |
| 5,147,642 A | 9/1992 | Lotz et al. |
| 5,264,366 A | 11/1993 | Ferrari et al. |
| RE34,606 E | 5/1994 | Estell et al. |
| 5,314,692 A | 5/1994 | Haarasilta et al. |
| 5,340,735 A | 8/1994 | Christianson et al. |
| 5,364,770 A | 11/1994 | Berka et al. |
| 5,500,364 A | 3/1996 | Christianson et al. |
| 5,612,055 A | 3/1997 | Bedford et al. |
| 5,646,028 A | 7/1997 | Leigh |
| 5,646,101 A | 7/1997 | MacBeath |
| 5,686,014 A | 11/1997 | Baillely et al. |
| 5,695,679 A | 12/1997 | Christie et al. |
| 5,698,504 A | 12/1997 | Christie et al. |
| 5,700,676 A | 12/1997 | Bott et al. |
| 5,705,464 A | 1/1998 | Scheper et al. |
| 5,710,115 A | 1/1998 | Patel et al. |
| 5,795,764 A | 8/1998 | Christgau et al. |
| 5,801,039 A | 9/1998 | Maurer et al. |
| 5,855,625 A | 1/1999 | Maurer et al. |
| 5,874,276 A | 2/1999 | Fowler et al. |
| 5,955,340 A | 9/1999 | Bott et al. |
| 5,965,384 A | 10/1999 | Boel et al. |
| 6,132,970 A | 10/2000 | Stemmer |
| 6,287,839 B1 | 9/2001 | Jones et al. |
| 6,312,936 B1 | 11/2001 | Poulose et al. |
| 6,376,450 B1 | 4/2002 | Ghosh et al. |
| 6,440,991 B1 | 8/2002 | Zhu et al. |
| 6,465,235 B1 | 10/2002 | Bott et al. |
| 6,482,628 B1 | 11/2002 | Poulose et al. |
| 6,566,114 B1 | 5/2003 | Kauppinen et al. |
| 6,602,842 B2 | 8/2003 | Cuperus et al. |
| 6,605,458 B1 | 8/2003 | Hansen et al. |
| 6,610,642 B2 | 8/2003 | Ghosh et al. |

FOREIGN PATENT DOCUMENTS

| | | |
|---|---|---|
| DE | 43 32 692 C1 | 7/1994 |
| EP | 0 134 267 A1 | 3/1985 |
| EP | 0 214 761 A2 | 3/1987 |
| EP | 0 218 272 A1 | 4/1987 |
| EP | 0 238 023 A2 | 9/1987 |
| EP | 0 258 068 A2 | 3/1988 |
| EP | 0 305 216 A1 | 3/1989 |
| EP | 0 331 376 A2 | 9/1989 |
| EP | 0 495 257 A1 | 7/1992 |
| EP | 0 505 920 A1 | 9/1992 |
| GB | 1296839 A | 11/1972 |
| GB | 1372034 A | 10/1974 |
| GB | 2233665 A | 1/1991 |
| GB | 2250289 A | 6/1992 |
| GB | 1493807 A | 1/2005 |
| JP | 64-074992 A | 3/1989 |
| JP | 04-327274 A | 11/1992 |
| WO | WO 88/09367 A1 | 12/1988 |
| WO | WO 89/06270 A1 | 7/1989 |
| WO | WO 90/09446 A1 | 8/1990 |
| WO | WO 91/16422 A1 | 10/1991 |
| WO | WO 92/05249 A1 | 4/1992 |
| WO | WO 92/21760 A1 | 12/1992 |
| WO | WO 93/10249 A1 | 5/1993 |
| WO | WO 94/12621 A1 | 6/1994 |
| WO | WO 94/18314 A1 | 8/1994 |
| WO | WO 94/25576 A1 | 11/1994 |
| WO | WO 95/00426 A1 | 1/1995 |
| WO | WO 95/23221 A1 | 8/1995 |
| WO | WO 96/05295 A2 | 2/1996 |
| WO | WO 96/10646 A1 | 4/1996 |
| WO | WO 96/11285 A1 | 4/1996 |
| WO | WO 96/34946 A1 | 11/1996 |
| WO | WO 97/07770 A1 | 3/1997 |
| WO | WO 98/07846 A1 | 2/1998 |
| WO | WO 98/22500 A2 | 5/1998 |
| WO | WO 99/20723 A2 | 4/1999 |
| WO | WO 99/34011 A2 | 7/1999 |

(Continued)

OTHER PUBLICATIONS

Rothgeb et al, The raw material, finished products and dust pad analysis of detergent proteases using a small synthetic substrate. Journal of the American Oil Chemists' Society vol. 65, No. 5 / May 1988, p. 806-810.*

(Continued)

*Primary Examiner*—Sheridan Swope

(57) ABSTRACT

Certain aspects of this disclosure relate to an isolated protease, and cleaning compositions containing the same. In some embodiments, the protease may comprise an amino acid sequence that is at least 80% identical to the wild type *Streptomyces* 1AG3 protease. Isolated nucleic acid encoding the subject protease, recombinant nucleic acid containing the same and host cells containing the recombinant nucleic acid are also provided.

13 Claims, 6 Drawing Sheets

FOREIGN PATENT DOCUMENTS

| WO | WO 99/43835 A2 | 9/1999 |
|---|---|---|
| WO | WO 02/50245 A2 | 6/2002 |
| WO | WO 03/000865 A2 | 1/2003 |
| WO | WO 2005/052146 A2 | 6/2005 |
| WO | WO 2005/052161 A2 | 6/2005 |
| WO | WO 2005/095591 A2 | 10/2005 |
| WO | WO 2006/054997 A1 | 5/2006 |

OTHER PUBLICATIONS

U.S. Appl. No. 10/576,331, filed Nov. 19, 2004, Shaw et al.
Altschul, S.F. et al. "Local alignment statistics." *Methods Enzymol* 266: 460-80, 1996.
Altschul, S.F. et al. "Basic local alignment search tool." *J. Mol. Biol* 215(3): 403-410, 1990.
Anonymous. "Enzymatic silk degumming." *Research Disclosure Journal* No. 21634, 1982.
Beaucage, S.L. et al. "Deoxynucleoside phosphoramidites—A new class of key intermediates for deoxypolynucleotide synthesis." *Tetrahedron Lett.* 22(20): 1859-1862, 1981.
Benton, W.D. et al. "Screening λgt recombinant clones by hybridization to single plaques in situ." *Science* 196(4286): 180-182, Apr. 8, 1977.
Binnie, C. et al. "Expression and Characterization of Soluble Human Erythropoietin Receptor Made in Streptomyces lividans 66." *Protein Expression and Purification* 11(3): 271-278, Dec. 1997.
Dartois, V. et al. "Cloning, nucleotide sequence and expression in *Escherichia coli* of a lipase gene from *Bacillus subtilis* 168." *Biochimica et Biophysica Acta* 1131(3): 253-260, Jul. 15, 1992.
Database UniProt. "SubName: Full=Serine protease; Flags: Precursor;" Accession No. Q5K2R6, Feb. 15, 2005.
Dehottay, P. et al. "Nucleotide sequence of the gene encoding the *Streptomyces albus* G β-lactamase precursor." *European Journal of Biochemistry* 166(2): 345-350, 1987.
DelMar, E.G. et al. "A sensitive new substrate for chymotrypsin." *Analytical Biochemistry* 99(2): 316-320, Nov. 1, 1979.
Devereux, P. et al. "A comprehensive set of sequence analysis programs for the VAX." *Nucl. Acids Res* 12: 387-395, 1984.
Dynan, W.S. et al. "Control of eukaryotic messenger RNA synthesis by sequence-specific DNA-binding proteins." *Nature* 316(6031): 774-778, 1985.
Feng, D.F. et al. "Progressive sequence alignment as a prerequisite to correct phylogenetic trees." *J. Mol. Evol* 25(4): 351-360, 1987.
Fernandez-Abalos, J.M. et al. "Posttranslational processing of the xylanase Xys1L from *Streptomyces halstedii* JM8 is carried out by secreted serine proteases." *Microbiology* 149(7): 1623-1632, Jul. 1, 2003.
Ferrari, E. et al. "Genetics." in *Bacillus*, edited by C.R. Harwood, pp. 57-72. Biotechnology Handbooks 2. New York: Plenum Press, 1989.
Fornwald, J.A. et al. "Two promoters, one inducible and one constitutive, control transcription of the *Streptomyces lividans* galactose operon." *Proc. Natl. Acad. Sci. U.S.A* 84(8): 2130-4, Apr. 1987.
Grunstein, M. et al. "Colony Hybridization: A Method for the Isolation of Cloned DNAs that Contain a Specific Gene." *Proc. Natl. Acad. Sci. U.S.A* 72(10): 3961-3965, Oct. 1975.
Guérout-Fleury, A.-M. et al. "Antibiotic-resistance cassettes for *Bacillus subtilis*." *Gene* 167(1-2): 335-336, Dec. 29, 1995.
Haas, M.J. et al. "Cloning, expression and characterization of a cDNA encoding a lipase from *Rhizopus delemar.*" *Gene* 109(1): 107-113, Dec. 20, 1991.
Henikoff, S. et al. "Amino Acid Substitution Matrices from Protein Blocks." *Proc. Natl. Acad. Sci. USA* 89: 10915-10919, 1992.
Higgins, D.G. et al. "Fast and sensitive multiple alignment sequence on a microcomputer." *CABIOS* 5: 151-153, 1989.

Hopwood, D.A. et al. "Regulation of gene expression in antibiotic-producing *Streptomyces*." in *Regulation of gene expression—25 years on*, edited by I.R. Booth et al., pp. 251-276. Cambridge, England: Cambridge UP, 1986.
Karlin, S. et al. "Applications and statistics for multiple high-scoring segments in molecular sequences." *Proc. Natl. Acad. Sci. USA* 90(12): 5873-7, Jun. 15, 1993.
Kraut, J. "Serine Proteases: Structure and Mechanism of Catalysis." *Annual Review of Biochemistry* 46(1): 331-358, 1977.
Kugimiya, W. et al. "Cloning and sequence analysis of cDNA encoding *Rhizopus niveus* lipase." *Bioscience, Biotechnology, and Biochemistry* 56(5): 716-9, May 1992.
Li, Jiang et al. "Functional expression of the keratinolytic serine protease gene sfp2 from *Streptomyces fradiae* var. k11 in *Pichia pastoris.*" *Protein Expression and Purification* 54(1): 79-86, Jul. 1, 2007.
Matthes H.W.D. et al. "Simultaneous rapid chemical synthesis of over one hundred oligonucleotides on a microscale." *EMBO J.* 3(4): 801-805, Apr. 1984.
Motamedi, H. et al. "Integrative vectors for heterologous gene expression in *Streptomyces*spp.." *Gene* 160(1): 25-31, Jul. 4, 1995.
Nakamura, Y. et al. "Codon usage tabulated from international DNA sequence databases: status for the year 2000." *Nucl. Acids Res.* 28(1): 292, Jan. 1, 2000.
Needham-VanDevanter, D.R. et al. "Characterization of an adduct between CC-1065 and a defined oligodeoxynucleotide duplex." *Nucleic Acids Research* 12(15): 6159-6168, Aug. 10, 1984.
Needleman, S.B. et al. "A general method applicable to the search for similarities in the amino acid sequence of two proteins." *J. Mol. Biol* 48(3): 443-53, Mar. 1970.
Olmos-Soto, J. et al. "Genetic system constructed to overproduce and secrete proinsulin in *Bacillus subtilis*." *Appl. Microbiol. Biotechnol.* 62(4): 369-373, 2003.
Pagé, N. et al. "Increased xylanase yield in *Streptomyces lividans*: Dependence on number of ribosome-binding sites." *Nat Biotech* 14(6): 756-759, Jun. 1996.
Palmeros, B. et al. "A family of removable cassettes designed to obtain antibiotic-resistance-free genomic modifications of *Escherichia coli* and other bacteria." *Gene* 247(1-2): 255-264, Apr. 18, 2000.
Pearson, W.R. et al. "Improved Tools for Biological Sequence Comparison." *Proc. Natl. Acad. Sci. USA* 85(8): 2444-2448, Apr. 15, 1988.
Pulido, D. et al. "A *Bacillus subtilis* phage φ29 transcription terminator is efficiently recognized in *Streptomyces ividans.*" *Gene* 56(2-3): 277-282, 1987.
Schmitt-John, T. et al. "Promoter constructions for efficient secretion expression in *Streptomyces lividans.*" *Appl. Microbiol. Biotechnol.* 36(4): 493-498, Jan. 1, 1992.
Shimada, Y. et al. "cDNA Molecular Cloning of Geotrichum candidum Lipase." *J Biochem* 106(3): 383-388, Sep. 1, 1989.
Simonen, M. et al. "Protein secretion in *Bacillus* species." *Microbiol. Rev.* 57(1): 109-137, 1993.
Smith, T.F. et al. "Comparison of biosequences." *Adv. Appl. Math* 2: 482-489, 1981.
Taguchi, S. et al. "Analysis of transcriptional control regions in the *Streptomyces* subtilisin-inhibitor-encoding gene." *Gene* 84(2): 279-86, Dec. 14, 1989.
Trieu-Cuot, P. et al. "Nucleotide sequence of the *Streptococcus faecalis*plasmid gene encoding the 3'5"-aminoglycoside phosphotransferase type III." *Gene* 23(3): 331-41, Sep. 1983.
Yamaguchi, S. et al. "Cloning and structure of the mono- and diacylglycerol lipase-encoding gene from *Penicillium camembertii* U-150." *Gene* 103(1): 61-7, Jul. 15, 1991.
PCT International Search Report for Int'l Appln No. PCT/US2008/081088, filing date of Oct. 24, 2008.

* cited by examiner

FIGURE 2.

```
1AG3 protease    (1)   -----MHRRRGALFAGAVAIAALTIAAAPATAGPALAPPPAQETAAQEIP
StreptogrisinC   (1)   VERTTLRRRALVAGTATVAVGALALAGLTGVASADPAATAAPPVSADSLS 1AG3 protease   (46)   AGMLQAMQRDLGLTEQQAEERVANEYQAGQLEPRLRAQIADTFAGSWTRG
StreptogrisinC  (51)   PGMLAALERDLGLDEDAARSRIANEYRAAAVAAGLEKSLGARYAGARVSG 1AG3 protease   (96)   ETAELVVATTDREQLPALTAAGVRATVAEHSLSELEAVKETLDEAAEEHA
StreptogrisinC (101)   AKATLTVATTDASEAARITEAGARAEVVGHSLDRFEGVKKSLDKAALDKA 1AG3 protease  (146)   TTEAPVWYVDVTSNTVIVHAQDVTAGRDFVSAAGVDPAAVHVLRSDEQPR
StreptogrisinC (151)   PKNVPVWYVYDVAANRVVVNAASPAAGQAFLKVAGVDRGLVTVARSAEQPR 1AG3 protease  (196)   PYHDLRGGEAYYMGSGGRCSVGFSVRRGTQAGFATAGHCGRVGTTTRGFN
StreptogrisinC (201)   ALADIRGGDAYYMNGSGRCSVGFSVTRGTQNGFATAGHCGRVGTTTNGVN 1AG3 protease  (246)   QVAGGFFQGSIFPGRDMGWVAVNSMWNTTPFVRGQGGANVTVAGSQQAPV
StreptogrisinC (251)   QQAQGTFQGSTFPGRDIAWVATNANWTPRPLVNGYGRGDVTVAGSTASVV 1AG3 protease  (296)   GSSVCRSGSTTGWHCGTIQQHNTSVRVPECTISGVTRTSVCAEPGDSGGA
StreptogrisinC (301)   GASVCRSGSTTGWHCGTIQQLNTSVTYPEGTISGVTRTSVCAEPGDSGGS 1AG3 protease  (346)   YISGNQAQGVTSGGSGNCRTGGTTYHQPINPLLAQWNLTLVTTCNGGDPG
StreptogrisinC (351)   YISGSQAQGVTSGGSGNCSSGGTTYFQPINPLLQAYGLTLVTSG-GGTPT 1AG3 protease  (396)   DPGDPGDPGEPGGSWSAGTSYAVGDRVTYGGAEYRCLQAHVAQSGWTPPN
StreptogrisinC (400)   DPPTTPPTDSPGGTWAVGTAYAAGATVTYGGATYRCLQAHTAQPGWTPAD 1AG3 protease  (446)   TPALWQRV
StreptogrisinC (450)   VPALWQRV
```

FIGURE 3.

```
1AG3 protease mature  (1)   HDLRGGEAYYMGSGGRCSVGFSVRRGTQAGFATAGHCGRVGTTTR
StreptogrisinC mature (1)   ADIRGGDAYYMNGSGRCSVGFSVTRGTQNGFATAGHCGRVGTTTN 1AG3 protease mature  (46)  GFNQVAQGTFQGSIFPGRDMGWVAVNSNWNTTPFVRGQGGANVTV
StreptogrisinC mature (46)  GVNQQAQGTFQGSTFPGRDIAWVATNANWTPRPLVNGYGRGDVTV 1AG3 protease mature  (91)  AGSQQAPVGSSVCRSGSTTGWHCGTIQQHNTSVRYPEGTISGVTR
StreptogrisinC mature (91)  AGSTASVVGASVCRSGSTTGWHCGTIQQLNTSVTYPEGTISGVTR 1AG3 protease mature  (136) TSVCAEPGDSGGAYISGNQAQGVTSGGSGNCRTGGTTYHQPINPL
StreptogrisinC mature (136) TSVCAEPGDSGGSYISGSQAQGVTSGGSGNCSSGGTTYFQPINPL 1AG3 protease mature  (181) LAQWNLTLVTTGNGGDPGDPGDPGEPGGSWSAGTSYAVGDRV
StreptogrisinCmature  (181) LQAYGLTLVTSG..GGTPTDPPTTPPTDSPGCTWAVCTAYAAGATV 1AG3 protease mature  (226) TYGGAEYRCLQAHVAQSGWTPPNTPALWQRV
StreptogrisinC mature (225) TYGGATYRCLQAHTAQPGWTPADVPALWQRV
```

FIGURE 4.

```
Asp            (1)  -MTPRTVTRALAVATAAATLLAGGMAAQANEPAPPGSASAPPRLAEKLDP
1AG3 protease  (1)  MHRRRGALFAGAVAIAALTIAAAPATAGPALAPPP----AQETAAQEIPA Asp           (50)  DLLEAMERDLGLDAEEAAATLAFQHDAETGEALAEELDEDFAGTWEDD
1AG3 protease (47)  GMLQAMQRDLGLTEQQAEERVANEYQAGQLEPRLRAQLADTFAGSWTRGE Asp          (100)  --VLYVATTDEDAVEEVEGEGATAVTVEHSLADLEAWKTVLDAALEGHD-
1AG3 protease (97)  TAELVVATTDREQLPALTAAGVRATVAEHSLSELEAVKETLDEAAEEHAT Asp          (147)  -DVPTWYVDVPTNSVVVAVKAGAQDVAAG--LVEGADVPSDAVTFVETDE
1AG3 protease(147)  TEAPVWYVDVTSN----TVIVHAQDVTAGRDFVSAAGVDPAAVHVLRSDE Asp          (194)  TPRTMFDVIGGNAYTIGGRSRCSIGFAVN----GGFITAGHCGRTGAFTA
1AG3 protease(193)  QPRPYHDLRGGEAYYMGSGGRCSVGFSVRRGTQAGFATAGHCGRVGTTTR Asp          (240)  NP-----TGTFAGSSFPGNDYAFVRTGAGVNLLAQVNNYSCGRVQVAGHTA
1AG3 protease(243)  GFNQVAQGTFQGSIFPGRDMGWVAVNSNWNTTPFVRGQGGANVTVAGSQQ Asp          (286)  APVGSAVCRSGSTTGWHCGTITALNSSVTYPEGTVRGLIRTTVCAEPGDS
1AG3 protease(293)  APVGSSVCRSGSTTCWHCCTIQQHNTSVRYPEGTISGVTRTSVCAEPGDS Asp          (336)  GGSLLAGNQAQGVTSGGSGNCRTGGTTFFQPVNPILQAYGLRMITTDSGS
1AG3 protease(343)  GGAYISGNQAQGVTSGGSGNCRTGGTTYHQPINPLLAQWNLTLVTTGNGG Asp          (386)  SPAPAPTSCTGYARTFTGTLAAGRAAAQPNGSYVQVNRSGTHSVCLNGPS
1AG3 protease(393)  --DPGDPGDPGDPGEPGGSWSAGTSYAVG----DRVTYGGAEYRCLQAH- Asp          (436)  GADFDLYVQRWNGSSWVTVAQSTPGSSNETTTYRGNAGYYRYVVNAASGS
1AG3 protease(436)  ------------------VAQSGWTPPNTPALMQRV--------------

Asp          (486)  GAYTMGLTLP
1AG3 protease(454)  ----------
```

FIGURE 5.

```
ASP-mature   (1)  FDVIGGNAYTIGGRSRCSIGFAVN----GGFTTAGHCGRTGATTANP---
1AG3 mature  (1)  HDLRGGEAYYMGSGGRCSVGFSVRRGTQAGFATAGHCGRVGTTTRGFNQV ASP-mature  (44)  -TGTFAGSSFPGNDYAFVRTGAGVNLLAQVNNYSGGRVQVAGHTAAPVGS
1AG3mature  (51)  AQGTFQGSIFPGRDMGWVAVNSNWNTPFVRGQGGANVTVAGSQQAPVGS ASP-mature  (93)  AVCRSGSTTGWHCGTTITALNSSVTYPEGTVRGLIRTTVCAEPGDSGGSLL
1AG3mature (101)  SVCRSGSTTGWHCGTIQQHNTSVRYPEGTISGVTRTSVCAEPGDSCGAYI ASP-mature (143)  AGNQAQGVTSGGSGNCRTGGTTFFQPVNPILQAYGLRMITTDSGSSP---
1AG3mature (151)  SGNQAQGVTSGGSGNCRTGGTTYHQPINPLLAQWNLTLVTTGNGGDPGDP ASP-mature (190)  -------------------------------------------------
1AG3mature (201)  GDPGDPGEPGGSWSAGTSYAVGDRVTYGGAEYRCLQAHVAQSGWTPPNTP ASP-mature (190)  ------
1AG3mature (251)  ALWQRV
```

STREPTOMYCES PROTEASE

BACKGROUND

Serine proteases are a subgroup of a diverse class of enzymes having a wide range of specificities and biological functions. Despite their functional diversity, the catalytic machinery of serine proteases has been investigated in at least two genetically distinct families of enzymes, namely the subtilisins and the mammalian chymotrypsin-related and homologous bacterial serine proteases (e.g., trypsin and S. griseus trypsin). These two families of serine proteases show remarkably similar mechanisms of catalysis (See e.g., Kraut, Ann. Rev. Biochem., 46:331-358 [1977]). Furthermore, although the primary structure is unrelated, the tertiary structure of these two enzyme families brings together a conserved catalytic triad of amino acids. The subtilisins and chymotrypsin-related serine proteases both have a catalytic triad comprising aspartate, histidine and serine. In the subtilisin-related proteases the relative order of these amino acids, reading from the amino to carboxy terminus, is aspartate-histidine-serine. However, in the chymotrypsin-related proteases, the relative order is histidine-aspartate-serine. Much research has been conducted on the subtilisins, due largely to their usefulness in cleaning and feed applications. Additional work has been focused on the adverse environmental conditions (e.g., exposure to oxidative agents, chelating agents, and/or extremes of temperature and/or pH) which can adversely impact the functionality of these enzymes in various applications. Nonetheless, there remains a need in the art for enzyme systems that are able to resist these adverse conditions and retain or have improved activity over those currently known in the art.

SUMMARY OF THE INVENTION

An isolated serine protease is provided, as well as cleaning compositions containing the same. In general terms, the protease may be identical to or a variant of the wild type *Streptomyces* 1AG3 protease (SEQ ID NO:9). In some embodiments, the protease may comprise an amino acid sequence that is at least 80% identical to the wild type *Streptomyces* 1AG3 protease. In particular embodiments, the isolated serine protease may have at least one amino acid substitution relative to the wild type *Streptomyces* 1AG3 protease. In these embodiments, the isolated serine protease may have an altered substrate specificity relative to the wild-type *Streptomyces* 1AG3 protease and may have an altered pI, an improved activity such as improved acid stability, thermostability, casein hydrolysis, keratin hydrolysis, cleaning performance, and/or LAS stability, relative to the wild type *Streptomyces* 1AG3 protease.

Also provided is an isolated nucleic acid encoding the isolated serine protease. In these embodiments, the isolated nucleic acid may have a nucleotide sequence that: a) hybridizes to SEQ ID NO:8 under stringent hybridization conditions; and/or b) is at least 70% identical to SEQ ID NO:8.

A recombinant polynucleotide comprising the isolated nucleic acid is also provided. In certain embodiments, the recombinant polynucleotide may comprise, in operable linkage, a promoter and the isolated nucleic acid. The promoter may be heterologous to the isolated nucleic acid in that it is not the wild type *Streptomyces* 1AG3 protease promoter. In certain cases, the promoter may be the wild type *Streptomyces* 1AG3 protease promoter. The recombinant nucleic acid may provide for secretion of the isolated serine protease from a host cell, i.e., may contain a signal sequence-encoding region that targets the isolated serine protease for secretion. An expression vector comprising the recombinant nucleic acid is also provided.

Also provided is a host cell comprising the recombinant polynucleotide. In certain cases, the host cell is selected from *Bacillus* sp., *Streptomyces* sp., *Aspergillus* sp., and *Trichoderma* sp. The recombinant polynucleotide may be present in an expression vector in the cell, or may be present in the genome of the cell (i.e., integrated into the genome of the host cell). The host cell may be employed in a method of producing an isolated serine protease. In certain embodiments, this method may comprise: culturing the host cell under conditions suitable for the production of the isolated serine protease. The method may further comprise comprising recovering said isolated serine protease. In certain cases, the protease may be secreted into the culture medium and the method may comprise recovering the protease from the culture medium.

A cleaning composition comprising the isolated serine protease is also provided. In certain embodiments, the cleaning composition may further comprise a surfactant, which in certain cases may be a sodium alkyl sulfate surfactant that comprises an ethylene oxide moiety. The cleaning composition may contain from about 0.001% to about 0.5% by weight of the isolated serine protease. In certain embodiments, the cleaning composition comprises a sufficient amount of a pH modifier to provide said composition with a neat pH of from about 3 to about 5, where the cleaning composition is essentially free of materials that hydrolyze at a pH of from about 3 to about 5. The cleaning composition may be formulated as a laundry detergent, or as a dishwashing detergent, for example. In addition to the subject protease, the cleaning composition may also comprise an additional enzyme selected from a protease, an amylase, a lipase, a mannanase, a pectinase, a cutinase, a oxidoreductase, a hemicellulase, or a cellulase. In certain embodiments, the cleaning composition may further comprise a stabilizing agent which, in certain cases, may be selected from the group consisting of borax, glycerol, and a competitive inhibitor. The stabilizing agent may stabilize the isolated serine protease to anionic surfactants. The cleaning composition may be a solid or liquid composition.

The cleaning composition may be employed in a cleaning method. In general terms, this method comprises: a) contacting an object with the cleaning composition to clean the object. In certain cases, the method may further include washing and/or rinsing the object. In exemplary embodiments, the object may be a fabric (e.g., clothing), or an item of dishware (e.g., a dish).

Also provided is animal feed comprising the isolated serine protease.

DESCRIPTION OF THE FIGURES

FIG. 2 provides an alignment of polypeptide sequences from 1AG3 (SEQ ID NO:2) and Streptogrisin C (SEQ ID NO:23).

FIG. 3 provides an alignment of the mature (i.e., catalytic domains) of 1AG3 protease (SEQ ID NO:9) and Streptogrisin C (SEQ ID NO:24). In this Figure, the active site amino acids (his-asp-ser) are printed in bold and the characteristic three disulfide bridges are indicated by connecting lines.

FIG. 4 provides an alignment of 1AG3 protease (SEQ ID NO:2) and ASP (SEQ ID NO:25).

FIG. 5 provides an alignment of the mature (i.e., catalytic domains) of 1AG3 protease (SEQ ID NO:9) and ASP (SEQ ID NO:26).

DETAILED DESCRIPTION OF THE INVENTION

Figure 1:
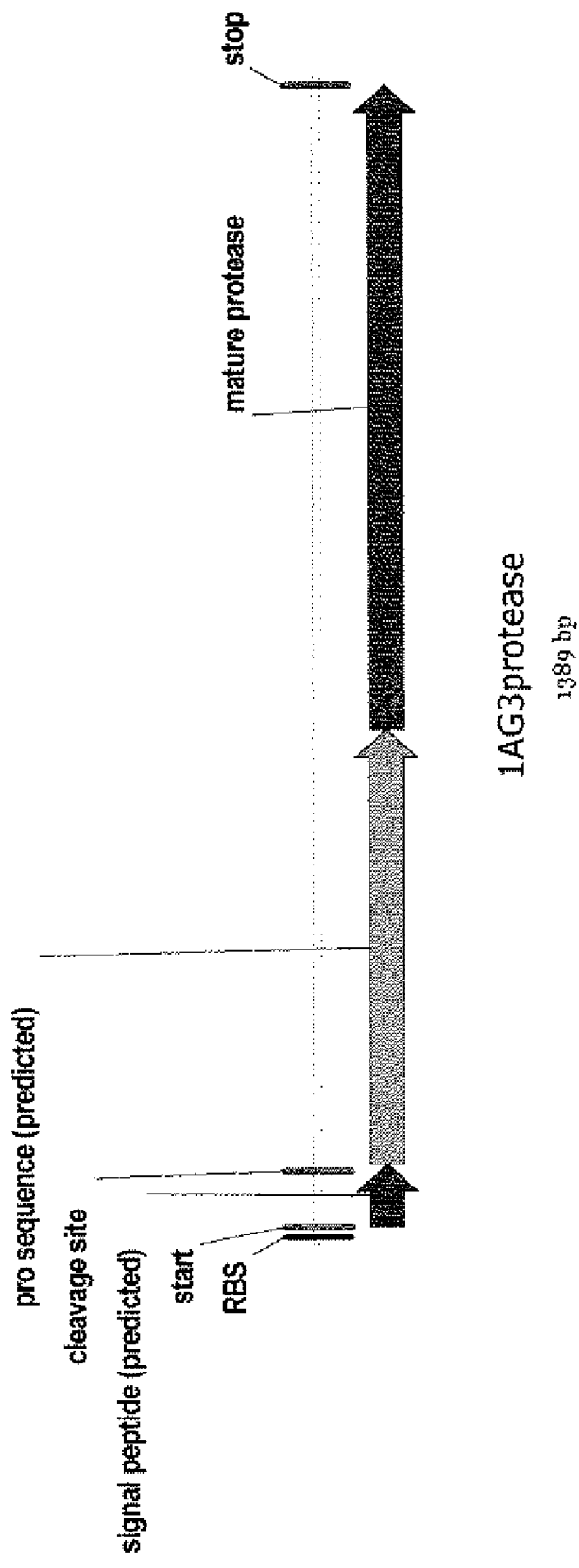
FIG. 1 provides a schematic diagram showing the organization of the 1AG3 gene.
Figure 6:
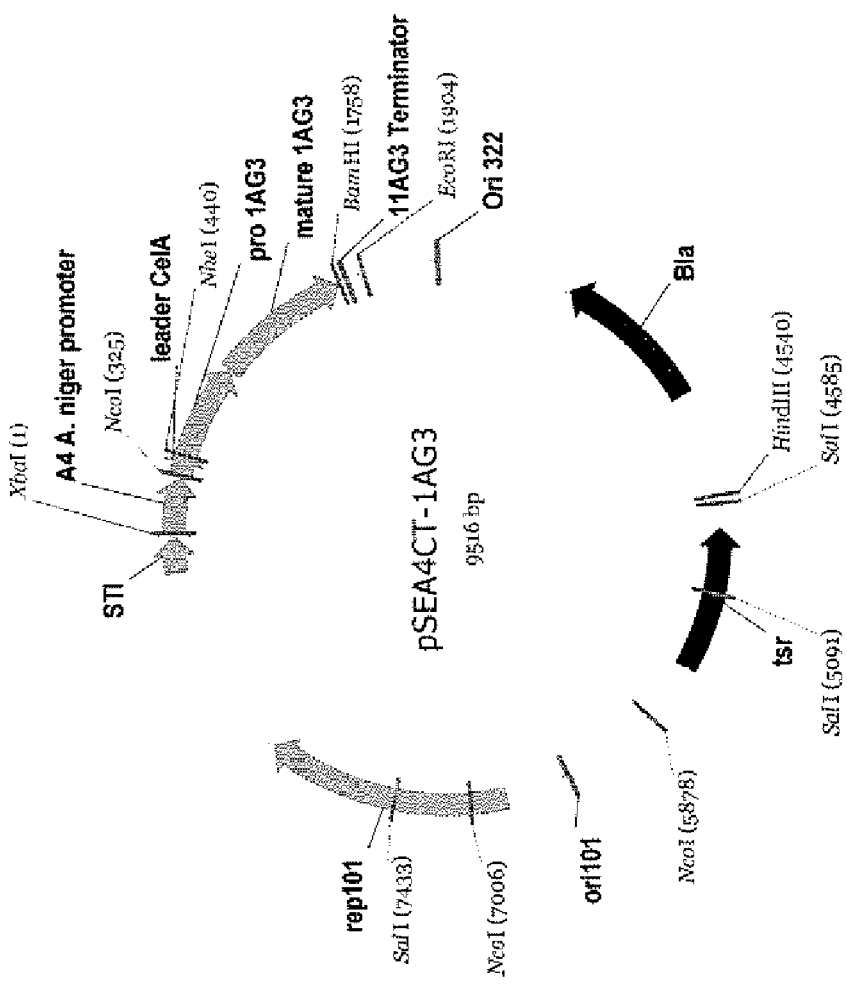
FIG. 6 provides a map of the pSEA4CT-1AG3 expression construct.

Provided herein are novel proteases, novel genetic material encoding these enzymes, and proteolytic proteins obtained from *Streptomyces* species, including variant proteins developed therefrom. In certain embodiments, protease compositions obtained from a newly described *Streptomyces* species, DNA encoding the protease, vectors comprising the DNA encoding the protease, host cells transformed with the vector DNA, and an enzyme produced by the host cells are provided. Certain embodiments of the present invention also provide cleaning compositions (e.g., detergent compositions), animal feed compositions, and textile and leather processing compositions comprising protease(s) obtained from a *Streptomyces* sp. In alternative embodiments, the present invention provides mutant (i.e., variant) proteases derived from the wild-type proteases described herein. These mutant proteases also find use in numerous applications.

*Streptomyces* are Gram-positive bacteria classified as members of the Family Streptomycetaceae, Suborder Streptomycineae, Order Actinomycetales, class Actinobacteria. *Streptomyces* grows as an extensively branching primary or substrate mycelium and an abundant aerial mycelium that at maturity bear characteristic spores. Streptogrisins are serine proteases secreted in large amounts from a wide variety of *Streptomyces* species. The amino acid sequences of *Streptomyces* proteases have been determined from at least 9 different species of *Streptomyces* including *Streptomyces griseus* Streptogrisin C (accession no. P52320); alkaline proteinase (EC 3.4.21.-) from *Streptomyces* sp. (accession no. PC2053); alkaline serine proteinase I from *Streptomyces* sp. (accession no. S34672), serine protease from *Streptomyces lividans* (accession no. CAD4208); putative serine protease from *Streptomyces coelicolor* A3(2) (accession no. NP_625129); putative serine protease from *Streptomyces avermitilis* MA-4680 (accession no. NP_822175); serine protease from *Streptomyces lividans* (accession no. CAD42809); putative serine protease precursor from *Streptomyces coelicolor* A3(2) (accession no. NP_628830)). A purified native alkaline protease having an apparent molecular weight of 19,000 daltons and isolated from *Streptomyces griseus* var. alkaliphilus and cleaning compositions comprised thereof have been described (See e.g., U.S. Pat. No. 5,646,028, incorporated herein by reference). An additional strain was isolated from a sample of lake water and sediment; this strain is designated herein as "strain 1AG3." The temperature of the water column and sediment were 19-23° C., pH 10.5, and the water conductivity was 26.1 mS cm$^1$.

In certain cases, the protease enzymes described herein may have good stability and proteolytic activity. These enzymes find use in various applications, including but not limited to cleaning compositions, animal feed, textile and leather processing, etc. The present invention also provides means to produce these enzymes. In some embodiments, the proteases of the present invention are in pure or relatively pure form.

In certain embodiments, the present invention also provides nucleotide sequences which are suitable to produce the proteases of the present invention in recombinant organisms. In some embodiments, recombinant production provides means to produce the proteases in quantities that are commercially viable.

Unless otherwise indicated, the practice of the present invention involves conventional techniques commonly used in molecular biology, microbiology, and recombinant DNA techniques, which are within the skill of the art. Such techniques are known to those of skill in the art and are described in numerous texts and reference works. All patents, patent applications, articles and publications mentioned herein, both supra and infra, are hereby expressly incorporated herein by reference.

Unless defined otherwise herein, all technical and scientific terms used herein have the same meaning as commonly understood by one of ordinary skill in the art to which this invention pertains. Although any methods and materials similar or equivalent to those described herein find use in the practice of the present invention, exemplary methods and materials are described. Accordingly, the terms defined immediately below are more fully described by reference to the Specification as a whole. Also, as used herein, the singular "a", "an" and "the" includes the plural reference unless the context clearly indicates otherwise. Numeric ranges are inclusive of the numbers defining the range. Unless otherwise indicated, nucleic acid sequences are written left to right in 5' to 3' orientation; amino acid sequences are written left to right in amino to carboxy orientation, respectively. It is to be understood that this invention is not limited to the particular methodology, protocols, and reagents described, as these may vary, depending upon the context they are used by those of skill in the art.

The practice of the present invention employs, unless otherwise indicated, conventional techniques of protein purification, molecular biology, microbiology, recombinant DNA techniques and protein sequencing, all of which are within the skill of those in the art.

Furthermore, the headings provided herein are not limitations of the various aspects or embodiments of the invention which can be had by reference to the specification as a whole. Accordingly, the terms defined immediately below are more fully defined by reference to the specification as a whole. Nonetheless, in order to facilitate understanding of the invention, a number of terms are defined below.

I. Definitions

As used herein, the terms "protease," and "proteolytic activity" refer to a protein or peptide exhibiting the ability to hydrolyze peptides or substrates having peptide linkages. Many well known procedures exist for measuring proteolytic activity and are familiar to those of skill in the art. For example, proteolytic activity may be ascertained by comparative assays which analyze the respective protease's ability to hydrolyze a commercial substrate. Exemplary substrates useful in the analysis of proteases and/or proteolytic activity, include, but are not limited to di-methyl casein (Sigma C-9801), bovine collagen (Sigma C-9879), bovine elastin (Sigma E-1625), and bovine keratin (ICN Biomedical 902111). Colorimetric assays utilizing these substrates are well known in the art (See e.g., WO 99/34011; and U.S. Pat. No. 6,376,450, both of which are incorporated herein by reference. The pNA assay (See e.g., Del Mar et al., Anal. Biochem., 99:316-320 [1979]) also finds use in determining the active enzyme concentration for fractions collected during gradient elution. This assay measures the rate at which p-nitroaniline is released as the enzyme hydrolyzes the soluble synthetic substrate, succinyl-alanine-alanine-proline-phenylalanine-p-nitroanilide (sAAPF-pNA). The rate of production of yellow color from the hydrolysis reaction is measured at 410 nm on a spectrophotometer and is proportional to the active enzyme concentration. In addition, absorbance measurements at 280 nm can be used to determine the total protein concentration. The active enzyme/total-protein ratio gives the enzyme purity.

As used herein, the terms Strain "1AG3 protease" refers to the protease of one embodiment of the present invention. The wild-type protease was isolated from *Streptomyces* strain 1AG3, as described herein. In some embodiments, the present invention provides the active form of the protease comprising a polypeptide of 256 amino acids. In additional embodiments, the 1AG3 protease is a variant or homolog of the 1AG3 ASP protease.

The term "*Streptomyces* protease homologues" refers to naturally occurring proteases having substantially identical amino acid sequences to the mature protease derived from *Streptomyces* strain 1AG3 and/or polynucleotide sequences which encode for such naturally occurring proteases, and which proteases retain the functional characteristics of a serine protease encoded by such nucleic acids.

"ASP protease," "Asp protease," and "Asp," refer to the serine proteases described herein and in PCT Ser. Nos. US04/39006 and US04/39066, all of which are incorporated herein by reference in their entireties. In some embodiments, the Asp protease is the protease designed herein as 69B4 protease obtained from Cellulomonas strain 69B4. Thus, in certain embodiments, the term "69B4 protease" refers to a naturally occurring mature protease derived from Cellulomonas strain 69B4 (DSM 16035) having substantially identical amino acid sequences as provided in SEQ ID NO:25. In some alternative embodiments, the present invention provides portions of the ASP protease.

The term "Cellulomonas protease homologues" refers to naturally occurring proteases having substantially identical amino acid sequences to the mature protease derived from Cellulomonas strain 69B4 or polynucleotide sequences which encode for such naturally occurring proteases, and which proteases retain the functional characteristics of a serine protease encoded by such nucleic acids. In some embodiments, these protease homologues are referred to as "cellulomonadins."

As used herein, the terms "*Streptomyces* 1AG3 variant," "*Streptomyces* protease variant," and "1AG3 protease variant" are used in reference to proteases that are similar to the wild-type *Streptomyces* 1AG3 protease, particularly in their function, but have mutations in their amino acid sequence that make them different in sequence from the wild-type protease.

As used herein, the terms "ASP variant," "ASP protease variant," and "69B protease variant" are used in reference to proteases that are similar to the wild-type ASP, particularly in their function, but have mutations in their amino acid sequence that make them different in sequence from the wild-type protease.

As used herein, "*Cellulomonas* species." refers to all of the species within the genus "*Cellulomonas*," which are Gram-positive bacteria classified as members of the Family Cellulomonadaceae, Suborder Micrococcineae, Order Actinomycetales, Class Actinobacteria. It is recognized that the genus *Cellulomonas* continues to undergo taxonomical reorganization. Thus, it is intended that the genus include species that have been reclassified As used herein, "*Streptomyces* species." refers to all of the species within the genus "*Streptomyces*," which are Gram-positive bacteria classified as members of the Family Streptomycetaceae, Suborder Streptomycineae, Order Actinomycetales, class Actinobacteria. It is recognized that the genus *Streptomyces* continues to undergo taxonomical reorganization. Thus, it is intended that the genus include species that have been reclassified As used herein, "the genus *Bacillus*" includes all species within the genus "*Bacillus*," as known to those of skill in the art, including but not limited to *B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus*, and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*." The production of resistant endospores in the presence of oxygen is considered the defining feature of the genus *Bacillus*, although this characteristic also applies to the recently named *Alicyclobacillus, Amphibacillus, Aneurinibacillus, Anoxybacillus, Brevibacillus, Filobacillus, Gracilibacillus, Halobacillus, Paenibacillus, Salibacillus, Thermobacillus, Ureibacillus*, and *Virgibacillus*, as well as additional organisms.

The terms "polynucleotide" and "nucleic acid", used interchangeably herein, refer to a polymeric form of nucleotides of any length, either ribonucleotides or deoxyribonucleotides. These terms include, but are not limited to, a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases. The following are non-limiting examples of polynucleotides: genes, gene fragments, chromosomal fragments, ESTs, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. In some embodiments, polynucleotides comprise modified nucleotides, such as methylated nucleotides and nucleotide analogs, uracyl, other sugars and linking groups such as fluororibose and thioate, and nucleotide branches. In alternative embodiments, the sequence of nucleotides is interrupted by non-nucleotide components.

As used herein, the terms "DNA construct" and "transforming DNA" are used interchangeably to refer to DNA used to introduce sequences into a host cell or organism. The DNA may be generated in vitro by PCR or any other suitable technique(s) known to those in the art. In particular embodiments, the DNA construct comprises a sequence of interest (e.g., as an incoming sequence). In some embodiments, the sequence is operably linked to additional elements such as control elements (e.g., promoters, etc.). The DNA construct may further comprise a selectable marker. It may further comprise an incoming sequence flanked by homology boxes. In a further embodiment, the transforming DNA comprises other non-homologous sequences, added to the ends (e.g., stuffer sequences or flanks). In some embodiments, the ends of the incoming sequence are closed such that the transforming DNA forms a closed circle. The transforming sequences may be wild-type, mutant or modified. In some embodiments, the DNA construct comprises sequences homologous to the host cell chromosome. In other embodiments, the DNA construct comprises non-homologous sequences. Once the DNA construct is assembled in vitro it may be used to: 1) insert heterologous sequences into a desired target sequence of a host cell, and/or 2) mutagenize a region of the host cell chromosome (i.e., replace an endogenous sequence with a heterologous sequence), 3) delete target genes; and/or introduce a replicating plasmid into the host.

As used herein, the terms "expression cassette" and "expression vector" refer to nucleic acid constructs generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In some embodiments, expression vectors have the ability to incorporate and express heterologous DNA fragments in a host cell. Many prokaryotic and eukaryotic expression vectors are commercially available. Selection of appropriate expression vectors is within the knowledge of those of skill in the art. The term "expression cassette" is used interchangeably herein with "DNA construct," and their grammatical equivalents. Selection of appropriate expression vectors is within the knowledge of those of skill in the art.

As used herein, the term "vector" refers to a polynucleotide construct designed to introduce nucleic acids into one or more cell types. Vectors include cloning vectors, expression vectors, shuttle vectors, plasmids, cassettes and the like. In some embodiments, the polynucleotide construct comprises a DNA sequence encoding the protease (e.g., precursor or mature protease) that is operably linked to a suitable prosequence (e.g., secretory, etc.) capable of effecting the expression of the DNA in a suitable host.

As used herein, the term "plasmid" refers to a circular double-stranded (ds) DNA construct used as a cloning vector, and which forms an extrachromosomal self-replicating genetic element in some eukaryotes or prokaryotes, or integrates into the host chromosome.

As used herein in the context of introducing a nucleic acid sequence into a cell, the term "introduced" refers to any method suitable for transferring the nucleic acid sequence into the cell. Such methods for introduction include but are not limited to protoplast fusion, transfection, transformation, conjugation, and transduction (See e.g., Ferrari et al., "Genetics," in Hardwood et al, (eds.), *Bacillus*, Plenum Publishing Corp., pages 57-72, [1989]).

As used herein, the terms "transformed" and "stably transformed" refers to a cell that has a non-native (heterologous) polynucleotide sequence integrated into its genome or as an episomal plasmid that is maintained for at least two generations.

As used herein, the term "selectable marker-encoding nucleotide sequence" refers to a nucleotide sequence which is capable of expression in the host cells and where expression of the selectable marker confers to cells containing the expressed gene the ability to grow in the presence of a corresponding selective agent or lack of an essential nutrient.

As used herein, the terms "selectable marker" and "selective marker" refer to a nucleic acid (e.g., a gene) capable of expression in host cell which allows for ease of selection of those hosts containing the vector. Examples of such selectable markers include but are not limited to antimicrobials. Thus, the term "selectable marker" refers to genes that provide an indication that a host cell has taken up an incoming DNA of interest or some other reaction has occurred. Typically, selectable markers are genes that confer antimicrobial resistance or a metabolic advantage on the host cell to allow cells containing the exogenous DNA to be distinguished from cells that have not received any exogenous sequence during the transformation. A "residing selectable marker" is one that is located on the chromosome of the microorganism to be transformed. A residing selectable marker encodes a gene that is different from the selectable marker on the transforming DNA construct. Selective markers are well known to those of skill in the art. As indicated above, the marker may be an antimicrobial resistant marker (e.g., $amp^R$; $phleo^R$; $spec^R$; $kan^R$; $ery^R$; $tet^R$; $cmp^R$; and $neo^R$; See e.g., Guerot-Fleury, Gene, 167:335-337 [1995]; Palmeros et al., Gene 247:255-264 [2000]; and Trieu-Cuot et al., Gene, 23:331-341 [1983]). Other markers include, but are not limited to auxotrophic markers, such as tryptophan; and detection markers, such as β-galactosidase.

As used herein, the term "promoter" refers to a nucleic acid sequence that functions to direct transcription of a downstream gene. In some embodiments, the promoter is appropriate to the host cell in which the target gene is being expressed. The promoter, together with other transcriptional and translational regulatory nucleic acid sequences (also termed "control sequences") is necessary to express a given gene. In general, the transcriptional and translational regulatory sequences include, but are not limited to, promoter sequences, ribosomal binding sites, transcriptional start and stop sequences, translational start and stop sequences, and enhancer or activator sequences.

A nucleic acid is "operably linked" when it is placed into a functional relationship with another nucleic acid sequence. For example, DNA encoding a secretory leader (i.e., a signal peptide), is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein the term "gene" refers to a polynucleotide (e.g., a DNA segment), that encodes a polypeptide and includes regions preceding and following the coding regions as well as intervening sequences (introns) between individual coding segments (exons).

As used herein, "homologous genes" refers to a pair of genes from different, but usually related species, which correspond to each other and which are identical or very similar to each other. The term encompasses genes that are separated by speciation (i.e., the development of new species) (e.g., orthologous genes), as well as genes that have been separated by genetic duplication (e.g., paralogous genes).

As used herein, "ortholog" and "orthologous genes" refer to genes in different species that have evolved from a common ancestral gene (i.e., a homologous gene) by speciation. Typically, orthologs retain the same function during the course of evolution. Identification of orthologs finds use in the reliable prediction of gene function in newly sequenced genomes.

As used herein, "paralog" and "paralogous genes" refer to genes that are related by duplication within a genome. While orthologs retain the same function through the course of evolution, paralogs evolve new functions, even though some functions are often related to the original one. Examples of paralogous genes include, but are not limited to genes encoding trypsin, chymotrypsin, elastase, and thrombin, which are all serine proteinases and occur together within the same species.

As used herein, "homology" refers to sequence similarity or identity. This homology is determined using standard techniques known in the art (See e.g., Smith and Waterman, Adv. Appl. Math., 2:482 [1981]; Needleman and Wunsch, J. Mol. Biol., 48:443 [1970]; Pearson and Lipman, Proc. Natl. Acad. Sci. USA 85:2444 [1988]; programs such as GAP, BESTFIT, FASTA, and TFASTA in the Wisconsin Genetics Software Package (Genetics Computer Group, Madison, Wis.); and Devereux et al., Nucl. Acid Res., 12:387-395 [1984]).

As used herein, an "analogous sequence" is one wherein the function of the gene is essentially the same as the gene based on the *Streptomyces* 1AG3 protease. Additionally, analogous genes include at least 45%, 50%, 55%, 60%, 65%, 70%, 75%, 80%, 85%, 90%, 95%, 97%, 98%, 99% or 100% sequence identity with the sequence of the *Streptomyces* strain 1AG3 protease. Alternately, analogous sequences have an alignment of between 70 to 100% of the genes found in the *Streptomyces* strain 1AG3 protease region and/or have at least between 5-10 genes found in the region aligned with the genes in the *Streptomyces* strain 1AG3 chromosome. In additional embodiments more than one of the above properties applies to the sequence. Analogous sequences are determined by known methods of sequence alignment. A commonly used alignment method is BLAST, although as indicated above and below, there are other methods that also find use in aligning sequences.

One example of a useful algorithm is PILEUP. PILEUP creates a multiple sequence alignment from a group of related sequences using progressive, pair-wise alignments. It can also plot a tree showing the clustering relationships used to create the alignment. PILEUP uses a simplification of the progressive alignment method of Feng and Doolittle (Feng and Doolittle, J. Mol. Evol., 35:351-360 [1987]). The method is similar to that described by Higgins and Sharp (Higgins and Sharp, CABIOS 5:151-153 [1989]). Useful PILEUP parameters including a default gap weight of 3.00, a default gap length weight of 0.10, and weighted end gaps.

Another example of a useful algorithm is the BLAST algorithm, described by Altschul et al., (Altschul et al., J. Mol. Biol., 215:403-410, [1990]; and Karlin et al., Proc. Natl. Acad. Sci. USA 90:5873-5787 [1993]). A particularly useful BLAST program is the WU-BLAST-2 program (See, Altschul et al., Meth. Enzymol., 266:460-480 [1996]). WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched. However, the values may be adjusted to increase sensitivity. A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

Thus, "percent (%) nucleic acid sequence identity" is defined as the percentage of nucleotide residues in a candidate sequence that are identical with the nucleotide residues of the starting sequence (i.e., the sequence of interest). A method utilizes the BLASTN module of WU-BLAST-2 set to the default parameters, with overlap span and overlap fraction set to 1 and 0.125, respectively.

As used herein, the term "hybridization" refers to the process by which a strand of nucleic acid joins with a complementary strand through base pairing, as known in the art.

A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature (Tm) of the nucleic acid binding complex or probe. For example, "maximum stringency" typically occurs at about Tm-5° C. (5° below the Tm of the probe); "high stringency" at about 5-10° C. below the Tm; "intermediate stringency" at about 10-20° C. below the Tm of the probe; and "low stringency" at about 20-25° C. below the Tm. Functionally, maximum stringency conditions may be used to identify sequences having strict identity or near-strict identity with the hybridization probe; while an intermediate or low stringency hybridization can be used to identify or detect polynucleotide sequence homologs.

Moderate and high stringency hybridization conditions are well known in the art. An example of high stringency conditions includes hybridization at about 42° C. in 50% formamide, 5×SSC, 5× Denhardt's solution, 0.5% SDS and 100 μg/ml denatured carrier DNA followed by washing two times in 2×SSC and 0.5% SDS at room temperature and two additional times in 0.1×SSC and 0.5% SDS at 42° C. An example of moderate stringent conditions include an overnight incubation at 37° C. in a solution comprising 20% formamide, 5×SSC (150 mM NaCl, 15 mM trisodium citrate), 50 mM sodium phosphate (pH 7.6), 5× Denhardt's solution, 10% dextran sulfate and 20 mg/ml denatured sheared salmon sperm DNA, followed by washing the filters in 1×SSC at about 37-50° C. Those of skill in the art know how to adjust the temperature, ionic strength, etc. as necessary to accommodate factors such as probe length and the like.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention. "Recombination," "recombining," and generating a "recombined" nucleic acid are generally the assembly of two or more nucleic acid fragments wherein the assembly gives rise to a chimeric gene.

In an embodiment, mutant DNA sequences are generated with site saturation mutagenesis in at least one codon. In another embodiment, site saturation mutagenesis is performed for two or more codons. In a further embodiment, mutant DNA sequences have more than 50%, more than 55%, more than 60%, more than 65%, more than 70%, more than 75%, more than 80%, more than 85%, more than 90%, more than 95%, or more than 98% homology with the wild-type sequence. In alternative embodiments, mutant DNA is generated in vivo using any known mutagenic procedure such as, for example, radiation, nitrosoguanidine and the like. The desired DNA sequence is then isolated and used in the methods provided herein.

As used herein, the term "target sequence" refers to a DNA sequence in the host cell that encodes the sequence where it is desired for the incoming sequence to be inserted into the host cell genome. In some embodiments, the target sequence encodes a functional wild-type gene or operon, while in other embodiments the target sequence encodes a functional mutant gene or operon, or a non-functional gene or operon.

As used herein, a "flanking sequence" refers to any sequence that is either upstream or downstream of the sequence being discussed (e.g., for genes A-B-C, gene B is flanked by the A and C gene sequences). In an embodiment, the incoming sequence is flanked by a homology box on each side. In another embodiment, the incoming sequence and the homology boxes comprise a unit that is flanked by stuffer sequence on each side. In some embodiments, a flanking sequence is present on only a single side (either 3' or 5'), but in one embodiment, it is on each side of the sequence being flanked. In some embodiments, a flanking sequence is present on only a single side (either 3' or 5'), while in other embodiments, it is present on each side of the sequence being flanked.

As used herein, the term "stuffer sequence" refers to any extra DNA that flanks homology boxes (typically vector sequences). However, the term encompasses any non-homologous DNA sequence. Not to be limited by any theory, a stuffer sequence provides a noncritical target for a cell to initiate DNA uptake.

As used herein, the term "chromosomal integration" refers to the process whereby an incoming sequence is introduced into the chromosome of a host cell. The homologous regions of the transforming DNA align with homologous regions of the chromosome. Subsequently, the sequence between the homology boxes is replaced by the incoming sequence in a double crossover (i.e., homologous recombination). In some embodiments of the present invention, homologous sections of an inactivating chromosomal segment of a DNA construct align with the flanking homologous regions of the indigenous chromosomal region of the *Bacillus* chromosome. Subsequently, the indigenous chromosomal region is deleted by the DNA construct in a double crossover (i.e., homologous recombination).

"Homologous recombination" means the exchange of DNA fragments between two DNA molecules or paired chromosomes at the site of identical or nearly identical nucleotide sequences. In an embodiment, chromosomal integration is homologous recombination.

"Homologous sequences" as used herein means a nucleic acid or polypeptide sequence having 100%, 99%, 98%, 97%, 96%, 95%, 94%, 93%, 92%, 91%, 90%, 88%, 85%, 80%, 75%, or 70% sequence identity to another nucleic acid or polypeptide sequence when optimally aligned for comparison. In some embodiments, homologous sequences have between 85% and 100% sequence identity, while in other embodiments there is between 90% and 100% sequence identity, and in more some embodiments, there is 95% and 100% sequence identity.

As used herein "amino acid" refers to peptide or protein sequences or portions thereof. The terms "protein," "peptide," and "polypeptide" are used interchangeably.

As used herein, "protein of interest" and "polypeptide of interest" refer to a protein/polypeptide that is desired and/or being assessed. In some embodiments, the protein of interest is expressed intracellularly, while in other embodiments, it is a secreted polypeptide. In particular embodiments, these enzyme include the serine proteases described herein. In some embodiments, the protein of interest is a secreted polypeptide which is fused to a signal peptide (i.e., an amino-terminal extension on a protein to be secreted). Nearly all secreted proteins use an amino-terminal protein extension which plays a crucial role in the targeting to and translocation of precursor proteins across the membrane. This extension is proteolytically removed by a signal peptidase during or immediately following membrane transfer.

As used herein, the term "heterologous protein" refers to a protein or polypeptide that does not naturally occur in the host cell. Examples of heterologous proteins include enzymes such as hydrolases including proteases. In some embodiments, the gene encoding the proteins are naturally occurring genes, while in other embodiments, mutated and/or synthetic genes are used.

As used herein, "homologous protein" refers to a protein or polypeptide native or naturally occurring in a cell. In certain embodiments, the cell is a Gram-positive cell, while in other embodiments, the cell is a *Bacillus* host cell. In alternative embodiments, the homologous protein is a native protein produced by other organisms, including but not limited to *E. coli, Streptomyces, Trichoderma*, and *Aspergillus*. This disclosure also provides host cells producing the homologous protein via recombinant DNA technology.

"Host strain" or "host cell" refers to a suitable host for an expression vector comprising DNA according to some embodiments of the present invention.

An enzyme is "overexpressed" in a host cell if the enzyme is expressed in the cell at a higher level that the level at which it is expressed in a corresponding wild-type cell.

A "prosequence" is an amino acid sequence between the signal sequence and mature protease that is necessary for the secretion of the protease. Cleavage of the pro sequence will result in a mature active protease.

The term "signal sequence" or "signal peptide" refers to any sequence of nucleotides and/or amino acids which may participate in the secretion of the mature or precursor forms of the protein. This definition of signal sequence is a functional one, meant to include all those amino acid sequences encoded by the N-terminal portion of the protein gene, which participate in the effectuation of the secretion of protein. They are often, but not universally, bound to the N-terminal portion of a protein or to the N-terminal portion of a precursor protein. The signal sequence may be endogenous or exogenous. The signal sequence may be that normally associated with the protein (e.g., protease), or may be from a gene encoding another secreted protein. One exemplary exogenous signal sequence comprises the first seven amino acid residues of the signal sequence from *Bacillus* subtilis subtilisin fused to the remainder of the signal sequence of the subtilisin from *Bacillus* lentus (ATCC 21536).

The term "mature" form of a protein or peptide refers to the final functional form of the protein or peptide. For example, a mature form of the subject protease at least includes the amino acid sequence set forth in SEQ ID NO:9.

The term "precursor" form of a protein or peptide refers to a mature form of the protein having a prosequence operably linked to the amino or carbonyl terminus of the protein. The precursor may also have a "signal" sequence operably linked, to the amino terminus of the prosequence. The precursor may also have additional polynucleotides that are involved in post-translational activity (e.g., polynucleotides cleaved therefrom to leave the mature form of a protein or peptide).

"Naturally occurring enzyme" refers to an enzyme having the unmodified amino acid sequence identical to that found in nature. Naturally occurring enzymes include native enzymes, those enzymes naturally expressed or found in the particular microorganism.

The terms "derived from" and "obtained from" refer to not only a protease produced or producible by a strain of the organism in question, but also a protease encoded by a DNA sequence isolated from such strain and produced in a host organism containing such DNA sequence. Additionally, the term refers to a protease which is encoded by a DNA sequence of synthetic and/or cDNA origin and which has the identifying characteristics of the protease in question. To exemplify, "proteases derived from Streptomyces" refers to those enzymes having proteolytic activity which are naturally-produced by *Streptomyces*, as well as to serine proteases like those produced by *Streptomyces* sources but which through the use of genetic engineering techniques are produced by non-*Streptomyces* organisms transformed with a nucleic acid encoding said serine proteases.

A "derivative" within the scope of this definition generally retains the characteristic proteolytic activity observed in the wild-type, native or parent form to the extent that the derivative is useful for similar purposes as the wild-type, native or parent form. Functional derivatives of serine protease encompass naturally occurring, synthetically or recombinantly produced peptides or peptide fragments which have the general characteristics of the subject serine protease.

The term "functional derivative" refers to a derivative of a nucleic acid which has the functional characteristics of a nucleic acid which encodes serine protease. Functional derivatives of a nucleic acid which encode the subject serine protease encompass naturally occurring, synthetically or recombinantly produced nucleic acids or fragments and encode serine protease characteristic of the present invention. Wild type nucleic acid encoding serine proteases according to the invention include naturally occurring alleles and homologues based on the degeneracy of the genetic code known in the art.

The term "identical" in the context of two nucleic acids or polypeptide sequences refers to the residues in the two sequences that are the same when aligned for maximum correspondence, as measured using one of the following sequence comparison or analysis algorithms.

The term "optimal alignment" refers to the alignment giving the highest percent identity score.

"Percent sequence identity," "percent amino acid sequence identity," "percent gene sequence identity," and/or "percent nucleic acid/polynucloetide sequence identity," with respect to two amino acid, polynucleotide and/or gene sequences (as appropriate), refer to the percentage of residues that are identical in the two sequences when the sequences are optimally aligned. Thus, 80% amino acid sequence identity means that 80% of the amino acids in two optimally aligned polypeptide sequences are identical.

The phrase "substantially identical" in the context of two nucleic acids or polypeptides thus refers to a polynucleotide or polypeptide that comprising at least 70% sequence identity, at least 75%, at least 80%, at least 85%, at least 90%, at least 95%, at least 97%, at least 98% and at least 99% sequence identity as compared to a reference sequence using the programs or algorithms (e.g., BLAST, ALIGN, CLUSTAL) using standard parameters. One indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, for example, where the two peptides differ only by a conservative substitution. Another indication that two nucleic acid sequences are substantially identical is that the two molecules hybridize to each other under stringent conditions (e.g., within a range of medium to high stringency).

The term "isolated" or "purified" refers to a material that is removed from its original environment (e.g., the natural environment, if it is naturally occurring). For example, the material is said to be "purified" when it is present in a particular composition in a higher or lower concentration than exists in a naturally occurring or wild type organism or in combination with components not normally present upon expression from a naturally occurring or wild type organism. For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector, and/or such polynucleotides or polypeptides could be part of a composition, and still be isolated in that such vector or composition is not part of its natural environment. In certain embodiments, a nucleic acid or protein is said to be purified, for example, if it gives rise to essentially one band in an electrophoretic gel or blot.

The term "isolated", when used in reference to a DNA sequence, refers to a DNA sequence that has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (See e.g., Dynan and Tijan, Nature 316:774-78 [1985]). The term "an isolated DNA sequence" is alternatively referred to as "a cloned DNA sequence".

The term "isolated," when used in reference to a protein, refers to a protein that is found in a condition other than its native environment. In one form, the isolated protein is substantially free of other proteins, particularly other homologous proteins. An isolated protein may be more than 10% pure, more than 20% pure, and more than 30% pure, as determined by SDS-PAGE. Further aspects of the invention encompass the protein in a highly purified form (i.e., more than 40% pure, more than 60% pure, more than 80% pure, more than 90% pure, more than 95% pure, more than 97% pure, and even more than 99% pure), as determined by SDS-PAGE.

As used herein, the term "functional assay" refers to an assay that provides an indication of a protein's activity. In particular embodiments, the term refers to assay systems in which a protein is analyzed for its ability to function in its usual capacity. For example, in the case of enzymes, a functional assay involves determining the effectiveness of the enzyme in catalyzing a reaction.

As used herein, the term "target property" refers to the property of the starting gene that is to be altered. It is not intended that the present invention be limited to any particular target property. However, in some embodiments, the target property is the stability of a gene product (e.g., resistance to denaturation, proteolysis or other degradative factors), while in other embodiments, the level of production in a production host is altered. Indeed, it is contemplated that any property of a starting gene will find use in the present invention.

The term "property" or grammatical equivalents thereof in the context of a polypeptide, as used herein, refer to any characteristic or attribute of a polypeptide that can be selected or detected. These properties include, but are not limited to oxidative stability, substrate specificity, catalytic activity, thermal stability, alkaline stability, pH activity profile, resistance to proteolytic degradation, KM, kcat, $kcat/k_M$ ratio, protein folding, inducing an immune response, ability to bind to a ligand, ability to bind to a receptor, ability to be secreted, ability to be displayed on the surface of a cell, ability to oligomerize, ability to signal, ability to stimulate cell proliferation, ability to inhibit cell proliferation, ability to induce apoptosis, ability to be modified by phosphorylation or glycosylation, ability to treat disease.

The terms "modified sequence" and "modified genes" are used interchangeably herein to refer to a sequence that includes a deletion, insertion or interruption of naturally occurring nucleic acid sequence. In some embodiments, the expression product of the modified sequence is a truncated protein (e.g., if the modification is a deletion or interruption of the sequence). In some particular embodiments, the truncated protein retains biological activity. In alternative embodiments, the expression product of the modified sequence is an elongated protein (e.g., modifications comprising an insertion into the nucleic acid sequence). In some embodiments, an insertion leads to a truncated protein (e.g., when the insertion results in the formation of a stop codon). Thus, an insertion may result in either a truncated protein or an elongated protein as an expression product.

The terms "wild-type sequence," or "wild-type gene" are used interchangeably herein, to refer to a sequence that is native or naturally occurring in a host cell. In some embodiments, the wild-type sequence refers to a sequence of interest that is the starting point of a protein engineering project. The wild-type sequence may encode either a homologous or heterologous protein. A homologous protein is one the host cell would produce without intervention. A heterologous protein is one that the host cell would not produce but for the intervention.

As used herein, the term "antibodies" refers to immunoglobulins. Antibodies include but are not limited to immunoglobulins obtained directly from any species from which it is desirable to produce antibodies. In addition, the present invention encompasses modified antibodies. The term also refers to antibody fragments that retain the ability to bind to the epitope that the intact antibody binds and include polyclonal antibodies, monoclonal antibodies, chimeric antibodies, anti-idiotype (anti-ID) antibodies. Antibody fragments include, but are not limited to the complementarity-determining regions (CDRs), single-chain fragment variable regions (scFv), heavy chain variable region (VH), light chain variable region (VL). Polyclonal and monoclonal antibodies are also encompassed by the present invention. The antibodies may be monoclonal antibodies.

The term "oxidation stable" refers to proteases of the present invention that retain a specified amount of enzymatic activity over a given period of time under conditions prevailing during the proteolytic, hydrolyzing, cleaning or other process of the invention, for example while exposed to or contacted with bleaching agents or oxidizing agents. In some embodiments, the proteases retain at least 50%, 60%, 70%, 75%, 80%, 85%, 90%, 92%, 95%, 96%, 97%, 98% or 99% proteolytic activity after contact with a bleaching or oxidizing agent over a given time period, for example, at least 1 minute, 3 minutes, 5 minutes, 8 minutes, 12 minutes, 16 minutes, 20 minutes, etc. In some embodiments, the stability is measured as described in the Examples.

The term "chelator stable" refers to proteases of the present invention that retain a specified amount of enzymatic activity over a given period of time under conditions prevailing during the proteolytic, hydrolyzing, cleaning or other process of the invention, for example while exposed to or contacted with chelating agents. In some embodiments, the proteases retain at least 50%, 60%, 70%, 75%, 80%, 85%, 90%, 92%, 95%, 96%, 97%, 98% or 99% proteolytic activity after contact with a chelating agent over a given time period, for example, at least 10 minutes, 20 minutes, 40 minutes, 60 minutes, 100 minutes, etc.

The terms "thermally stable" and "thermostable" refer to proteases of the present invention that retain a specified amount of enzymatic activity after exposure to identified temperatures over a given period of time under conditions prevailing during the proteolytic, hydrolyzing, cleaning or other process of the invention, for example while exposed to altered temperatures. Altered temperatures includes increased or decreased temperatures. In some embodiments, the proteases retain at least 50%, 60%, 70%, 75%, 80%, 85%, 90%, 92%, 95%, 96%, 97%, 98% or 99% proteolytic activity after exposure to altered temperatures over a given time period, for example, at least 60 minutes, 120 minutes, 180 minutes, 240 minutes, 300 minutes, etc.

The term "enhanced stability" in the context of an oxidation, chelator, thermal and/or pH stable protease refers to a higher retained proteolytic activity over time as compared to other serine proteases (e.g., subtilisin proteases) and/or wild-type enzymes.

The term "diminished stability" in the context of an oxidation, chelator, thermal and/or pH stable protease refers to a lower retained proteolytic activity over time as compared to other serine proteases (e.g., subtilisin proteases) and/or wild-type enzymes.

The term "cleaning activity" refers to the cleaning performance achieved by the protease under conditions prevailing during the proteolytic, hydrolyzing, cleaning or other process of the invention. In some embodiments, cleaning performance is determined by the application of various cleaning assays concerning enzyme sensitive stains, for example grass, blood, milk, or egg protein as determined by various chromatographic, spectrophotometric or other quantitative methodologies after subjection of the stains to standard wash conditions. Exemplary assays include, but are not limited to those described in WO 99/34011, and U.S. Pat. No. 6,605,458 (both of which are herein incorporated by reference), as well as those methods included in the Examples.

The term "cleaning effective amount" of a protease refers to the quantity of protease described hereinbefore that achieves a desired level of enzymatic activity in a specific cleaning composition. Such effective amounts are readily ascertained by one of ordinary skill in the art and are based on many factors, such as the particular protease used, the cleaning application, the specific composition of the cleaning composition, and whether a liquid or dry (e.g., granular, bar) composition is required, etc.

The term "cleaning adjunct materials," as used herein, means any liquid, solid or gaseous material selected for the particular type of cleaning composition desired and the form of the product (e.g., liquid, granule, powder, bar, paste, spray, tablet, gel; or foam composition), which materials may be also compatible with the protease enzyme used in the composition. In some embodiments, granular compositions are in "compact" form, while in other embodiments, the liquid compositions are in a "concentrated" form.

The term "enhanced performance" in the context of cleaning activity refers to an increased or greater cleaning activity of certain enzyme sensitive stains such as egg, milk, grass or blood, as determined by usual evaluation after a standard wash cycle and/or multiple wash cycles.

The term "diminished performance" in the context of cleaning activity refers to an decreased or lesser cleaning activity of certain enzyme sensitive stains such as egg, milk, grass or blood, as determined by usual evaluation after a standard wash cycle.

The term "comparative performance" in the context of cleaning activity refers to at least 60%, at least 70%, at least 80% at least 90% at least 95% of the cleaning activity of a comparative subtilisin protease (e.g., commercially available proteases), including but not limited to OPTIMASE™ protease (Genencor), PURAFECT™ protease (Genencor), SAVINASE™ protease (Novozymes), BPN'-variants (See e.g., U.S. Pat. No. Re 34,606), RELASE™, DURAZYME™, EVERLASE™, KANNASE™ protease (Novozymes), MAXACAL™, MAXAPEM™, PROPERASE™ proteases (Genencor; See also, U.S. Pat. No. Re 34,606, U.S. Pat. Nos. 5,700,676; 5,955,340; 6,312,936; 6,482,628), and *B. lentus* variant protease products [for example those described in WO 92/21760, WO 95/23221 and/or WO 97/07770 (Henkel). Exemplary subtilisin protease variants include, but are not limited to those having substitutions or deletions at residue positions equivalent to positions 76, 101, 103, 104, 120, 159, 167, 170, 194, 195, 217, 232, 235, 236, 245, 248, and/or 252 of BPN'. Cleaning performance can be determined by comparing the proteases of the present invention with those subtilisin proteases in various cleaning assays concerning enzyme sensitive stains such as grass, blood or milk as determined by usual spectrophotometric or analytical methodologies after standard wash cycle conditions.

As used herein, a "low detergent concentration" system includes detergents where less than about 800 ppm of detergent components are present in the wash water. Japanese detergents are typically considered low detergent concentration systems, as they have usually have approximately 667 ppm of detergent components present in the wash water.

As used herein, a "medium detergent concentration" systems includes detergents wherein between about 800 ppm and about 2000 ppm of detergent components are present in the wash water. North American detergents are generally considered to be medium detergent concentration systems as they have usually approximately 975 ppm of detergent components present in the wash water. Brazilian detergents typically have approximately 1500 ppm of detergent components present in the wash water.

As used herein, "high detergent concentration" systems includes detergents wherein greater than about 2000 ppm of detergent components are present in the wash water. European detergents are generally considered to be high detergent concentration systems as they have approximately 3000-8000 ppm of detergent components in the wash water.

As used herein, "fabric cleaning compositions" include hand and machine laundry detergent compositions including laundry additive compositions and compositions suitable for use in the soaking and/or pretreatment of stained fabrics (e.g., clothes, linens, and other textile materials).

As used herein, "non-fabric cleaning compositions" include non-textile (i.e., fabric) surface cleaning compositions, including but not limited to dishwashing detergent compositions, oral cleaning compositions, denture cleaning compositions, and personal cleansing compositions.

The "compact" form of the cleaning compositions herein is best reflected by density and, in terms of composition, by the amount of inorganic filler salt. Inorganic filler salts are conventional ingredients of detergent compositions in powder form. In conventional detergent compositions, the filler salts are present in substantial amounts, typically 17-35% by weight of the total composition. In contrast, in compact compositions, the filler salt is present in amounts not exceeding 15% of the total composition. In some embodiments, the filler salt is present in amounts that do not exceed 10%, or 5%, by weight of the composition. In some embodiments, the inorganic filler salts are selected from the alkali and alkaline-earth-metal salts of sulfates and chlorides. An exemplary filler salt is sodium sulfate.

II. Serine Protease Enzymes and Nucleic Acid Encoding Serine Protease Enzymes

The present invention provides isolated polynucleotides encoding amino acid sequences, encoding proteases. In some embodiments, these polynucleotides encode polypeptides that comprise at least 65% amino acid sequence identity, at least 70% amino acid sequence identity, at least 75% amino acid sequence identity, at least 80% amino acid sequence identity, at least 85% amino acid sequence identity, at least 90% amino acid sequence identity, at least 92% amino acid sequence identity, at least 95% amino acid sequence identity, at least 97% amino acid sequence identity, at least 98% amino acid sequence identity, and at least 99% amino acid sequence identity to an amino acid sequence as shown in SEQ ID NOS:3, 8, and 11, (e.g., at least a portion of the amino acid sequence encoded by the polynucleotide having proteolytic activity, including the mature protease catalyzing the hydrolysis of peptide linkages of substrates), and/or demonstrating comparable or enhanced washing performance under identified wash conditions.

In some embodiments, the percent identity (amino acid sequence, nucleic acid sequence, gene sequence) is determined by a direct comparison of the sequence information between two molecules by aligning the sequences, counting the exact number of matches between the two aligned sequences, dividing by the length of the shorter sequence, and multiplying the result by 100. Readily available computer programs find use in these analysis, such as those described above. Programs for determining nucleotide sequence identity are available in the Wisconsin Sequence Analysis Package, Version 8 (Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above.

An example of an algorithm that is suitable for determining sequence similarity is the BLAST algorithm, which is described in Altschul, et al., J. Mol. Biol., 215:403-410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence that either match or satisfy some positive-valued threshold score T when aligned with a word of the same length in a database sequence. These initial neighborhood word hits act as starting points to find longer HSPs containing them. The word hits are expanded in both directions along each of the two sequences being compared for as far as the cumulative alignment score can be increased. Extension of the word hits is stopped when: the cumulative alignment score falls off by the quantity X from a maximum achieved value; the cumulative score goes to zero or below; or the end of either sequence is reached. The BLAST algorithm parameters W, T, and X determine the sensitivity and speed of the alignment. The BLAST program uses as defaults a wordlength (W) of 11, the BLOSUM62 scoring matrix (See, Henikoff & Henikoff, Proc. Natl. Acad. Sci. USA 89:10915 (1989)) alignments (B) of 50, expectation (E) of 10, M'5, N'-4, and a comparison of both strands.

The BLAST algorithm then performs a statistical analysis of the similarity between two sequences (See e.g., Karlin and Altschul, Proc. Nat'l. Acad. Sci. USA 90:5873-5787 [1993]). One measure of similarity provided by the BLAST algorithm is the smallest sum probability (P(N)), which provides an indication of the probability by which a match between two nucleotide or amino acid sequences would occur by chance. For example, a nucleic acid is considered similar to a serine protease nucleic acid of this invention if the smallest sum probability in a comparison of the test nucleic acid to a serine protease nucleic acid is less than about 0.1, less than about 0.01, or less than about 0.001. Where the test nucleic acid encodes a serine protease polypeptide, it is considered similar to a specified serine protease nucleic acid if the comparison results in a smallest sum probability of less than about 0.5, e.g., less than about 0.2.

In some embodiments of the present invention, sequences were analyzed by BLAST and protein translation sequence tools. In some experiments, Basic BLAST version 2.0 was used. The program chosen was "BlastX", and the database chosen was "nr". Standard/default parameter values were employed.

In some embodiments, the present invention encompasses the approximately 1389 base pairs in length polynucleotide set forth in SEQ ID NO1, which encodes the 1AG3 protease described herein. A start codon and stop codon is shown in bold and a potential ribosomal binding site is underlined in SEQ ID NO:1. In another embodiment of the present invention, the polynucleotides encoding these amino acid sequences comprise a 1362 base pair portion (residues 1-1362 of SEQ ID NO:2) that, if expressed, is believed to encode a signal sequence (nucleotides 1-75 of SEQ ID NO:2) (i.e., SEQ ID NO:4) encoding amino acids 1-25 of SEQ ID NO:3 (i.e., SEQ ID NO:5), an N-terminal prosequence (nucleotides 76-591 of SEQ ID NO:2 (SEQ ID NO:6) encoding amino acid residues 26-197 of SEQ ID NO:3) (i.e., SEQ ID NO:7); a mature protease sequence (nucleotides 592-1359 of SEQ ID NO:2 encoding amino acid residues 198-453 of SEQ ID NO:3 (amino acid residues 1-256 of SEQ ID NO:9). Alternatively, the signal peptide, the N-terminal pro-sequence and mature serine protease sequence is numbered in relation to the amino acid residues of the mature protease of SEQ ID NO:9 being numbered 1-256, i.e., signal peptide (residues −198 to −173), an N-terminal pro sequence (residues −172 to −1), the mature serine protease sequence (residues 1-256). In another embodiment of the present invention, the polynucleotide encoding an amino acid sequence having proteolytic activity comprises a nucleotide sequence of nucleotides 1 to 1362 of the portion of SEQ ID NO:2 encoding the signal peptide and precursor protease. In another embodiment of the present invention, the polynucleotide encoding an amino acid sequence comprises the sequence of nucleotides 1 to 1287 of the polynucleotide (SEQ ID NO:10) encoding the precursor *Streptomyces* protease (SEQ ID NO:11). In yet another embodiment, the polynucleotide encoding an amino acid sequence comprises the sequence of nucleotides 1 to 768 of the portion of the polynucleotide (SEQ ID NO:8) encoding the mature *Streptomyces* protease (SEQ ID NO:9). These sequences are provided below:

SEQ ID NO:1 provides the complete 1AG3 nucleotide sequence, including flanking regions:

```
  1 GACAGC GAGGAG ACCCCT CATGCA CCGCAG ACGCGG AGCGCT ATTCGC CGGCGC CGTGGC    (SEQ ID NO: 1)
    CTGTCG CTCCTC TGGGGA GTACGT GGCGTC TGCGCC TCGCGA TAAGCG GCCGCG GCACCG

61 GATAGC CGCCCT GACGAT CGCCGC CGCGCC GGCCAC CGCCGG ACCGGC CCTCGC CCCGCC
    CTATCG GCGGGA CTGCTA GCGGCG GCGCGG CCGGTG GCGGCC TGGCCG GGAGCG GGGCGG

121 ACCGGC CCAGGA GACGGC GGCCCA GGAGAT CCCTGC CGGCAT GCTGCA GGCCAT GCAGCG
    TGGCCG GGTCCT CTGCCG CCGGGT CCTCTA GGGACG GCCGTA CGACGT CCGGTA CGTCGC

181 TGATCT CGGCCT CACCGA GCAGCA GGCCGA GGAGCG CGTGGC CAACGA GTACCA AGCGGG
    ACTAGA GCCGGA GTGGCT CGTCGT CCGGCT CCTCGC GCACCG GTTGCT CATGGT TCGCCC

241 CCAGCT GGAGCC ACGGCT GCGGGC GCAATT GGCGGA CACCTT CGCCGG TTCCTG GACCAG
    GGTCGA CCTCGG TGCCGA CGCCCG CGTTAA CCGCCT GTGGAA GCGGCC AAGGAC CTGGTC

301 GGGCGA GACCGC CGAGCT GGTCGT GGCCAC CACCGA CCGCGA GCAGCT ACCGGC GCTGAC
    CCCGCT CTGGCG GCTCGA CCAGCA CCGGTG GTGGCT GGCGCT CGTCGA TGGCCG CGACTG

361 GGCGGC GGGCGT GCGGGC CACCGT GGCCGA GCACAG CCTGTC CGAGCT CGAGGC CGTGAA
    CCGCCG CCCGCA CGCCCG GTGGCA CCGGCT CGTGTC GGACAG GCTCGA GCTCCG GCACTT

421 GGAGAC ACTGGA CGAGGC CGCCGA GGAGCA CGCCAC GACCGA GGCGCC CGTGTG GTACGT
    CCTCTG TGACCT GCTCCG GCGGCT CCTCGT GCGGTG CTGGCT CCGCGG GCACAC CATGCA

481 GGATGT CACGAG CAACAC GGTCAT CGTGCA CGCCCA GGACGT GACGGC CGGGCG CGACTT
    CCTACA GTGCTC GTTGTG CCAGTA GCACGT GCGGGT CCTGCA CTGCCG GCCCGC GCTGAA

541 CGTCTC GGCCGC GGGCGT GGACCC CGCCGC GGTCCA CGTGCT GCGCTC GGACGA GCAGCC
    GCAGAG CCGGCG CCCGCA CCTGGG GCGGCG CCAGGT GCACGA CGCGAG CCTGCT CGTCGG

601 GCGGCC TTACCA CGACCT GCGGGG TGGGGA GGCGTA CTACAT GGGCAG CGGAGG GCGCTG
    CGCCGG AATGGT GCTGGA CGCCCC ACCCCT CCGCAT GATGTA CCCGTC GCCTCC CGCGAC

661 CTCGGT CGGCTT CTCCGT TCGCCG CGGAAC TCAGGC GGGCTT CGCGAC CGCGGG TCACTG
    GAGCCA GCCGAA GAGGCA AGCGGC GCCTTG AGTCCG CCCGAA GCGCTG GCGCCC AGTGAC

721 CGGCCG GGTCGG CACCAC CACACG GGGCTT CAACCA GGTGGC GCAGGG CACCTT CCAGGG
    GCCGGC CCAGCC GTGGTG GTGTGC CCCGAA GTTGGT CCACCG CGTCCC GTGGAA GGTCCC

781 CTCCAT CTTCCC CGGGCG CGACAT GGGCTG GGTCGC GGTCAA CTCCAA CTGGAA CACCAC
    GAGGTA GAAGGG GCCCGC GCTGTA CCCGAC CCAGCG CCAGTT GAGGTT GACCTT GTGGTG

841 CCCCTT CGTCCG CGGCCA GGGGGG CGCGAA CGTGAC GGTGGC GGGTTC GCAGCA GGCTCC
    GGGGAA GCAGGC GCCGGT CCCCCC GCGCTT GCACTG CCACCG CCCAAG CGTCGT CCGAGG
```

```
 901 GGTCGG CTCCTC GGTGTG CCGTTC CGGCTC CACCAC CGGCTG GCACTG CGGCAC CATCCA
     CCAGCC GAGGAG CCACAC GGCAAG GCCGAG GTGGTG GCCGAC CGTGAC GCCGTG GTAGGT

961 GCAGCA CAACAC CTCGGT GCGCTA TCCGGA GGGCAC CATCAG CGGAGT GACCAG GACCTC
     CGTCGT GTTGTG GAGCCA CGCGAT AGGCCT CCCGTG GTAGTC GCCTCA CTGGTC CTGGAG

1021 GGTGTG CGCCGA ACCCGG TGACTC CGGCGG CGCCTA CATCTC CGGGAA CCAGGC CCAGGG
     CCACAC GCGGCT TGGGCC ACTGAG GCCGCC GCGGAT GTAGAG GCCCTT GGTCCG GGTCCC

1081 CGTGAC CTCCGG CGGCTC GGGCAA CTGCCG CACCGG TGGCAC CACCTA CCACCA GCCGAT
     GCACTG GAGGCC GCCGAG CCCGTT GACGGC GTGGCC ACCGTG GTGGAT GGTGGT CGGCTA

1141 CAACCC GCTGCT GGCACA GTGGAA CCTGAC CCTCGT GACCAC GGGCAA CGGCGG CGACCC
     GTTGGG CGACGA CCGTGT CACCTT GGACTG GGAGCA CTGGTG CCCGTT GCCGCC GCTGGG

1201 GGGCGA CCCCGG TGACCC GGGCGA CCCGGG TGAGCC CGGCGG CAGCTG GTCCGC CGGGAC
     CCCGCT GGGGCC ACTGGG CCCGCT GGGCCC ACTCGG GCCGCC GTCGAC CAGGCG GCCCTG

1261 CAGTTA CGCGGT CGGCGA CCGGGT GACCTA CGGCGG CGCGGA GTACCG CTGCCT GCAGGC
     GTCAAT GCGCCA GCCGCT GGCCCA CTGGAT GCCGCC GCGCCT CATGGC GACGGA CGTCCG

1321 CCACGT CGCCCA GTCCGG CTGGAC GCCCCC GAACAC GCCCGC CCTCTG GCAGCG CGTGTG
     GGTGCA GCGGGT CAGGCC GACCTG CGGGGG CTTGTG CGGGCG GGAGAC CGTCGC GCACAC

1381 ACACGA CCA
     TGTGCT GGT
```

In the above sequence, the putative ribosomal binding site is underlined. The start and stop codons are shown in bold.

SEQ ID NO:2 below provides the polynucleotide sequence of 1AG3 protease/Open reading frame of 1AG3 protease:

```
   1 ATGCACCGCA GACGCGGAGC GCTATTCGCC GGCGCCGTGG CGATAGCCGC    (SEQ ID NO: 2)
     TACGTGGCGT CTGCGCCTCG CGATAAGCGG CCGCGGCACC GCTATCGGCG

51 CCTGACGATC GCCGCCGCGC CGGCCACCGC CGGACCGGCC CTCGCCCCGC
     GGACTGCTAG CGGCGGCGCG GCCGGTGGCG GCCTGGCCGG GAGCGGGGCG

101 CACCGGCCCA GGAGACGGCG GCCCAGGAGA TCCCTGCCGG CATGCTGCAG
     GTGGCCGGGT CCTCTGCCGC CGGGTCCTCT AGGGACGGCC GTACGACGTC

151 GCCATGCAGC GTGATCTCGG CCTCACCGAG CAGCAGGCCG AGGAGCGCGT
     CGGTACGTCG CACTAGAGCC GGAGTGGCTC GTCGTCCGGC TCCTCGCGCA

201 GGCCAACGAG TACCAAGCGG GCCAGCTGGA GCCACGGCTG CGGGCGCAAT
     CCGGTTGCTC ATGGTTCGCC CGGTCGACCT CGGTGCCGAC GCCCGCGTTA

251 TGGCGGACAC CTTCGCCGGT TCCTGGACCA GGGGCGAGAC CGCCGAGCTG
     ACCGCCTGTG GAAGCGGCCA AGGACCTGGT CCCCGCTCTG GCGGCTCGAC

301 GTCGTGGCCA CCACCGACCG CGAGCAGCTA CCGGCGCTGA CGGCGGCGGG
     CAGCACCGGT GGTGGCTGGC GCTCGTCGAT GGCCGCGACT GCCGCCGCCC

351 CGTGCGGGCC ACCGTGGCCG AGCACAGCCT GTCCGAGCTC GAGGCCGTGA
     GCACGCCCGG TGGCACCGGC TCGTGTCGGA CAGGCTCGAG CTCCGGCACT

401 AGGAGACACT GGACGAGGCC GCCGAGGAGC ACGCCACGAC CGAGGCGCCC
     TCCTCTGTGA CCTGCTCCGG CGGCTCCTCG TGCGGTGCTG GCTCCGCGGG

451 GTGTGGTACG TGGATGTCAC GAGCAACACG GTCATCGTGC ACGCCCAGGA
     CACACCATGC ACCTACAGTG CTCGTTGTGC CAGTAGCACG TGCGGGTCCT

501 CGTGACGGCC GGGCGCGACT TCGTCTCGGC CGCGGGCGTG GACCCCGCCG
     GCACTGCCGG CCCGCGCTGA AGCAGAGCCG GCGCCCGCAC CTGGGGCGGC

551 CGGTCCACGT GCTGCGCTCG GACGAGCAGC CGCGGCCTTA CCACGACCTG
     GCCAGGTGCA CGACGCGAGC CTGCTCGTCG GCGCCGGAAT GGTGCTGGAC

601 CGGGGTGGGG AGGCGTACTA CATGGGCAGC GGAGGGCGCT GCTCGGTCGG
     GCCCCACCCC TCCGCATGAT GTACCCGTCG CCTCCCGCGA CGAGCCAGCC

651 CTTCTCCGTT CGCCGCGGAA CTCAGGCGGG CTTCGCGACC GCGGGTCACT
     GAAGAGGCAA GCGGCGCCTT GAGTCCGCCC GAAGCGCTGG CGCCCAGTGA

701 GCGGCCGGGT CGGCACCACC ACACGGGGCT TCAACCAGGT GGCGCAGGGC
     CGCCGGCCCA GCCGTGGTGG TGTGCCCCGA AGTTGGTCCA CCGCGTCCCG
```

```
 751 ACCTTCCAGG GCTCCATCTT CCCCGGGCGC GACATGGGCT GGGTCGCGGT
     TGGAAGGTCC CGAGGTAGAA GGGGCCCGCG CTGTACCCGA CCCAGCGCCA

801 CAACTCCAAC TGGAACACCA CCCCCTTCGT CCGCGGCCAG GGGGGCGCGA
     GTTGAGGTTG ACCTTGTGGT GGGGGAAGCA GGCGCCGGTC CCCCCGCGCT

851 ACGTGACGGT GGCGGGTTCG CAGCAGGCTC CGGTCGGCTC CTCGGTGTGC
     TGCACTGCCA CCGCCCAAGC GTCGTCCGAG GCCAGCCGAG GAGCCACACG

901 CGTTCCGGCT CCACCACCGG CTGGCACTGC GGCACCATCC AGCAGCACAA
     GCAAGGCCGA GGTGGTGGCC GACCGTGACG CCGTGGTAGG TCGTCGTGTT

951 CACCTCGGTG CGCTATCCGG AGGGCACCAT CAGCGGAGTG ACCAGGACCT
     GTGGAGCCAC GCGATAGGCC TCCCGTGGTA GTCGCCTCAC TGGTCCTGGA

1001 CGGTGTGCGC CGAACCCGGT GACTCCGGCG GCGCCTACAT CTCCGGGAAC
     GCCACACGCG GCTTGGGCCA CTGAGGCCGC CGCGGATGTA GAGGCCCTTG

1051 CAGGCCCAGG GCGTGACCTC CGGCGGCTCG GGCAACTGCC GCACCGGTGG
     GTCCGGGTCC CGCACTGGAG GCCGCCGAGC CCGTTGACGG CGTGGCCACC

1101 CACCACCTAC CACCAGCCGA TCAACCCGCT GCTGGCACAG TGGAACCTGA
     GTGGTGGATG GTGGTCGGCT AGTTGGGCGA CGACCGTGTC ACCTTGGACT

1151 CCCTCGTGAC CACGGGCAAC GGCGGCGACC CGGGCGACCC CGGTGACCCG
     GGGAGCACTG GTGCCCGTTG CCGCCGCTGG GCCCGCTGGG GCCACTGGGC

1201 GGCGACCCGG GTGAGCCCGG CGGCAGCTGG TCCGCCGGGA CCAGTTACGC
     CCGCTGGGCC CACTCGGGCC GCCGTCGACC AGGCGGCCCT GGTCAATGCG

1251 GGTCGGCGAC CGGGTGACCT ACGGCGGCGC GGAGTACCGC TGCCTGCAGG
     CCAGCCGCTG GCCCACTGGA TGCCGCCGCG CCTCATGGCG ACGGACGTCC

1301 CCCACGTCGC CCAGTCCGGC TGGACGCCCC CGAACACGCC CGCCCTCTGG
     GGGTGCAGCG GGTCAGGCCG ACCTGCGGGG GCTTGTGCGG GCGGGAGACC

1351 CAGCGCGTGT GA
     GTCGCGCACA CT
```

SEQ ID NO:3 provides the polypeptide sequence of 1AG3 protease sequence is indicated by single underline, and the predicted mature chain is shown in bold.

```
  1 MHRRRGALFA GAVAIAALTI AAAPATAGPA LAPPEAQETA AQEIPAGMLQ  (SEQ ID NO: 3)

51 AMQRDLGLTE QQAEERVANE YQAGQLEPRL RAQLADTFAG SWTRGETAEL

101 VVATTDREQL PALTAAGVRA TVAEHSLSEL EAVKETLDEA AEEHATTEAP

151 VWYVDVTSNT VIVHAQDVTA GRDFVSAAGV DPAAVHVLRS DEQPRPYHDL

201 RGGEAYYMGS GGRCSVGFSV RRGTQAGFAT AGHCGRVGTT TRGFNQVAQG

251 TFQGSIFPGR DMGWVAVNSN WNTTPFVRGQ GGANVTVAGS QQAPVGSSVC

301 RSGSTTGWHC GTIQQHNTSV RYPEGTISGV TRTSVCAEPG DSGGAYISGN

351 QAQGVTSGGS GNCRTGGTTY HQPINPLLAQ WNLTLVTTGN GGDPGDPGDP

401 GDPGEPGGSW SAGTSYAVGD RVTYGGAEYR CLQAHVAQSG WTPPNTPALW

451 QRV
```

In SEQ ID NO:3, shown above, the predicted signal peptide is shown in double underline, while the predicted pro sequence is indicated by single underline, and the predicted mature chain is shown in bold.

SEQ ID NO:4 provides the polynucleotide sequence of the 1AG3 signal sequence:

```
 1 ATGCACCGCA GACGCGGAGC GCTATTCGCC GGCGCCGTGG CGATAGCCGC  (SEQ ID NO: 4)
   TACGTGGCGT CTGCGCCTCG CGATAAGCGG CCGCGGCACC GCTATCGGCG

51 CCTGACGATC GCCGCCGCGC CGGCC
   GGACTGCTAG CGGCGGCGCG GCCGG
```

SEQ ID NO:5 (MHRRRGALFA GAVAIAALTI AAAPA) is the polypeptide sequence corresponding to the signal sequence of SEQ ID NO:4.

SEQ ID NO:6 provides the polynucleotide sequence of the 1AG3 N-terminal prosequence:

```
  1 ACCGCCGGAC CGGCCCTCGC CCCGCCACCG GCCCAGGAGA CGGCGGCCCA   (SEQ ID NO: 6)
    TGGCGGCCTG GCCGGGAGCG GGGCGGTGGC CGGGTCCTCT GCCGCCGGGT

51 GGAGATCCCT GCCGGCATGC TGCAGGCCAT GCAGCGTGAT CTCGGCCTCA
    CCTCTAGGGA CGGCCGTACG ACGTCCGGTA CGTCGCACTA GAGCCGGAGT

101 CCGAGCAGCA GGCCGAGGAG CGCGTGGCCA ACGAGTACCA AGCGGGCCAG
    GGCTCGTCGT CCGGCTCCTC GCGCACCGGT TGCTCATGGT TCGCCCGGTC

151 CTGGAGCCAC GGCTGCGGGC GCAATTGGCG GACACCTTCG CCGGTTCCTG
    GACCTCGGTG CCGACGCCCG CGTTAACCGC CTGTGGAAGC GGCCAAGGAC

201 GACCAGGGGC GAGACCGCCG AGCTGGTCGT GGCCACCACC GACCGCGAGC
    CTGGTCCCCG CTCTGGCGGC TCGACCAGCA CCGGTGGTGG CTGGCGCTCG

251 AGCTACCGGC GCTGACGGCG GCGGGCGTGC GGGCCACCGT GGCCGAGCAC
    TCGATGGCCG CGACTGCCGC CGCCCGCACG CCCGGTGGCA CCGGCTCGTG

301 AGCCTGTCCG AGCTCGAGGC CGTGAAGGAG ACACTGGACG AGGCCGCCGA
    TCGGACAGGC TCGAGCTCCG GCACTTCCTC TGTGACCTGC TCCGGCGGCT

351 GGAGCACGCC ACGACCGAGG CGCCCGTGTG GTACGTGGAT GTCACGAGCA
    CCTCGTGCGG TGCTGGCTCC GCGGGCACAC CATGCACCTA CAGTGCTCGT

401 ACACGGTCAT CGTGCACGCC CAGGACGTGA CGGCCGGGCG CGACTTCGTC
    TGTGCCAGTA GCACGTGCGG GTCCTGCACT GCCGGCCCGC GCTGAAGCAG

451 TCGGCCGCGG GCGTGGACCC CGCCGCGGTC CACGTGCTGC GCTCGGACGA
    AGCCGGCGCC CGCACCTGGG GCGGCGCCAG GTGCACGACG CGAGCCTGCT

501 GCAGCCGCGG CCTTAC
    CGTCGGCGCC GGAATG
```

SEQ ID NO:7 provides the corresponding polypeptide sequence of the N-terminal prosequence set forth in SEQ ID NO:6.

```
  1 TAGPALAPPP AQETAAQEIP AGMLQAMQRD LGLTEQQAEE RVANEYQAGQ   (SEQ ID NO: 7)

51 LEPRLRAQLA DTFAGSWTRG ETAELVVATT DREQLPALTA AGVRATVAEH

101 SLSELEAVKE TLDEAAEEHA TTEAPVWYVD VTSNTVIVHA QDVTAGRDFV

151 SAAGVDPAAV HVLRSDEQPR PY
```

SEQ ID NO:8 provides the polynucleotide sequence encoding the mature protease sequence:

```
  1 CACGACCTGC GGGGTGGGGA GGCGTACTAC ATGGGCAGCG GAGGGCGCTG   (SEQ ID NO: 8)
    GTGCTGGACG CCCCACCCCT CCGCATGATG TACCCGTCGC CTCCCGCGAC

51 CTCGGTCGGC TTCTCCGTTC GCCGCGGAAC TCAGGCGGGC TTCGCGACCG
    GAGCCAGCCG AAGAGGCAAG CGGCGCCTTG AGTCCGCCCG AAGCGCTGGC

101 CGGGTCACTG CGGCCGGGTC GGCACCACCA CACGGGCTT CAACCAGGTG
    GCCCAGTGAC GCCGGCCCAG CCGTGGTGGT GTGCCCCGAA GTTGGTCCAC

151 GCGCAGGGCA CCTTCCAGGG CTCCATCTTC CCCGGGCGCG ACATGGGCTG
    CGCGTCCCGT GGAAGGTCCC GAGGTAGAAG GGGCCCGCGC TGTACCCGAC

201 GGTCGCGGTC AACTCCAACT GGAACACCAC CCCCTTCGTC CGCGGCCAGG
    CCAGCGCCAG TTGAGGTTGA CCTTGTGGTG GGGGAAGCAG GCGCCGGTCC

251 GGGGCGCGAA CGTGACGGTG GCGGGTTCGC AGCAGGCTCC GGTCGGCTCC
    CCCCGCGCTT GCACTGCCAC CGCCCAAGCG TCGTCCGAGG CCAGCCGAGG

301 TCGGTGTGCC GTTCCGGCTC CACCACCGGC TGGCACTGCG GCACCATCCA
    AGCCACACGG CAAGGCCGAG GTGGTGGCCG ACCGTGACGC CGTGGTAGGT
```

```
-continued
351 GCAGCACAAC ACCTCGGTGC GCTATCCGGA GGGCACCATC AGCGGAGTGA
    CGTCGTGTTG TGGAGCCACG CGATAGGCCT CCCGTGGTAG TCGCCTCACT 401 CCAGGACCTC GGTGTGCGCC GAACCCGGTG ACTCCGGCGG CGCCTACATC
    GGTCCTGGAG CCACACGCGG CTTGGGCCAC TGAGGCCGCC GCGGATGTAG 451 TCCGGGAACC AGGCCCAGGG CGTGACCTCC GGCGGCTCGG GCAACTGCCG
    AGGCCCTTGG TCCGGGTCCC GCACTGGAGG CCGCCGAGCC CGTTGACGGC 501 CACCGGTGGC ACCACCTACC ACCAGCCGAT CAACCCGCTG CTGGCACAGT
    GTGGCCACCG TGGTGGATGG TGGTCGGCTA GTTGGGCGAC GACCGTGTCA 551 GGAACCTGAC CCTCGTGACC ACGGGCAACG GCGGCGACCC GGGCGACCCC
    CCTTGGACTG GGAGCACTGG TGCCCGTTGC CGCCGCTGGG CCCGCTGGGG 601 GGTGACCCGG GCGACCCGGG TGAGCCCGGC GGCAGCTGGT CCGCCGGGAC
    CCACTGGGCC CGCTGGGCC ACTCGGGCCG CCGTCGACCA GGCGGCCCTG 651 CAGTTACGCG GTCGGCGACC GGGTGACCTA CGGCGGCGCG GAGTACCGCT
    GTCAATGCGC CAGCCGCTGG CCCACTGGAT GCCGCCGCGC CTCATGGCGA 701 GCCTGCAGGC CCACGTCGCC CAGTCCGGCT GGACGCCCCC GAACACGCCC
    CGGACGTCCG GGTGCAGCGG GTCAGGCCGA CCTGCGGGGG CTTGTGCGGG

751 GCCCTCTGGC AGCGCGTG
    CGGGAGACCG TCGCGCAC
```

SEQ ID NO:9, below, provides the amino acid sequence of the mature 1AG3 protease. In this sequence, the catalytic triad is shown in bold.

```
  1 HDLRGGEAYY MGSGGRCSVG FSVRRGTQAG FATAGHCGRV GTTTRGFNQV  (SEQ ID NO: 9)

51 AQGTFQGSIF PGRDMGWVAV NSNWNTTPFV RGQGGANVTV AGSQQAPVGS

101 SVCRSGSTTG WHCGTIQQHN TSVRYPEGTI SGVTRTSVCA EPGDSGGAYI

151 SGNQAQGVTS GGSGNCRTGG TTYHQPINPL LAQWNLTLVT TGNGGDPGDP

201 GDPGDPGEPG GSWSAGTSYA VGDRVTYGGA EYRCLQAHVA QSGWTPPNTP

251 ALWQRV
```

SEQ ID NO:10, below, provides the polynucleotide sequence of the 1AG3 precursor protease.

```
  1 ACCGCCGGAC CGGCCCTCGC CCCGCCACCG GCCCAGGAGA CGGCGGCCCA  (SEQ ID NO:
    TGGCGGCCTG GCCGGGAGCG GGGCGGTGGC CGGGTCCTCT GCCGCCGGGT         10)

51 GGAGATCCCT GCCGGCATGC TGCAGGCCAT GCAGCGTGAT CTCGGCCTCA
    CCTCTAGGGA CGGCCGTACG ACGTCCGGTA CGTCGCACTA GAGCCGGAGT

101 CCGAGCAGCA GGCCGAGGAG CGCGTGGCCA ACGAGTACCA AGCGGGCCAG
    GGCTCGTCGT CCGGCTCCTC GCGCACCGGT TGCTCATGGT TCGCCCGGTC

151 CTGGAGCCAC GGCTGCGGGC GCAATTGGCG GACACCTTCG CCGGTTCCTG
    GACCTCGGTG CCGACGCCCG CGTTAACCGC CTGTGGAAGC GGCCAAGGAC

201 GACCAGGGGC GAGACCGCCG AGCTGGTCGT GGCCACCACC GACCGCGAGC
    CTGGTCCCCG CTCTGGCGGC TCGACCAGCA CCGGTGGTGG CTGGCGCTCG

251 AGCTACCGGC GCTGACGGCG GCGGGCGTGC GGGCCACCGT GGCCGAGCAC
    TCGATGGCCG CGACTGCCGC CGCCCGCACG CCCGGTGGCA CCGGCTCGTG

301 AGCCTGTCCG AGCTCGAGGC CGTGAAGGAG ACACTGGACG AGGCCGCCGA
    TCGGACAGGC TCGAGCTCCG GCACTTCCTC TGTGACCTGC TCCGGCGGCT

351 GGAGCACGCC ACGACCGAGG CGCCCGTGTG GTACGTGGAT GTCACGAGCA
    CCTCGTGCGG TGCTGGCTCC GCGGGCACAC CATGCACCTA CAGTGCTCGT
```

```
                                -continued
 401 ACACGGTCAT CGTGCACGCC CAGGACGTGA CGGCCGGGCG CGACTTCGTC
     TGTGCCAGTA GCACGTGCGG GTCCTGCACT GCCGGCCCGC GCTGAAGCAG 451 TCGGCCGCGG GCGTGGACCC CGCCGCGGTC CACGTGCTGC GCTCGGACGA
     AGCCGGCGCC CGCACCTGGG GCGGCGCCAG GTGCACGACG CGAGCCTGCT 501 GCAGCCGCGG CCTTACCACG ACCTGCGGGG TGGGGAGGCG TACTACATGG
     CGTCGGCGCC GGAATGGTGC TGGACGCCCC ACCCCTCCGC ATGATGTACC 551 GCAGCGGAGG GCGCTGCTCG GTCGGCTTCT CCGTTCGCCG CGGAACTCAG
     CGTCGCCTCC CGCGACGAGC CAGCCGAAGA GGCAAGCGGC GCCTTGAGTC 601 GCGGGCTTCG CGACCGCGGG TCACTGCGGC CGGGTCGGCA CCACCACACG
     CGCCCGAAGC GCTGGCGCCC AGTGACGCCG GCCCAGCCGT GGTGGTGTGC 651 GGGCTTCAAC CAGGTGGCGC AGGGCACCTT CCAGGGCTCC ATCTTCCCCG
     CCCGAAGTTG GTCCACCGCG TCCCGTGGAA GGTCCCGAGG TAGAAGGGGC 701 GGCGCGACAT GGGCTGGGTC GCGGTCAACT CCAACTGGAA CACCACCCCC
     CCGCGCTGTA CCCGACCCAG CGCCAGTTGA GGTTGACCTT GTGGTGGGGG 751 TTCGTCCGCG GCCAGGGGGG CGCGAACGTG ACGGTGGCGG GTTCGCAGCA
     AAGCAGGCGC CGGTCCCCCC GCGCTTGCAC TGCCACCGCC CAAGCGTCGT 801 GGCTCCGGTC GGCTCCTCGG TGTGCCGTTC CGGCTCCACC ACCGGCTGGC
     CCGAGGCCAG CCGAGGAGCC ACACGGCAAG GCCGAGGTGG TGGCCGACCG 851 ACTGCGGCAC CATCCAGCAG CACAACACCT CGGTGCGCTA TCCGGAGGGC
     TGACGCCGTG GTAGGTCGTC GTGTTGTGGA GCCACGCGAT AGGCCTCCCG 901 ACCATCAGCG GAGTGACCAG GACCTCGGTG TGCGCCGAAC CCGGTGACTC
     TGGTAGTCGC CTCACTGGTC CTGGAGCCAC ACGCGGCTTG GGCCACTGAG 951 CGGCGGCGCC TACATCTCCG GGAACCAGGC CCAGGGCGTG ACCTCCGGCG
     GCCGCCGCGG ATGTAGAGGC CCTTGGTCCG GGTCCCGCAC TGGAGGCCGC 1001 GCTCGGGCAA CTGCCGCACC GGTGGCACCA CCTACCACCA GCCGATCAAC
     CGAGCCCGTT GACGGCGTGG CCACCGTGGT GGATGGTGGT CGGCTAGTTG 1051 CCGCTGCTGG CACAGTGGAA CCTGACCCTC GTGACCACGG GCAACGGCGG
     GGCGACGACC GTGTCACCTT GGACTGGGAG CACTGGTGCC CGTTGCCGCC 1101 CGACCCGGGC GACCCCGGTG ACCCGGGCGA CCCGGGTGAG CCCGGCGGCA
     GCTGGGCCCG CTGGGGCCAC TGGGCCCGCT GGGCCCACTC GGGCCGCCGT 1151 GCTGGTCCGC CGGGACCAGT TACGCGGTCG GCGACCGGGT GACCTACGGC
     CGACCAGGCG GCCCTGGTCA ATGCGCCAGC CGCTGGCCCA CTGGATGCCG 1201 GGCGCGGAGT ACCGCTGCCT GCAGGCCCAC GTCGCCCAGT CCGGCTGGAC
     CCGCGCCTCA TGGCGACGGA CGTCCGGGTG CAGCGGGTCA GGCCGACCTG 1251 GCCCCCGAAC ACGCCCGCCC TCTGGCAGCG CGTGTGA
     CGGGGGCTTG TGCGGGCGGG AGACCGTCGC GCACACT
```

SEQ ID NO:11, below, provides the amino acid sequence of the 1AG3 precursor protease:

```
  1 TAGPALAPPP AQETAAQEIP AGMLQAMQRD LGLTEQQAEE RVANEYQAGQ   (SEQ ID NO: 11)

51 LEPRLRAQLA DTFAGSWTRG ETAELVVATT DREQLPALTA AGVRATVAEH

101 SLSELEAVKE TLDEAAEEHA TTEAPVWYVD VTSNTVIVHA QDVTAGRDFV

151 SAAGVDPAAV HVLRSDEQPR PYHDLRGGEA YYMGSGGRCS VGFSVRRGTQ

201 AGFATAGHCG RVGTTTRGFN QVAQGTFQGS IFPGRDMGWV AVNSNWNTTP

251 FVRGQGGANV TVAGSQQAPV GSSVCRSGST TGWHCGTIQQ HNTSVRYPEG

301 TISGVTRTSV CAEPGDSGGA YISGNQAQGV TSGGSGNCRT GGTTYHQPIN

351 PLLAQWNLTL VTTGNGGDPG DPGDPGDPGE PGGSWSAGTS YAVGDRVTYG

401 GAEYRCLQAH VAQSGWTPPN TPALWQRV
```

SEQ ID NO:12, below, provides a partial polynucleotide sequence of the 16S rRNA gene sequence of strain 1AG3:

```
  1 GATCCTGGCT CAGGACGAAC GCTGGCGGCG TGCTTAACAC ATGCAAGTCG  (SEQ ID NO: 12)
    CTAGGACCGA GTCCTGCTTG CGACCGCCGC ACGAATTGTG TACGTTCAGC

51 AACGATGAAG CCGCTTCGGT GGTGGATTAG TGGCGAACGG GTGAGTAACA
    TTGCTACTTC GGCGAAGCCA CCACCTAATC ACCGCTTGCC CACTCATTGT

101 CGTGGGCAAT CTGCCCTGCA CTCTGGGACA AGCCCGGGAA ACTGGGTCTA
    GCACCCGTTA GACGGGACGT GAGACCCTGT TCGGGCCCTT TGACCCAGAT

151 ATACCGGATA TGACTGCTTC GGGCATCCGA GGTGGTGGAA AGCTCCGGCG
    TATGGCCTAT ACTGACGAAG CCCGTAGGCT CCACCACCTT TCGAGGCCGC

201 GTGCAGGATG GGCCCGCGGC CTATCAGCTT GTTGGTGGGG TGATGGCCTA
    CACGTCCTAC CCGGGCGCCG GATAGTCGAA CAACCACCCC ACTACCGGAT

251 CCAAGGCGAC GACGGGTAGC CGGCCTGAGA GGGCGACCGG CCACACTGGG
    GGTTCCGCTG CTGCCCATCG GCCGGACTCT CCCGCTGGCC GGTGTGACCC

301 ACTGAGACAC GGCCCAGACT CCTACGGGAG GCAGCAGTGG GGAATATTGC
    TGACTCTGTG CCGGGTCTGA GGATGCCCTC CGTCGTCACC CCTTATAACG

351 ACAATGGGCG CAAGCCTGAT GCAGCGACGC CGCGTGAGGG ATGACGGCCT
    TGTTACCCGC GTTCGGACTA CGTCGCTGCG GCGCACTCCC TACTGCCGGA

401 TCGGGTTGTA AACCTCTTTC AGCAGGGAAG AAGC
    AGCCCAACAT TTGGAGAAAG TCGTCCCTTC TTCG
```

In some additional embodiments, the present invention provides fragments or portions of DNA that encodes proteases, so long as the encoded fragment retains proteolytic activity. Another embodiment of the present invention encompasses polynucleotides having at least 20% of the sequence length, at least 30% of the sequence length, at least 40% of the sequence length, at least 50% of the sequence length, at least 60% of the sequence length, 70% of the sequence length, at least 75% of the sequence length, at least 80% of the sequence length, at least 85% of the sequence length, at least 90% of the sequence length, at least 92% of the sequence length, at least 95% of the sequence length, at least 97% of the sequence length, at least 98% of the sequence length and at least 99% of the sequence of the polynucleotide sequence of SEQ ID NOS:2, 8, 10 or 15. In some alternative embodiments, these fragments or portions of the sequence length are contiguous portions of the sequence length, useful for shuffling of the DNA sequence in recombinant DNA sequences (See e.g., U.S. Pat. No. 6,132,970, incorporated herein by reference).

Another embodiment of the invention includes fragments of the DNA described herein that find use according to art recognized techniques in obtaining partial length DNA fragments capable of being used to isolate or identify polynucleotides encoding mature protease enzyme described herein from *Streptomyces* 1AG3, or a segment thereof having proteolytic activity. Moreover, the DNA provided in SEQ ID NO:1 finds use in identifying homologous fragments of DNA from other species, and particularly from *Streptomyces* sp. which encode a protease or portion thereof having proteolytic activity.

In addition, the present invention encompasses using primer or probe sequences constructed from SEQ ID NO:1, or a suitable portion or fragment thereof (e.g., at least about 5-20 or 10-15 contiguous nucleotides), as a probe or primer for screening nucleic acid of either genomic or cDNA origin. In some embodiments, the present invention provides DNA probes of the desired length (i.e., generally between 100 and 1000 bases in length), based on the sequences set forth herein.

In some embodiments, the DNA fragments are electrophoretically isolated, cut from the gel, and recovered from the agar matrix of the gel. In some embodiments, this purified fragment of DNA is then labeled (using, for example, the Megaprime labeling system according to the instructions of the manufacturer) to incorporate $P^{32}$ in the DNA. The labeled probe is denatured by heating to 95° C. for a given period of time (e.g., 5 minutes), and immediately added to the membrane and prehybridization solution. The hybridization reaction proceeds for an appropriate time and under appropriate conditions (e.g., 18 hours at 37° C.), with gentle shaking or rotation. The membrane is rinsed (e.g., twice in SSC/0.3% SDS) and then washed in an appropriate wash solution with gentle agitation. The stringency desired is a reflection of the conditions under which the membrane (filter) is washed. In some embodiments herein, "low-strignency" conditions involve washing with a solution of 0.2×SSC/0.1% SDS at 20° C. for 15 minutes, while in other embodiments, "medium-stringency" conditions, involve a further washing step comprising washing with a solution of 0.2×SSC/0.1% SDS at 37° C. for 30 minutes, while in other embodiments, "high-stringency" conditions involve a further washing step comprising washing with a solution of 0.2×SSC/0.1% SDS at 37° C. for 45 minutes, and in further embodiments, "maximum-stringency" conditions involve a further washing step comprising washing with a solution of 0.2×SSC/0.1% SDS at 37° C. for 60 minutes. Thus, various embodiments of the present invention provide polynucleotides capable of hybridizing to a probe derived from the nucleotide sequence(s) provided herein, under conditions of medium, high and/or maximum stringency.

After washing, the membrane is dried and the bound probe detected. If $P^{32}$ or another radioisotope is used as the labeling agent, the bound probe is detected by autoradiography. Other techniques for the visualization of other probes are well-known to those of skill in the art. The detection of a bound probe indicates a nucleic acid sequence has the desired homology, and therefore identity to sequences set forth herein, and is encompassed by the present invention. Accordingly, the present invention provides methods for the detection of nucleic acid encoding a protease encompassed by the present invention which comprises hybridizing part or all of a nucleic acid sequences set forth herein, with other nucleic acid of either genomic or cDNA origin.

As indicated above, in other embodiments, hybridization conditions are based on the melting temperature (Tm) of the nucleic acid binding complex, to confer a defined "stringency" as explained below. "Maximum stringency" typically occurs at about Tm-5° C. (5° C. below the Tm of the probe); "high stringency" at about 5° C. to 10° C. below Tm; "intermediate stringency" at about 10° C. to 20° C. below Tm; and "low stringency" at about 20° C. to 25° C. below Tm. As known to those of skill in the art, medium, high and/or maximum stringency hybridization are chosen such that conditions are optimized to identify or detect polynucleotide sequence homologues or equivalent polynucleotide sequences.

In yet additional embodiments, the present invention provides nucleic acid constructs (i.e., expression vectors) comprising the polynucleotides encoding the proteases of the present invention. In further embodiments, the present invention provides host cells transformed with at least one of these vectors.

In some further embodiments, the present invention provides polynucleotide sequences further encoding a signal sequence (See, SEQ ID NO:4). In some embodiments, invention encompasses polynucleotides having signal activity comprising a nucleotide sequence having at least 65% sequence identity, at least 70% sequence identity, at least 75% sequence identity, more least 80% sequence identity, at least 85% sequence identity, at least 90% sequence identity, at least 95% sequence identity, at least 97% sequence identity, at least 98% sequence identity, and at least 99% sequence identity to SEQ ID NO:4. Thus, in these embodiments, the present invention provides a sequence with a putative signal sequence, and polynucleotides being capable of hybridizing to a probe derived from the nucleotide sequence disclosed in SEQ ID NO:4, under conditions of medium, high and/or maximal stringency, wherein the signal sequences have substantially the same signal activity as the signal sequence encoded by the polynucleotide of the present invention.

In some embodiments, the signal activity is indicated by substantially the same level of secretion of the protease into the fermentation medium, as the starting material. For example, in some embodiments, the present invention provides fermentation medium protease levels at least 50%, at least 60%, at least 70%, at least 80%, at least 90%, at least 95%, or at least 98% of the secreted protease levels in the fermentation medium as provided by the signal sequence of SEQ ID NO:4. In some embodiments, the secreted protease levels are ascertained by protease activity analyses such as the pNA assay (See e.g., Del Mar, [1979], infra). Additional means for determining the levels of secretion of a heterologous or homologous protein in a Gram-positive host cell and detecting secreted proteins include using either polyclonal or monoclonal antibodies specific for the protein. Examples include enzyme-linked immunosorbent assay (ELISA), radioimmunoassay (RIA) and fluorescent activated cell sorting (FACS), as well-known those in the art.

In some further embodiments, the present invention provides polynucleotides, encoding an amino acid sequence of a signal peptide (nucleotides 1-75 of SEQ ID NO:2), as shown in SEQ ID NO:4, nucleotide residue positions 1 to 75 of SEQ ID NO:2, and/or SEQ ID NO:4. The invention further encompasses nucleic acid sequences which hybridize to the nucleic acid sequence shown in SEQ ID NO:4 under low, medium, high stringency and/or maximum stringency conditions, but which have substantially the same signal activity as the sequence. The present invention encompasses all such polynucleotides. In some further embodiments, the present invention provides polynucleotides that are complementary to the nucleotide sequences described herein.

Further aspects of the present invention encompass polypeptides having proteolytic activity comprising 65% amino acid sequence identity, at least 70% sequence identity, at least 75% amino acid sequence identity, at least 80% amino acid sequence identity, at least 85% amino acid sequence identity, at least 90% amino acid sequence identity, at least 92% amino acid sequence identity, at least 95% amino acid sequence identity, at least 97% amino acid sequence identity, at least 98% amino acid sequence identity and at least 99% amino acid sequence identity to the amino acid sequence of SEQ ID NO:3 (i.e., the signal and precursor protease), SEQ ID NO:11 (i.e., the precursor protease), and/or of SEQ ID NO:9 (i.e., the mature protease). The proteolytic activity of these polypeptides is determined using methods known in the art and include such methods as those used to assess detergent function. In further embodiments, the polypeptides are isolated. In additional embodiments of the present invention, the polypeptides comprise amino acid sequences that are identical to amino acid sequence set forth herein. In some further embodiments, the polypeptides are identical to portions of the amino acid sequences set forth herein.

In some embodiments, the present invention provides isolated polypeptides having proteolytic activity, comprising the amino acid sequence approximately 453 amino acids in length, as provided in SEQ ID NO:3. In further embodiments, the present invention encompasses polypeptides having proteolytic activity comprising the amino acid sequence approximately 428 amino acids in length provided in SEQ ID NO:11. In some embodiments, these amino acid sequences comprise a signal sequence (amino acids 1-25 of SEQ ID NO:5); and a precursor protease (amino acids 1-428 of SEQ ID NO:11). In additional embodiments, the present invention encompasses polypeptides comprising an N-terminal prosequence (amino acids 1-172 of SEQ ID NO:7), a mature protease sequence (amino acids 1-256 of SEQ ID NO:9). In still further embodiments, the present invention encompasses polypeptides comprising a precursor protease sequence (e.g., amino acids 1-428 of SEQ ID NO:11). In yet another embodiment, the present invention encompasses polypeptides comprising a mature protease sequence comprising amino acids (e.g., 1-256 of SEQ ID NO:9).

In further embodiments, the present invention provides polypeptides and/or proteases comprising amino acid sequences of the above described sequence derived from bacterial species including, but not limited to Streptomycetaceae which are identified through amino acid sequence homology studies. In some embodiments, an amino acid residue of a precursor Streptomycetaceae protease is equivalent to a residue of *Streptomyces* strain 1AG3, if it is either homologous (i.e., corresponding in position in either primary or tertiary structure) or analogous to a specific residue or portion of that residue in *Streptomyces* strain 1AG3 protease (i.e., having the same or similar functional capacity to combine, react, or interact chemically).

In some embodiments, in order to establish homology to primary structure, the amino acid sequence of a precursor protease is directly compared to the *Streptomyces* strain 1AG3 mature protease amino acid sequence and particularly to a set of conserved residues which are discerned to be invariant in all or a large majority of *Streptomyces* like proteases for which sequence is known. After aligning the conserved residues, allowing for necessary insertions and deletions in order to maintain alignment (i.e., avoiding the elimination of conserved residues through arbitrary deletion and insertion), the residues corresponding to particular amino acids in the mature protease (SEQ ID NO:9) and *Streptomyces* 1AG3 protease are determined. Alignment of conserved residues should conserve 100% of such residues. However, alignment of greater than 75% or as little as 45% of conserved residues is also adequate to define equivalent residues. However, conservation of the catalytic triad, His36/Asp64/Ser145 of SEQ ID NO:9 should be maintained.

For example, in some embodiments, the amino acid sequence of proteases from *Streptomyces* strain 1AG3, and other Streptomycetaceae sp. described above are aligned to provide the maximum amount of homology between amino acid sequences. A comparison of these sequences indicates that there are a number of conserved residues contained in each sequence. These are the residues that are identified and utilized to establish the equivalent residue positions of amino acids identified in the precursor or mature Streptomycetaceae protease being analyzed.

These conserved residues are used to ascertain the corresponding amino acid residues of *Streptomyces* strain 1AG3 protease in one or more in Streptomycetaceae homologues These particular amino acid sequences are aligned with the sequence of *Streptomyces* 1AG3 protease to produce the maximum homology of conserved residues. By this alignment, the sequences and particular residue positions of *Streptomyces* 1AG3 are observed in comparison with other organisms (e.g., *Streptomyces* species.). Thus, the equivalent amino acid for the catalytic triad (e.g., in *Streptomyces* 1AG3 protease) is identifiable in the other Streptomycetaceae species. In some embodiments of the present invention, the protease homologs comprise the equivalent of His36/Asp64/Ser145 of SEQ ID NO:9.

Another indication that two polypeptides are substantially identical is that the first polypeptide is immunologically cross-reactive with the second polypeptide. Methodologies for determining immunological cross-reactivity are described in the art and are described in the Examples herein. Typically, polypeptides that differ by conservative amino acid substitutions are immunologically cross-reactive. Thus, a polypeptide is substantially identical to a second polypeptide, for example, where the two peptides differ only by a conservative substitution.

The present invention encompasses proteases obtained from various sources. In some embodiments, the proteases are obtained from bacteria, while in other embodiments, the proteases are obtained from fungi.

In some other aspects of the present invention, the polynucleotide is derived from a bacteria having a 16S rRNA gene nucleotide sequence at least 70%, 75%, 80%, 85%, 88%, 90%, 92%, 95%, 98% sequence identity with the (partial) 16S rRNA gene nucleotide sequence of *Streptomyces* strain 1AG3 (SEQ ID NO:12).

The strain 1AG3 exhibits the closest 16S rDNA relationship to members of *Streptomyces* of the family Streptomycetaceae. The closest relative is believed to be *Streptomyces somaliensis* (DSM40738) with at least 97% sequence identity with the 16S rRNA gene nucleotide sequence of *Streptomyces* strain 1AG3

In some embodiments of the present invention, the strain 69B4, as described in U.S. patent application Ser. No. 10/576,331, herein incorporated by reference in its entirety.

Although there may be variations in the sequence of a naturally occurring enzyme within a given species of organism, enzymes of a specific type produced by organisms of the same species generally are substantially identical with respect to substrate specificity and/or proteolytic activity levels under given conditions (e.g., temperature, pH, water hardness, oxidative conditions, chelating conditions, and concentration), etc. Thus, for the purposes of the present invention, it is contemplated that other strains and species of *Streptomyces* also produce the *Streptomyces* protease of the present invention and thus provide useful sources for the proteases of the present invention. Indeed, as presented herein, it is contemplated that other members of the Streptomycetaceae will find use in the present invention.

In some embodiments, the proteolytic polypeptides of this invention are characterized physicochemically, while in other embodiments, they are characterized based on their functionally, while in further embodiments, they are characterized using both sets of properties. Physicochemical characterization takes advantages of well known techniques such as SDS electrophoresis, gel filtration, amino acid composition, mass spectrometry (e.g., MALDI-TOF-MS, LC-ES-MS/MS, etc.), and sedimentation to determine the molecular weight of proteins, isoelectric focusing to determine the pI of proteins, amino acid sequencing to determine the amino acid sequences of protein, crystallography studies to determine the tertiary structures of proteins, and antibody binding to determine antigenic epitopes present in proteins.

In some embodiments, functional characteristics are determined by techniques well known to the practitioner in the protease field and include, but are not limited to, hydrolysis of various commercial substrates, such as di-methyl casein ("DMC") and/or AAPF-pNA. This technique for functional characterization is described in greater detail in the Examples provided herein.

In some embodiments of the present invention, the protease has a molecular weight of about 17 kD to about 22 kD, for example about 18 kD to 19 kD, for example 18700 daltons to 18800 daltons, for example about 18764 daltons, as determined by MALDI-TOF-MS). In another aspect of the present invention, the protease measured MALDI-TOF-MS spectrum as set forth in FIG. 3.

The mature protease also displays proteolytic activity (e.g., hydrolytic activity on a substrate having peptide linkages) such as DMC. In further embodiments, proteases of the present invention provide enhanced wash performance under identified conditions. Although the present invention encompasses the protease 1AG3 as described herein, in some embodiments, the proteases of the present invention exhibit at least 50%, 60%, 70%, 75%, 80%, 85%, 90%, 92%, 95%, 96%, 97%, 98% or 99% proteolytic activity as compared to the proteolytic activity of 1AG3. In some embodiments, the proteases display at least 50%, 60%, 70%, 75%, 80%, 85%, 90%, 92%, 95%, 96%, 97%, 98% or 99% proteolytic activity as compared to the proteolytic activity of proteases sold under the tradenames SAVINASE® (Novzymes) or PURAFECT® (Genencor) under the same conditions. In some embodiments, the proteases of the present invention display comparative or enhanced wash performance under identified conditions as compared to 1AG3 under the same conditions. In some embodiments, the proteases of the present invention display comparative or enhanced wash performance under identified conditions, as compared to proteases sold under the tradenames SAVINASE® (Novzymes) or PURAFECT® (Genencor) under the same conditions.

In yet further embodiments, the proteases and/or polynucleotides encoding the proteases of the present invention are provided purified form (i.e., present in a particular composition in a higher or lower concentration than exists in a naturally occurring or wild type organism), or in combination with components not normally present upon expression from a naturally occurring or wild-type organism. However, it is not intended that the present invention be limited to proteases of any specific purity level, as ranges of protease purity find use in various applications in which the proteases of the present invention are suitable.

As noted above, a recombinant polynucleotide comprising a nucleic acid encoding a subject protease is also provided. In certain embodiments, recombinant nucleic acid may contain an expression cassette comprising, in operable linkage: a promoter, a coding sequence encoding a subject protease, and a terminator sequence, where the expression cassette is sufficient for the production of the protease in a host cell. The promoter may be heterologous to the coding sequence.

In particular embodiments, the recombinant polynucleotide may further encode a signal sequence for directing the subject protease for secretion. In a particular embodiment, the recombinant nucleic acid may further contain a selectable marker for the selection of cells that contain the recombinant nucleic acid over other cells that do not contain the recombinant nucleic acid. Exemplary selectable markers include, but are not limited to, selectable markers that provide resistance to antibiotics, e.g., resistance to hygromycin, bleomycin, chloroamphenicol, phleomycin, kanamycin, streptomycin, ampicillin, tetracycline, etc.

In certain embodiments, the coding sequence may be codon optimized for expression of the fusion protein in the host cell used. Since codon usage tables listing the usage of each codon in many cells are known in the art (see, e.g., Nakamura et al, Nucl. Acids Res. 2000 28: 292) or readily derivable, such nucleic acids can be readily designed giving the amino acid sequence of a protein to be expressed.

A subject recombinant nucleic acid may be present, e.g., integrated, into a genome (i.e., the nuclear genome) of a host cell, or may be present in a vector, e.g., a phage, plasmid, viral, or retroviral vector, that autonomously replicates in the host cell. In certain embodiments, the vector may be an expression vector for expressing a protein in a host cell.

The choice of signal sequence, promoter and terminator largely depend on the host cell used. As noted above, in certain embodiments a *Streptomyces* host cell is employed, in which case the signal sequence may be a celA signal sequence. In certain cases, the celA signal sequence may be the signal sequence encoded by the *S. lividans* cellulase A gene, CelA, as described by Kluepfel et al. (Nature Biotechnol. 1996 14:756-759). In other embodiments in which a *Bacillus* host cell is employed, the signal sequence may be any sequence of amino acids that is capable of directing the fusion protein into the secretory pathway of the *Bacillus* host cell. In certain cases, signal sequences that may be employed include the signal sequences of proteins that are secreted from wild-type *Bacillus* cells. Such signal sequences include the signal sequences encoded by α-amylase, protease, e.g., aprE or subtilisin E, or β-lactamase genes. Exemplary signal sequences include, but are not limited to, the signal sequences encoded by an U-amylase gene, an subtilisin gene, an β-lactamase gene, an neutral protease gene (e.g., nprT, nprS, nprM), or a prsA gene from any suitable *Bacillus* species, including, but not limited to *B. stearothermophilus, B. licheniformis, B. licheniformis, B. subtilis* and *B. amyloliquefacien*. In one embodiment, the signal sequence is encoded by the aprE gene of *B. subtilis* (as described in Appl. Microbiol. Biotechnol. 2003 62:369-73). Further signal peptides are described by Simonen and Palva (Microbiological Reviews 1993 57: 109-137), and other references.

Suitable promoters and terminators for use in *Bacillus* and *Streptomyces* host cells are known and include: the promoters and terminators of apr (alkaline protease), npr (neutral protease), amy (α-amylase) and β-lactamase genes, as well as the *B. subtilis* levansucrase gene (sacB), *B. licheniformis* alpha-amylase gene (amyL), *B. stearothermophilus* maltogenic amylase gene (amyM), *B. amyloliquefaciens* alpha-amylase gene (amyQ), *B. licheniformis* penicillinase gene (penP), *B. subtilis* xylA and xylB genes, the promoters and terminators described in WO 93/10249, WO 98/07846, and WO 99/43835. Expression cassettes for use in *Streptomyces* host cells can be constructed using the promoters and terminators described in "Genetic Manipulation of *Streptomyces*: A Laboratory Manual" (Hopwood et al. Cold Spring Harbor Laboratories, 1985), Hopwood et al., (Hopwood et al., Regulation of Gene Expression in Antibiotic-producing *Streptomyces*. In Booth, I. and Higgins, C. (Eds) SYMPOSIUM OF THE SOCIETY FOR GENERAL MICROBIOLOGY, REGULATION OF GENE EXPRESSION, Cambridge University Press, 1986 pgs. 251-276), and in Fornwald et al (Proc. Natl. Acad. Sci. 1987 84: 2130-2134), Pulido et al (Gene. 1987 56:277-82); Dehottay et al (Eur. J. Biochem. 1987 166:345-50), Taguchi (Gene. 1989 84:279-86), Schmitt-John et al (Appl. Microbiol. Biotechnol. 1992 36:493-8), Motamedi (Gene 1995 160:25-31) and Binnie (Protein Expr. Purif. 1997 11:271-8), for example. In one embodiment, the A4 promoter may be employed, which promoter is described in WO 06/054997, which is incorporated by reference herein.

Vectors systems for expression of recombinant proteins in *Streptomyces, Bacillus, Aspergillus, Trichoderma* and other host cells are well known in the art and need not be discussed in any greater detail than that set forth above.

III. Obtaining Polynucleotides Encoding Streptomycetaceae (e.g., *Streptomyces*) Proteases of the Present Invention In some embodiments, nucleic acid encoding a protease of the present invention is obtained by standard procedures known in the art from, for example, cloned DNA (e.g., a DNA "library"), chemical synthesis, cDNA cloning, PCR, cloning of genomic DNA or fragments thereof, or purified from a desired cell, such as a bacterial or fungal species (See, for example, Sambrook et al., supra [1989]; and Glover and Hames (eds.), *DNA Cloning: A Practical Approach*, Vols 1 and 2, Second Edition). Synthesis of polynucleotide sequences is well known in the art (See e.g., Beaucage and Caruthers, Tetrahedron Lett., 22:1859-1862 [1981]), including the use of automated synthesizers (See e.g., Needham-VanDevanter et al., Nucl. Acids Res., 12:6159-6168 [1984]). DNA sequences can also be custom made and ordered from a variety of commercial sources. As described in greater detail herein, in some embodiments, nucleic acid sequences derived from genomic DNA contain regulatory regions in addition to coding regions.

In some embodiments involving the molecular cloning of the gene from genomic DNA, DNA fragments are generated, some of which comprise at least a portion of the desired gene. In some embodiments, the DNA is cleaved at specific sites using various restriction enzymes. In some alternative embodiments, DNAse is used in the presence of manganese to fragment the DNA, or the DNA is physically sheared (e.g., by sonication). The linear DNA fragments created are then be separated according to size and amplified by standard techniques, including but not limited to, agarose and polyacrylamide gel electrophoresis, PCR and column chromatography.

Once nucleic acid fragments are generated, identification of the specific DNA fragment encoding a protease may be accomplished in a number of ways. For example, in some embodiments, a proteolytic hydrolyzing enzyme encoding the 1AG3 gene or its specific RNA, or a fragment thereof, such as a probe or primer, is isolated, labeled, and then used in hybridization assays well known to those in the art, to detect a generated gene (See e.g., Benton and Davis, Science 196:180 [1977]; and Grunstein and Hogness, Proc. Natl. Acad. Sci. USA 72:3961 [1975]). In some embodiments, DNA fragments sharing substantial sequence similarity to the probe hybridize under medium to high stringency.

In some embodiments, amplification is accomplished using PCR, as known in the art. In some embodiments, a nucleic acid sequence of at least about 4 nucleotides and as many as about 60 nucleotides (i.e., fragments), e.g., about 12 to 30 nucleotides or about 25 nucleotides are used in any suitable combinations as PCR primer. These same fragments also find use as probes in hybridization and product detection methods.

In some embodiments, isolation of nucleic acid constructs of the invention from a cDNA or genomic library utilizes PCR with using degenerate oligonucleotide primers prepared on the basis of the amino acid sequence of the protein having the amino acid sequence as shown in SEQ ID NO:3 and/or 8. The primers can be of any segment length, for example at least 4, at least 5, at least 8, at least 15, at least 20, nucleotides in length. Exemplary probes in the present application utilized primers comprising sequence correspondings to TTGWH-CGT (SEQ ID NO:20)) and a GDSGG (SEQ ID NO:21) polynucleotide sequence as more fully described in Examples.

In view of the above, it will be appreciated that the polynucleotide sequences provided herein and based on the polynucleotide sequences provided herein are useful for obtaining identical or homologous fragments of polynucleotides from other species, and particularly from bacteria that encode enzymes having the serine protease activity expressed by protease 1AG3.

IV. Expression and Recovery of Serine Proteases of the Present Invention

Any suitable means for expression and recovery of the serine proteases of the present invention find use herein. Indeed, those of skill in the art know many methods suitable for cloning a *Streptomyces*-derived polypeptide having proteolytic activity, as well as an additional enzyme (e.g., a second peptide having proteolytic activity, such as a protease, cellulase, mannanase, or amylase, etc.). Numerous methods are also known in the art for introducing at least one (e.g., multiple) copies of the polynucleotide(s) encoding the enzyme(s) of the present invention in conjunction with any additional sequences desired, into the genes or genome of host cells.

In general, standard procedures for cloning of genes and introducing exogenous proteases encoding regions (including multiple copies of the exogenous encoding regions) into said genes find use in obtaining a *Streptomyces* 1AG3 protease derivative or homologue thereof. Indeed, the present Specification, including the Examples provides such teaching. However, additional methods known in the art are also suitable (See e.g., Sambrook et al. supra (1989); Ausubel et al., supra [1995]; and Harwood and Cutting, (eds.) *Molecular Biological Methods for Bacillus*," John Wiley and Sons, [1990]; and WO 96/34946).

In some embodiments, the polynucleotide sequences of the present invention are expressed by operatively linking them to an expression control sequence in an appropriate expression vector and employed by that expression vector to transform an appropriate host according to techniques well established in the art. In some embodiments, the polypeptides produced on expression of the DNA sequences of this invention are isolated from the fermentation of cell cultures and purified in a variety of ways according to well established techniques in the art. Those of skill in the art are capable of selecting the most appropriate isolation and purification techniques.

More particularly, the present invention provides constructs, vectors comprising polynucleotides described herein, host cells transformed with such vectors, proteases expressed by such host cells, expression methods and systems for the production of serine protease enzymes derived from microorganisms, in particular, members of the Streptomycetaceae, including but not limited to *Streptomyces* species. In some embodiments, the polynucleotide(s) encoding serine protease (s) are used to produce recombinant host cells suitable for the expression of the serine protease(s). In some embodiments, the expression hosts are capable of producing the protease(s) in commercially viable quantities.

IV. Recombinant Vectors

As indicated above, in some embodiments, the present invention provides vectors comprising the aforementioned polynucleotides. In some embodiments, the vectors (i.e., constructs) of the invention encoding the protease are of genomic origin (e.g., prepared though use of a genomic library and screening for DNA sequences coding for all or part of the protease by hybridization using synthetic oligonucleotide probes in accordance with standard techniques). In some embodiments, the DNA sequence encoding the protease is obtained by isolating chromosomal DNA from the *Streptomyces* strain 1AG3 and amplifying the sequence by PCR methodology (See, the Examples).

In alternative embodiments, the nucleic acid construct of the invention encoding the protease is prepared synthetically by established standard methods (See e.g., Beaucage and Caruthers, Tetra. Lett. 22:1859-1869 [1981]; and Matthes et al., EMBO J., 3:801-805 [1984]). According to the phosphoramidite method, oligonucleotides are synthesized (e.g., in an automatic DNA synthesizer), purified, annealed, ligated and cloned in suitable vectors.

In additional embodiments, the nucleic acid construct is of mixed synthetic and genomic origin. In some embodiments, the construct is prepared by ligating fragments of synthetic or genomic DNA (as appropriate), wherein the fragments correspond to various parts of the entire nucleic acid construct, in accordance with standard techniques.

In further embodiments, the present invention provides vectors comprising at least one DNA construct of the present invention. In some embodiments, the present invention encompasses recombinant vectors. It is contemplated that any suitable vector will find use in the present invention, including autonomously replicating vector a well as vectors that integrate (either transiently or stably) within the host cell genome). Indeed, a wide variety of vectors, and expression cassettes suitable for the cloning, transformation and expression in fungal (mold and yeast), bacterial, insect and plant cells are known to those of skill in the art. Typically, the vector or cassette contains sequences directing transcription and translation of the nucleic acid, a selectable marker, and sequences allowing autonomous replication or chromosomal integration. In some embodiments, suitable vectors comprise a region 5' of the gene which harbors transcriptional initiation controls and a region 3' of the DNA fragment which controls transcriptional termination. These control regions may be derived from genes homologous or heterologous to the host as long as the control region selected is able to function in the host cell.

The vector may be an expression vector in which the DNA sequence encoding the protease of the invention is operably linked to additional segments required for transcription of the DNA. In some embodiments, the expression vector is derived from plasmid or viral DNA, or in alternative embodiments, contains elements of both. Exemplary vectors include, but are not limited to pSEA4C, pSEGCT, pSEACT, and/or pSEA4CT, as well as all of the vectors described in the Examples herein. Construction of such vectors is described herein, and methods are well known in the art (See e.g., U.S. Pat. No. 6,287,839; and WO 02/50245). In some embodiments, the vector pSEA4C described herein finds use in the construction of a vector comprising the polynucleotides described herein (e.g., pSEA4CT-1AG3). Indeed, it is intended that all of the vectors described herein will find use in the present invention.

In some embodiments, the additional segments required for transcription include regulatory segments (e.g., promoters, secretory segments, inhibitors, global regulators, etc.), as known in the art. One example includes any DNA sequence that shows transcriptional activity in the host cell of choice and is derived from genes encoding proteins either homologous or heterologous to the host cell. Specifically, examples of suitable promoters for use in bacterial host cells include but are not limited to the promoter of the *Bacillus stearothermophilus* maltogenic amylase gene, the *Bacillus amyloliquefaciens* (BAN) amylase gene, the *Bacillus subtilis* alkaline protease gene, the *Bacillus clausii* alkaline protease gene the *Bacillus pumilus* xylosidase gene, the *Bacillus thuringiensis* cryIIIA, and the *Bacillus licheniformis* alpha-amylase gene. Additional promoters include the A4 promoter, as described herein. Other promoters that find use in the present invention include, but are not limited to phage Lambda $P_R$ or $P_L$ promoters, as well as the *E. coli* lac, trp or tac promoters.

In some embodiments, the promoter is derived from a gene encoding the protease or a fragment thereof having substantially the same promoter activity as said sequence. The invention further encompasses nucleic acid sequences which hybridize to the promoter sequences under intermediate, high, and/or maximum stringency conditions, or which have at least about 90% homology and about 95% homology to such promoter, but which have substantially the same promoter activity. In some embodiments, this promoter is used to promote the expression of either the protease and/or a heterologous DNA sequence (e.g., another enzyme in addition to the protease of the present invention). In additional embodiments, the vector also comprises at least one selectable marker.

In some embodiments, the recombinant vectors of the invention further comprise a DNA sequence enabling the vector to replicate in the host cell. In some embodiments involving bacterial host cells, these sequences comprise all the sequences needed to allow plasmid replication (e.g., ori and/or rep sequences).

In some particular embodiments, signal sequences (e.g., leader sequence or pre sequence) are also included in the vector, in order to direct a polypeptide of the present invention into the secretory pathway of the host cells. In some embodiments, a secretory signal sequence is joined to the DNA sequence encoding the precursor protease in the correct reading frame. Depending on whether the protease is to be expressed intracellularly or is secreted, a polynucleotide sequence or expression vector of the invention is engineered with or without a natural polypeptide signal sequence or a signal sequence which functions in bacteria (e.g., *Bacillus* sp.), fungi (e.g., *Trichoderma*), other prokaryotes or eukaryotes. In some embodiments, expression is achieved by either removing or partially removing the signal sequence In some embodiments involving secretion from bacterial cells, the signal peptide is a naturally occurring signal peptide, or a functional part thereof, while in other embodiments, it is a synthetic peptide. Suitable signal peptides include but are not limited to sequences derived from *Bacillus licheniformis* alpha-amylase, *Bacillus clausii* alkaline protease, and *Bacillus amyloliquefaciens* amylase. One signal sequence is the signal peptide derived from *Streptomyces* strain 1AG3, as described herein. Thus, in some particular embodiments, the signal peptide comprises the signal peptide from the protease described herein. This signal finds use in facilitating the secretion of the 1AG3 protease and/or a heterologous DNA sequence (e.g. a second protease, such as another wild-type protease, a BPN' variant protease, a GG36 variant protease, a lipase, a cellulase, a mannanases, etc.). In some embodiments, these second enzymes are encoded by the DNA sequence and/or the amino acid sequences known in the art (See e.g., U.S. Pat. Nos. 6,465,235, 6,287,839, 5,965,384, and 5,795,764; as well as WO 98/22500, WO 92/05249, EP 0305216B1, and WO 94/25576). Furthermore, it is contemplated that in some embodiments, the signal sequence peptide is also be operatively linked to an endogenous sequence to activate and secrete such endogenous encoded protease.

The procedures used to ligate the DNA sequences coding for the present protease, the promoter and/or secretory signal sequence, respectively, and to insert them into suitable vectors containing the information necessary for replication, are well known to those skilled in the art. As indicated above, in some embodiments, the nucleic acid construct is prepared using PCR with specific primers.

V. Host Cells

As indicated above, in some embodiments, the present invention also provides host cells transformed with the vectors described above. In some embodiments, the polynucleotide encoding the protease(s) of the present invention that is introduced into the host cell is homologous, while in other embodiments, the polynucleotide is heterologous to the host. In some embodiments in which the polynucleotide is homologous to the host cell (e.g., additional copies of the native protease produced by the host cell are introduced), it is operably connected to another homologous or heterologous promoter sequence. In alternative embodiments, another secretory signal sequence, and/or terminator sequence find use in the present invention. Thus, in some embodiments, the polypeptide DNA sequence comprises multiple copies of a homologous polypeptide sequence, a heterologous polypeptide sequence from another organism, or synthetic polypeptide sequence(s). Indeed, it is not intended that the present invention be limited to any particular host cells and/or vectors.

Indeed, the host cell into which the DNA construct of the present invention is introduced may be any cell which is capable of producing the present alkaline protease, including, but not limited to bacteria, fungi, and higher eukaryotic cells.

Examples of bacterial host cells which find use in the present invention include, but are not limited to Gram-positive bacteria such as *Bacillus*, *Streptomyces*, and *Thermobifida*, for example strains of *B. subtilis*, *B. licheniformis*, *B. lentus*, *B. brevis*, *B. stearothermophilus*, *B. clausii*, *B. amyloliquefaciens*, *B. coagulans*, *B. circulans*, *B. lautus*, *B. megaterium*, *B. thuringiensis*, *S. griseus*, *S. lividans*, *S. coelicolor*; *S. avermitilis* and *T. fusca*; as well as Gram-negative bacteria such as members of the Enterobacteriaceae (e.g., *Escherichia coli*). In some embodiments, the host cells are *B. subtilis*, *B. clausii*, and/or *B. licheniformis*. In additional embodiments, the host cells are strains of *S. lividans* (e.g., TK23 and/or TK21). Any suitable method for transformation of the bacteria find use in the present invention, including but not limited to protoplast transformation, use of competent cells, etc., as known in the art. In some embodiments, the method provided in U.S. Pat. No. 5,264,366 (incorporated by reference herein), finds used in the present invention. For *S. lividans*, one means for transformation and protein expression is that described by Fernandez-Abalos et al. (See, Fernandez-Abalos et al., Microbiol., 149:1623-1632 [2003]; See also, Hopwood, et al., Genetic Manipulation of *Streptomyces:* Laboratory Manual, Innis [1985], both of which are incorporated by reference herein). Of course, the methods described in the Example herein find use in the present invention.

Examples of fungal host cells which find use in the present invention include, but are not limited to *Trichoderma* species. and Aspergillus species. In some particular embodiments, the host cells are *Trichoderma reesei* and/or *Aspergillus niger*. In some embodiments, transformation and expression in *Aspergillus* is performed as described in U.S. Pat. No. 5,364, 770, herein incorporated by reference. Of course, the methods described in the Example herein find use in the present invention.

In some embodiments, particular promoter and signal sequences are needed to provide effective transformation and expression of the protease(s) of the present invention. Thus, in some embodiments involving the use of *Bacillus* host cells, the aprE promoter is used in combination with known *Bacillus*-derived signal and other regulatory sequences. In some embodiments involving expression in *Aspergillus*, the glaA promoter is used. In some embodiments involving *Streptomyces* host cells, the glucose isomerase (GI) promoter of *Actinoplanes missouriensis* is used, while in other embodiments, the A4 promoter is used.

In some embodiments involving expression in bacteria such as *E. coli*, the protease is retained in the cytoplasm, typically as insoluble granules (i.e., inclusion bodies). However, in other embodiments, the protease is directed to the periplasmic space by a bacterial secretion sequence. In the former case, the cells are lysed, and the granules are recovered and denatured after which the protease is refolded by diluting the denaturing agent. In the latter case, the protease is recovered from the periplasmic space by disrupting the cells (e.g., by sonication or osmotic shock), to release the contents of the periplasmic space and recovering the protease.

In some embodiments, the transformed host cells of the present invention are cultured in a suitable nutrient medium under conditions permitting the expression of the present protease, after which the resulting protease is recovered from the culture. The medium used to culture the cells comprises any conventional medium suitable for growing the host cells, such as minimal or complex media containing appropriate supplements. Suitable media are available from commercial suppliers or may be prepared according to published recipes (e.g., in catalogues of the American Type Culture Collection). In some embodiments, the protease produced by the cells is recovered from the culture medium by conventional procedures, including, but not limited to separating the host cells from the medium by centrifugation or filtration, precipitating the proteinaceous components of the supernatant or filtrate by means of a salt (e.g., ammonium sulfate), chromatographic purification (e.g., ion exchange, gel filtration, affinity, etc.). Thus, any method suitable for recovering the protease(s) of the present invention will find use. Indeed, it is not intended that the present invention be limited to any particular purification method.

VI. Applications for Serine Protease Enzymes

As described in greater detail herein, the proteases of the present invention have important characteristics that make them very suitable for certain applications. For example, the proteases of the present invention have enhanced thermal stability, enhanced oxidative stability, and enhanced chelator stability, as compared to some currently used proteases. Thus, these proteases find use in cleaning compositions. Indeed, under certain wash conditions, the present proteases exhibit comparative or enhanced wash performance as compared with currently used subtilisin proteases. Thus, it is contemplated that the cleaning and/or enzyme compositions of the present invention will be provided in a variety of cleaning compositions. In some embodiments, the proteases of the present invention are utilized in the same manner as subtilisin proteases (i.e., proteases currently in use). Thus, the present proteases find use in various cleaning compositions, as well as animal feed applications, leather processing (e.g., bating), protein hydrolysis, and in textile uses. The identified proteases also find use in personal care applications.

Thus, the proteases of the present invention find use in a number of industrial applications, in particular within the cleaning, disinfecting, animal feed, and textile/leather industries. In some embodiments, the protease(s) of the present invention are combined with detergents, builders, bleaching agents and other conventional ingredients to produce a variety of novel cleaning compositions useful in the laundry and other cleaning arts such as, for example, laundry detergents (both powdered and liquid), laundry pre-soaks, all fabric bleaches, automatic dishwashing detergents (both liquid and powdered), household cleaners, particularly bar and liquid soap applications, and drain cleaners/openers. In addition, the protease finds use in the cleaning of contact lenses, as well as other items, by contacting such materials with an aqueous solution of the cleaning composition. In addition these naturally occurring proteases can be used, for example in peptide hydrolysis, waste treatment, textile applications, medical device cleaning, biofilm removal and as fusion-cleavage enzymes in protein production, etc. The composition of these products is not critical to the present invention, as long as the protease(s) maintain their function in the setting used. In some embodiments, the compositions are readily prepared by combining a cleaning effective amount of the protease or an enzyme composition comprising the protease enzyme preparation with the conventional components of such compositions in their art recognized amounts.

The proteases of the present invention find particular use in the cleaning industry, including, but not limited to laundry and dish detergents. These applications place enzymes under various environmental stresses. The proteases of the present invention provide advantages over many currently used enzymes, due to their stability under various conditions.

Indeed, there are a variety of wash conditions including varying detergent formulations, wash water volumes, wash water temperatures, and lengths of wash time, to which proteases involved in washing are exposed. In addition, detergent formulations used in different geographical areas have different concentrations of their relevant components present in the wash water. For example, a European detergent typically has about 4500-5000 ppm of detergent components in the wash water, while a Japanese detergent typically has approximately 667 ppm of detergent components in the wash water. In North America, particularly the United States, detergents typically have about 975 ppm of detergent components present in the wash water.

A low detergent concentration system includes detergents where less than about 800 ppm of detergent components are present in the wash water. Japanese detergents are typically considered low detergent concentration system as they have approximately 667 ppm of detergent components present in the wash water.

A medium detergent concentration includes detergents where between about 800 ppm and about 2000 ppm of detergent components are present in the wash water. North American detergents are generally considered to be medium detergent concentration systems as they have approximately 975 ppm of detergent components present in the wash water. Brazil typically has approximately 1500 ppm of detergent components present in the wash water.

A high detergent concentration system includes detergents where greater than about 2000 ppm of detergent components are present in the wash water. European detergents are generally considered to be high detergent concentration systems as they have approximately 4500-5000 ppm of detergent components in the wash water.

Latin American detergents are generally high suds phosphate builder detergents and the range of detergents used in Latin America can fall in both the medium and high detergent concentrations as they range from 1500 ppm to 6000 ppm of detergent components in the wash water. As mentioned above, Brazil typically has approximately 1500 ppm of detergent components present in the wash water. However, other high suds phosphate builder detergent geographies, not limited to other Latin American countries, may have high detergent concentration systems up to about 6000 ppm of detergent components present in the wash water.

In light of the foregoing, it is evident that concentrations of detergent compositions in typical wash solutions throughout the world varies from less than about 800 ppm of detergent composition ("low detergent concentration geographies"), for example about 667 ppm in Japan, to between about 800 ppm to about 2000 ppm ("medium detergent concentration geographies"), for example about 975 ppm in U.S. and about 1500 ppm in Brazil, to greater than about 2000 ppm ("high detergent concentration geographies"), for example about 4500 ppm to about 5000 ppm in Europe and about 6000 ppm in high suds phosphate builder geographies.

The concentrations of the typical wash solutions are determined empirically. For example, in the U.S., a typical washing machine holds a volume of about 64.4 L of wash solution. Accordingly, in order to obtain a concentration of about 975 ppm of detergent within the wash solution about 62.79 g of detergent composition must be added to the 64.4 L of wash solution. This amount is the typical amount measured into the wash water by the consumer using the measuring cup provided with the detergent.

As a further example, different geographies use different wash temperatures. The temperature of the wash water in Japan is typically less than that used in Europe. For example, the temperature of the wash water in North America and Japan can be between 10 and 30° C. (e.g., about 20° C.), whereas the temperature of wash water in Europe is typically between 30 and 60° C. (e.g., about 40° C.).

As a further example, different geographies typically have different water hardness. Water hardness is usually described in terms of the grains per gallon mixed $Ca^{2+}/Mg^{2+}$. Hardness is a measure of the amount of calcium ($Ca^{2+}$) and magnesium ($Mg^{2+}$) in the water. Most water in the United States is hard, but the degree of hardness varies. Moderately hard (60-120 ppm) to hard (121-181 ppm) water has 60 to 181 parts per million (parts per million converted to grains per U.S. gallon is ppm # divided by 17.1 equals grains per gallon) of hardness minerals.

| Water | Grains Per Gallon | Parts Per Million |
|---|---|---|
| Soft | less than 1.0 | less than 17 |
| Slightly hard | 1.0 to 3.5 | 17 to 60 |
| Moderately hard | 3.5 to 7.0 | 60 to 120 |
| Hard | 7.0 to 10.5 | 120 to 180 |
| Very hard | greater than 10.5 | greater than 180 |

European water hardness is typically greater than 10.5 (for example 10.5-20.0) grains per gallon mixed $Ca^{2+}/Mg^{2+}$ (e.g., about 15 grains per gallon mixed $Ca^{2+}/Mg^{2+}$). North American water hardness is typically greater than Japanese water hardness, but less than European water hardness. For example, North American water hardness can be between 3 to 10 grains, 3-8 grains or about 6 grains. Japanese water hardness is typically lower than North American water hardness, usually less than 4, for example 3 grains per gallon mixed $Ca^{2+}/Mg^{2+}$.

Accordingly, in some embodiments, the present invention provides proteases that show surprising wash performance in at least one set of wash conditions (e.g., water temperature, water hardness, and/or detergent concentration). In some embodiments, the proteases of the present invention are comparable in wash performance to subtilisin proteases. In some embodiments, the proteases of the present invention exhibit enhanced wash performance as compared to subtilisin proteases. Thus, in some embodiments of the present invention, the proteases provided herein exhibit enhanced oxidative stability, enhanced thermal stability, and/or enhanced chelator stability.

In some embodiments, the present invention provides the 1AG3 protease, as well as homologues and variants for the protease. These proteases find use in any applications in which it is desired to clean protein based stains from textiles or fabrics.

In some embodiments, the cleaning compositions of the present invention are formulated as hand and machine laundry detergent compositions including laundry additive compositions, and compositions suitable for use in the pretreatment of stained fabrics, rinse-added fabric softener compositions, and compositions for use in general household hard surface cleaning operations, as well as dishwashing operations. Those in the art are familiar with different formulations which can be used as cleaning compositions. In some embodiments, the proteases of the present invention comprise comparative or enhanced performance in detergent compositions (i.e., as compared to other proteases). In some embodiments, cleaning performance is evaluated by comparing the proteases of the present invention with subtilisin proteases in various cleaning assays that utilize enzyme-sensitive stains such as egg, grass, blood, milk, etc., in standard methods. Indeed, those in the art are familiar with the spectrophotometric and other analytical methodologies used to assess detergent performance under standard wash cycle conditions.

Assays that find use in the present invention include, but are not limited to those described in WO 99/34011, and U.S. Pat. No. 6,605,458 (See e.g., Example 3). In U.S. Pat. No. 6,605,458, at Example 3, a detergent dose of 3.0 g/l at pH10.5, wash time 15 minutes, at 15 C, water hardness of 6° dH, 10 nM enzyme concentration in 150 ml glass beakers with stirring rod, 5 textile pieces (phi 2.5 cm) in 50 ml, EMPA 117 test material from Center for Test Materials Holland are used. The measurement of reflectance "R" on the test material was done at 460 nm using a Macbeth ColorEye 7000 photometer. Additional methods are provided in the Examples herein. Thus, these methods also find use in the present invention.

The addition of proteases of the invention to conventional cleaning compositions does not create any special use limitation. In other words, any temperature and pH suitable for the detergent is also suitable for the present compositions, as long as the pH is within the range set forth herein, and the temperature is below the described protease's denaturing temperature. In addition, proteases of the present invention find use in cleaning compositions that do not include detergents, again either alone or in combination with builders and stabilizers.

When used in cleaning compositions or detergents, oxidative stability is a further consideration. Thus, in some applications, the stability is enhanced, diminished, or comparable to subtilisin proteases as desired for various uses. In some embodiments, enhanced oxidative stability is desired. Some of the proteases of the present invention find particular use in such applications.

When used in cleaning compositions or detergents, thermal stability is a further consideration. Thus, in some applications, the stability is enhanced, diminished, or comparable to subtilisin proteases as desired for various uses. In some embodiments, enhanced thermostability is desired. Some of the proteases of the present invention find particular use in such applications.

When used in cleaning compositions or detergents, chelator stability is a further consideration. Thus, in some applications, the stability is enhanced, diminished, or comparable to subtilisin proteases as desired for various uses. In some embodiments, enhanced chelator stability is desired. Some of the proteases of the present invention find particular use in such applications.

In some embodiments of the present invention, naturally occurring proteases are provided which exhibit modified enzymatic activity at different pHs when compared to subtilisin proteases. A pH-activity profile is a plot of pH against enzyme activity and may be constructed as described in the Examples and/or by methods known in the art. In some embodiments, it is desired to obtain naturally occurring proteases with broader profiles (i.e., those having greater activity at range of pHs than a comparable subtilisin protease). In other embodiments, the enzymes have no significantly greater activity at any pH, or naturally occurring homologues with sharper profiles (i.e., those having enhanced activity when compared to subtilisin proteases at a given pH, and lesser activity elsewhere). Thus, in various embodiments, the proteases of the present invention have differing pH optima and/or ranges. It is not intended that the present invention be limited to any specific pH or pH range.

In some embodiments of the present invention, the cleaning compositions comprise, proteases of the present invention at a level from 0.00001% to 10% of 1AG3 and/or other protease of the present invention by weight of the composition and the balance (e.g., 99.999% to 90.0%) comprising cleaning adjunct materials by weight of composition. In other aspects of the present invention, the cleaning compositions of the present invention comprise, the 1AG3 and/or other proteases at a level of 0.0001% to 10%, 0.001% to 5%, 0.001% to 2%, 0.005% to 0.5% 69B4 or other protease of the present invention by weight of the composition and the balance of the cleaning composition (e.g., 99.9999% to 90.0%, 99.999% to 98%, 99.995% to 99.5% by weight) comprising cleaning adjunct materials.

In some embodiments, cleaning compositions, in addition to the protease preparation of the invention, comprise one or more additional enzymes or enzyme derivatives which provide cleaning performance and/or fabric care benefits. Such enzymes include, but are not limited to other proteases, lipases, cutinases, amylases, cellulases, peroxidases, oxidases (e.g. laccases), and/or mannanases.

Any other protease suitable for use in alkaline solutions finds use in the compositions of the present invention. Suitable proteases include those of animal, vegetable or microbial origin. In particular embodiments, microbial proteases are used. In some embodiments, chemically or genetically modified mutants are included. In some embodiments, the protease is a serine protease, an alkaline microbial protease or a trypsin-like protease. Examples of alkaline proteases include subtilisins, especially those derived from *Bacillus* (e.g., subtilisin, *lentus, amyloliquefaciens*, subtilisin Carlsberg, subtilisin 309, subtilisin 147 and subtilisin 168). Additional examples include those mutant proteases described in U.S. Pat. Nos. RE 34,606, 5,955,340, 5,700,676, 6,312,936, and 6,482,628, all of which are incorporated herein by reference. Additional protease examples include, but are not limited to trypsin (e.g., of porcine or bovine origin), and the Fusarium protease described in WO 89/06270. Commercially available protease enzymes include those sold under the trade names MAXATASE®, MAXACAL™, MAXAPEM™, OPTI-CLEAN®, OPTIMASE®, PROPERASE®, PURAFECT® and PURAFECT® OXP (Genencor), those sold under the trade names ALCALASE®, SAVINASE®, PRIMASE®, DURAZYM™, RELASE® and ESPERASE® (Novozymes); and those sold under the trade name BLAP™ (Henkel Kommanditgesellschaft auf Aktien, Duesseldorf, Germany. Various proteases are described in WO95/23221, WO 92/21760, and U.S. Pat. Nos. 5,801,039, 5,340,735, 5,500,364, 5,855,625. An additional BPN' variant ("BPN'-var 1" and "BPN-variant 1"; as referred to herein) is described in U.S. RE 34,606. An additional GG36-variant ("GG36-var.1" and "GG36-variant 1"; as referred to herein) is described in U.S. Pat. Nos. 5,955,340 and 5,700,676. A further GG36-variant is described in U.S. Pat. Nos. 6,312,936 and 6,482,628. In one aspect of the present invention, the cleaning compositions of the present invention comprise additional protease enzymes at a level from 0.00001% to 10% of additional protease by weight of the composition and 99.999% to 90.0% of cleaning adjunct materials by weight of composition. In other embodiments of the present invention, the cleaning compositions of the present invention also comprise, proteases at a level of 0.0001% to 10%, 0.001% to 5%, 0.001% to 2%, 0.005% to 0.5% 69B4 protease (or its homologues or variants) by weight of the composition and the balance of the cleaning composition (e.g., 99.9999% to 90.0%, 99.999% to 98%, 99.995% to 99.5% by weight) comprising cleaning adjunct materials.

In addition, any lipase suitable for use in alkaline solutions finds use in the present invention. Suitable lipases include, but are not limited to those of bacterial or fungal origin. Chemically or genetically modified mutants are encompassed by the present invention. Examples of useful lipases include Humicola lanuginosa lipase (See e.g., EP 258 068, and EP 305 216), *Rhizomucor miehei* lipase (See e.g., EP 238 023), *Candida lipase*, such as *C. antarctica* lipase (e.g., *C. antarctica* lipase A or B; See e.g., EP 214 761), a *Pseudomonas lipase* such as *P. alcaligenes* and *P. pseudoalcaligenes* lipase (See e.g., EP 218 272), *P. cepacia* lipase (See e.g., EP 331 376), *P. stutzeri* lipase (See e.g., GB 1,372,034), *P. fluorescens* lipase, *Bacillus* lipase (e.g., *B. subtilis* lipase [Dartois et al., Biochem. Biophys. Acta 1131:253-260 [1993]); *B. stearothermophilus* lipase [See e.g., JP 64/744992]; and *B. pumilus* lipase [See e.g., WO 91/16422]).

Furthermore, a number of cloned lipases find use in some embodiments of the present invention, including but not limited to *Penicillium camembertii* lipase (See, Yamaguchi et al., Gene 103:61-67 [1991]), *Geotricum candidum* lipase (See, Schimada et al., J. Biochem., 106:383-388 [1989]), and various *Rhizopus* lipases such as *R. delemar* lipase (See, Hass et al., Gene 109:117-113 [1991]), a *R. niveus* lipase (Kugimiya et al., Biosci. Biotech. Biochem. 56:716-719 [1992]) and *R. oryzae* lipase.

Other types of lipolytic enzymes such as cutinases also find use in some embodiments of the present invention, including but not limited to the cutinase derived from *Pseudomonas mendocina* (See, WO 88/09367), or cutinase derived from *Fusarium solani pisi* (See, WO 90/09446).

Additional suitable lipases include commercially available lipases such as M1 LIPASE™, LUMA FAST™, and LIPOMAX™ (Genencor); LIPOLASE® and LIPOLASE® ULTRA (Novozymes); and LIPASE P™ "Amano" (Amano Pharmaceutical Co. Ltd., Japan).

In some embodiments of the present invention, the cleaning compositions of the present invention further comprise lipases at a level from 0.00001% to 10% of additional lipase by weight of the composition and the balance of cleaning adjunct materials by weight of composition. In other aspects of the present invention, the cleaning compositions of the present invention also comprise, lipases at a level of 0.0001% to 10%, 0.001% to 5%, 0.001% to 2%, 0.005% to 0.5% lipase by weight of the composition.

Any amylase (alpha and/or beta) suitable for use in alkaline solutions also find use in some embodiments of the present invention. Suitable amylases include, but are not limited to those of bacterial or fungal origin. Chemically or genetically modified mutants are included in some embodiments. Amylases that find use in the present invention, include, but are not limited to α-amylases obtained from *B. licheniformis* (See e.g., GB 1,296,839). Commercially available amylases that find use in the present invention include, but are not limited to DURAMYL®, TERMAMYL®, FUNGAMYL®, BAN™, STAINZYME® and NATALASE® (Novozymes) and RAPIDASE® and MAXAMYL® P (Genencor International).

In some embodiments of the present invention, the cleaning compositions of the present invention further comprise amylases at a level from 0.00001% to 10% of additional amylase by weight of the composition and the balance of cleaning adjunct materials by weight of composition. In other aspects of the present invention, the cleaning compositions of the present invention also comprise, amylases at a level of 0.0001% to 10%, 0.001% to 5%, 0.001% to 2%, 0.005% to 0.5% amylase by weight of the composition.

Any cellulase suitable for use in alkaline solutions find use in embodiments of the present invention. Suitable cellulases include, but are not limited to those of bacterial or fungal origin. Chemically or genetically modified mutants are included in some embodiments. Suitable cellulases include, but are not limited to Humicola insolens cellulases (See e.g., U.S. Pat. No. 4,435,307). Especially suitable cellulases are the cellulases having color care benefits (See e.g., EP 0 495 257).

Commercially available cellulases that find use in the present include, but are not limited to CELLUZYME® (Novozymes), and KAC-500(B)™ (Kao Corporation). In some embodiments, cellulases are incorporated as portions or fragments of mature wild-type or variant cellulases, wherein a portion of the N-terminus is deleted (See e.g., U.S. Pat. No. 5,874,276).

In some embodiments, the cleaning compositions of the present invention can further comprise cellulases at a level from 0.00001% to 10% of additional cellulase by weight of the composition and the balance of cleaning adjunct materials by weight of composition. In other aspects of the present invention, the cleaning compositions of the present invention also comprise cellulases at a level of 0.0001% to 10%, 0.001% to 5%, 0.001% to 2%, 0.005% to 0.5% cellulase by weight of the composition.

Any mannanases suitable for use in detergent compositions and or alkaline solutions find use in the present invention. Suitable mannanases include, but are not limited to those of bacterial or fungal origin. Chemically or genetically modified mutants are included in some embodiments. Various mannanases are known which find use in the present invention (See e.g., U.S. Pat. Nos. 6,566,114, 6,602,842, and 6,440, 991, all of which are incorporated herein by reference).

In some embodiments, the cleaning compositions of the present invention can further comprise mannanases at a level from 0.00001% to 10% of additional mannanase by weight of the composition and the balance of cleaning adjunct materials by weight of composition. In other aspects of the present invention, the cleaning compositions of the present invention also comprise, mannanases at a level of 0.0001% to 10%, 0.001% to 5%, 0.001% to 2%, 0.005% to 0.5% mannanases by weight of the composition.

In some embodiments, peroxidases are used in combination with hydrogen peroxide or a source thereof (e.g., a percarbonate, perborate or persulfate). In alternative embodiments, oxidases are used in combination with oxygen. Both types of enzymes are used for "solution bleaching" (i.e., to prevent transfer of a textile dye from a dyed fabric to another fabric when the fabrics are washed together in a wash liquor), together with an enhancing agent (See e.g., WO 94/12621 and WO 95/01426). Suitable peroxidases/oxidases include, but are not limited to those of plant, bacterial or fungal origin. Chemically or genetically modified mutants are included in some embodiments.

In some embodiments, the cleaning compositions of the present invention can further comprise peroxidase and/or oxidase enzymes at a level from 0.00001% to 10% of additional peroxidase and/or oxidase by weight of the composition and the balance of cleaning adjunct materials by weight of composition. In other aspects of the present invention, the cleaning compositions of the present invention also comprise, peroxidase and/or oxidase enzymes at a level of 0.0001% to 10%, 0.001% to 5%, 0.001% to 2%, 0.005% to 0.5% peroxidase and/or oxidase enzymes by weight of the composition.

Mixtures of the above mentioned enzymes are encompassed herein, in particular a mixture of the 1AG3 enzyme, one or more additional proteases, at least one amylase, at least one lipase, at least one mannanase, and/or at least one cellulase. Indeed, it is contemplated that various mixtures of these enzymes will find use in the present invention.

It is contemplated that the varying levels of the protease and one or more additional enzymes may both independently range to 10%, the balance of the cleaning composition being cleaning adjunct materials. The specific selection of cleaning adjunct materials are readily made by considering the surface, item, or fabric to be cleaned, and the desired form of the composition for the cleaning conditions during use (e.g., through the wash detergent use).

Examples of suitable cleaning adjunct materials include, but are not limited to, surfactants, builders, bleaches, bleach activators, bleach catalysts, other enzymes, enzyme stabilizing systems, chelants, optical brighteners, soil release polymers, dye transfer agents, dispersants, suds suppressors, dyes, perfumes, colorants, filler salts, hydrotropes, photoactivators, fluorescers, fabric conditioners, hydrolyzable surfactants, preservatives, anti-oxidants, anti-shrinkage agents, germicides, fungicides, color speckles, silvercare, anti-tarnish and/or anti-corrosion agents, alkalinity sources, solubilizing agents, carriers, processing aids, pigments, and pH control agents (See e.g., in U.S. Pat. Nos. 6,610,642, 6,605,458, 5,705,464, 5,710,115, 5,698,504, 5,695,679, 5,686,014 and 5,646,101, all of which are incorporated herein by reference). Embodiments of specific cleaning composition materials are exemplified in detail below.

If the cleaning adjunct materials are not compatible with the proteases of the present invention in the cleaning compositions, then suitable methods of keeping the cleaning adjunct materials and the protease(s) separated (i.e., not in contact with each other) until combination of the two components is appropriate are used. Such separation methods include any suitable method known in the art (e.g., gelcaps, encapulation, tablets, physical separation, etc.).

In certain embodiments, an effective amount of one or more protease(s) provided herein are included in compositions useful for cleaning a variety of surfaces in need of proteinaceous stain removal. Such cleaning compositions include cleaning compositions for such applications as cleaning hard surfaces, fabrics, and dishes. Indeed, in some embodiments, the present invention provides fabric cleaning compositions, while in other embodiments, the present invention provides non-fabric cleaning compositions. Notably, the present invention also provides cleaning compositions suitable for personal care, including oral care (including dentrifices, toothpastes, mouthwashes, etc., as well as denture cleaning compositions), skin, and hair cleaning compositions. It is intended that the present invention encompass detergent compositions in any form (i.e., liquid, granular, bar, semi-solid, gels, emulsions, tablets, capsules, etc.).

By way of example, several cleaning compositions wherein the protease of the present invention find use are described in greater detail below. In embodiments in which the cleaning compositions of the present invention are formulated as compositions suitable for use in laundry machine washing method(s), the compositions of the present invention contain at least one surfactant and at least one builder compound, as well as one or more cleaning adjunct materials selected from organic polymeric compounds, bleaching agents, additional enzymes, suds suppressors, dispersants, lime-soap dispersants, soil suspension and anti-redeposition agents and corrosion inhibitors. In some embodiments, laundry compositions also contain softening agents (i.e., as additional cleaning adjunct materials).

The compositions of the present invention also find use detergent additive products in solid or liquid form. Such additive products are intended to supplement and/or boost the performance of conventional detergent compositions and can be added at any stage of the cleaning process.

In embodiments formulated as compositions for use in manual dishwashing methods, the compositions of the invention may contain at least one surfactant and at least one additional cleaning adjunct material selected from organic polymeric compounds, suds enhancing agents, group II metal ions, solvents, hydrotropes and additional enzymes.

In some embodiments, the density of the laundry detergent compositions herein ranges from 400 to 1200 g/liter, while in other embodiments, it ranges from 500 to 950 g/liter of composition measured at 20° C.

In some embodiments, various cleaning compositions such as those provided in U.S. Pat. No. 6,605,458 find use with the proteases of the present invention. Thus, in some embodiments, the compositions comprising at least one protease of the present invention is a compact granular fabric cleaning composition, while in other embodiments, the composition is a granular fabric cleaning composition useful in the laundering of colored fabrics, in further embodiments, the composition is a granular fabric cleaning composition which provides softening through the wash capacity, in additional embodiments, the composition is a heavy duty liquid fabric cleaning composition.

In some embodiments, the compositions comprising at least one protease of the present invention are fabric cleaning compositions such as those described in U.S. Pat. Nos. 6,610,642 and 6,376,450. In addition, the proteases of the present invention find use in granular laundry detergent compositions of particular utility under European or Japanese washing conditions (See e.g., U.S. Pat. No. 6,610,642).

In alternative embodiments, the present invention provides hard surface cleaning compositions comprising at least one protease provided herein. Thus, in some embodiments, the compositions comprising at least one protease of the present invention is a hard surface cleaning composition such as those described in U.S. Pat. Nos. 6,610,642, 6,376,450, and 6,376,450.

In yet further embodiments, the present invention provides dishwashing compositions comprising at least one protease provided herein. Thus, in some embodiments, the compositions comprising at least one protease of the present invention is a hard surface cleaning composition such as those in U.S. Pat. Nos. 6,610,642, and 6,376,450.

In still further embodiments, the present invention provides dishwashing compositions comprising at least one protease provided herein. Thus, in some embodiments, the compositions comprising at least one protease of the present invention comprise oral care compositions such as those in U.S. Pat. Nos. 6,376,450, and 6,376,450.

The formulations and descriptions of the compounds and cleaning adjunct materials contained in the aforementioned U.S. Pat. Nos. 6,376,450; 6,605,458; 6,605,458; and 6,610,642 are expressly incorporated by reference herein. Still further examples are set forth in the Examples below.

Still further, the present invention provides compositions and methods for the production of a food or animal feed, characterized in that protease according to the invention is mixed with food or animal feed. In some embodiments, the protease is added as a dry product before processing, while in other embodiments it is added as a liquid before or after processing. In some embodiments, in which a dry powder is used, the enzyme is diluted as a liquid onto a dry carrier such as milled grain. The proteases of the present invention find use as components of animal feeds and/or additives such as those described U.S. Pat. Nos. 5,612,055, 5,314,692. and 5,147,642, all of which are hereby incorporated by reference.

The enzyme feed additive according to the present invention is suitable for preparation in a number of methods. For example, in some embodiments, it is prepared simply by mixing different enzymes having the appropriate activities to produce an enzyme mix. In some embodiments, this enzyme mix is mixed directly with a feed, while in other embodiments, it is impregnated onto a cereal-based carrier material such as milled wheat, maize or soya flour. The present invention also encompasses these impregnated carriers, as they find use as enzyme feed additives.

In some alternative embodiments, a cereal-based carrier (e.g., milled wheat or maize) is impregnated either simultaneously or sequentially with enzymes having the appropriate activities. For example, in some embodiments, a milled wheat carrier is first sprayed with a xylanase, secondly with a protease, and optionally with a β-glucanase. The present invention also encompasses these impregnated carriers, as they find use as enzyme feed additives. In some embodiments, these impregnated carriers comprise at least one protease of the present invention.

In some embodiments, the feed additive of the present invention is directly mixed with the animal feed, while in alternative embodiments, it is mixed with one or more other feed additives such as a vitamin feed additive, a mineral feed additive, and/or an amino acid feed additive. The resulting feed additive including several different types of components is then mixed in an appropriate amount with the feed.

In some embodiments, the feed additive of the present invention, including cereal-based carriers is normally mixed in amounts of 0.01-50 g per kilogram of feed, e.g. 0.1-10 g/kilogram, or about 1 g/kilogram.

In alternative embodiments, the enzyme feed additive of the present invention involves construction of recombinant microorganisms that produces the desired enzyme(s) in the desired relative amounts. In some embodiments, this is accomplished by increasing the copy number of the gene encoding at least one protease of the present invention, and/or by using a suitably strong promoter operatively linked to the polynucleotide encoding the protease(s). In further embodiments, the recombinant microorganism strain has certain enzyme activities deleted (e.g., cellulases, endoglucanases, etc.), as desired.

In additional embodiments, the enzyme feed additives provided by the present invention also include other enzymes, including but not limited to at least one xylanase, α-amylase, glucoamylase, pectinase, mannanase, α-galactosidase, phytase, and/or lipase. In some embodiments, the enzymes having the desired activities are mixed with the xylanase and protease either before impregnating these on a cereal-based carrier or alternatively such enzymes are impregnated simultaneously or sequentially on such a cereal-based carrier. The carrier is then in turn mixed with a cereal-based feed to prepare the final feed. In alternative embodiments, the enzyme feed additive is formulated as a solution of the individual enzyme activities and then mixed with a feed material pre-formed as pellets or as a mash.

In still further embodiments, the enzyme feed additive is included in animals' diets by incorporating it into a second (i.e., different) feed or the animals' drinking water. Accordingly, it is not essential that the enzyme mix provided by the present invention be incorporated into the cereal-based feed itself, although such incorporation forms a particular embodiment of the present invention. The ratio of the units of xylanase activity per g of the feed additive to the units of protease activity per g of the feed additive may be 1:0.001-1,000, 1:0.01-100, or 1:0.1-10. As indicated above, the enzyme mix provided by the present invention may find use as a feed additive in the preparation of a cereal-based feed.

In some embodiments, the cereal-based feed comprises at least 25% by weight, or more at least 35% by weight, wheat or maize or a combination of both of these cereals. The feed further comprises a protease (i.e., at least one protease of the present invention) in such an amount that the feed includes a protease in such an amount that the feed includes 100-100,000 units of protease activity per kg.

Cereal-based feeds provided the present invention according to the present invention find use as feed for a variety of non-human animals, including poultry (e.g., turkeys, geese, ducks, chickens, etc.), livestock (e.g., pigs, sheep, cattle, goats, etc.), and companion animals (e.g., horses, dogs, cats, rabbits, mice, etc.). The feeds are particularly suitable for poultry and pigs, and in particular broiler chickens.

The present invention also provides compositions for the treatment of textiles that include at least one of the proteases of the present invention. In some embodiments, at least one protease of the present invention is a component of compositions suitable for the treatment of silk or wool (See e.g., U.S. RE Pat. No. 216,034, EP 134,267, U.S. Pat. No. 4,533,359, and EP 344,259).

In addition, the proteases of the present invention find use in a variety of applications where it is desirable to separate phosphorous from phytate. Accordingly, the present invention also provides methods producing wool or animal hair material with improved properties. In some embodiments, these methods comprise the steps of pretreating wool, wool fibres or animal hair material in a process selected from the group consisting of plasma treatment processes and the Delhey process; and subjecting the pretreated wool or animal hair material to a treatment with a proteolytic enzyme (e.g., at least one protease of the present invention) in an amount effective for improving the properties. In some embodiments, the proteolytic enzyme treatment occurs prior to the plasma treatment, while in other embodiments, it occurs after the plasma treatment. In some further embodiments, it is conducted as a separate step, while in other embodiments, it is conducted in combination with the scouring or the dyeing of the wool or animal hair material. In additional embodiments, at least one surfactant and/or at least one softener is present during the enzyme treatment step, while in other embodiments, the surfactant(s) and/or softener(s) are incorporated in a separate step wherein the wool or animal hair material is subjected to a softening treatment.

In some embodiments, the compositions of the present invention find us in methods for shrink-proofing wool fibers (See e.g., JP 4-327274). In some embodiments, the compositions are used in methods for shrink-proofing treatment of wool fibers by subjecting the fibers to a low-temperature plasma treatment, followed by treatment with a shrink-proofing resin such as a block-urethane resin, polyamide epochlorohydrin resin, glyoxalic resin, ethylene-urea resin or acrylate resin, and then treatment with a weight reducing proteolytic enzyme for obtaining a softening effect). In some embodiments, the plasma treatment step is a low-temperature treatment, e.g., a corona discharge treatment or a glow discharge treatment.

In some embodiments, the low-temperature plasma treatment is carried out by using a gas, e.g., a gas selected from the group consisting of air, oxygen, nitrogen, ammonia, helium, or argon. Conventionally, air is used but it may be advantageous to use any of the other indicated gasses.

The low-temperature plasma treatment may be carried out at a pressure between about 0.1 torr and 5 torr for from about 2 seconds to about 300 seconds, e.g., for about 5 seconds to about 100 seconds, or from about 5 seconds to about 30 seconds.

As indicated above, the present invention finds use in conjunction with methods such as the Delhey process (See e.g., DE-A-43 32 692). In this process, the wool is treated in an aqueous solution of hydrogen peroxide in the presence of soluble wolframate, optionally followed by treatment in a solution or dispersion of synthetic polymers, for improving the anti-felting properties of the wool. In this method, the wool is treated in an aqueous solution of hydrogen peroxide (0.1-35% (w/w), e.g., 2-10% (w/w)), in the presence of a 2-60% (w/w), e.g., 8-20% (w/w) of a catalyst (e.g., $Na_2WO_4$), and in the presence of a nonionic wetting agent. The treatment may be carried out at pH 8-11, and room temperature. The treatment time depends on the concentrations of hydrogen peroxide and catalyst, but may be 2 minutes or less. After the oxidative treatment, the wool is rinsed with water. For removal of residual hydrogen peroxide, and optionally for additional bleaching, the wool is further treated in acidic solutions of reducing agents (e.g., sulfites, phosphites etc.).

In some embodiments, the enzyme treatment step carried out for between about 1 minute and about 120 minutes. This step may be carried out at a temperature of between about 20° C. and about 60° C., e.g., between about 30° C. and about 50° C. Alternatively, the wool is soaked in or padded with an aqueous enzyme solution and then subjected to steaming at a conventional temperature and pressure, typically for about 30 seconds to about 3 minutes. In some embodiments, the proteolytic enzyme treatment is carried out in an acidic or neutral or alkaline medium which may include a buffer.

In alternative embodiments, the enzyme treatment step is conducted in the presence of one or more conventional anionic, non-ionic (e.g., Dobanol; Henkel AG) or cationic surfactants. An example of a useful nonionic surfactant is Dobanol (from Henkel AG). In further embodiments, the wool or animal hair material is subjected to an ultrasound treatment, either prior to or simultaneous with the treatment with a proteolytic enzyme. In some embodiments, the ultrasound treatment is carried out at a temperature of about 50° C. for about 5 minutes. In some embodiments, the amount of proteolytic enzyme used in the enzyme treatment step is between about 0.2 w/w % and about 10 w/w %, based on the weight of the wool or animal hair material. In some embodiments, in order to the number of treatment steps, the enzyme treatment is carried out during dyeing and/or scouring of the wool or animal hair material, simply by adding the protease to the dyeing, rinsing and/or scouring bath. In some embodiments, enzyme treatment is carried out after the plasma treatment but in other embodiments, the two treatment steps are carried out in the opposite order.

Softeners conventionally used on wool are usually cationic softeners, either organic cationic softeners or silicone based products, but anionic or non-inoc softeners are also useful. Examples of useful softeners include, but are not limited to polyethylene softeners and silicone softeners (i.e., dimethyl polysiloxanes (silicone oils)), H-polysiloxanes, silicone elastomers, aminofunctional dimethyl polysiloxanes, aminofunctional silicone elastomers, and epoxyfunctional dimethyl polysiloxanes, and organic cationic softeners (e.g. alkyl quarternary ammonium derivatives).

In additional embodiments, the present invention provides compositions for the treatment of an animal hide that includes at least one protease of the present invention. In some embodiments, the proteases of the present invention find use in compositions for treatment of animal hide, such as those described in WO 03/00865 (Insect Biotech Co., Taejeon-Si, Korea). In additional embodiments, the present invention provides methods for processing hides and/or skins into leather comprising enzymatic treatment of the hide or skin with the protease of the present invention (See e.g., WO 96/11285). In additional embodiments, the present invention provides compositions for the treatment of an animal skin or hide into leather that includes at least one protease of the present invention.

Hides and skins are usually received in the tanneries in the form of salted or dried raw hides or skins. The processing of hides or skins into leather comprises several different process steps including the steps of soaking, unhairing and bating. These steps constitute the wet processing and are performed in the beamhouse. Enzymatic treatment utilizing the proteases of the present invention are applicable at any time during the process involved in the processing of leather. However, proteases are usually employed during the wet processing (i.e., during soaking, unhairing and/or bating). Thus, in some embodiments, the enzymatic treatment with at least one of the proteases of the present invention occurs during the wet processing stage.

In some embodiments, the soaking processes of the present invention are performed under conventional soaking conditions (e.g., at a pH in the range pH 6.0-11). In some embodiments, the range is pH 7.0-10.0. In alternative embodiments, the temperature is in the range of 20-30° C., while in other embodiments it is in the range 24-28° C. In yet further embodiments, the reaction time is in the range 2-24 hours, e.g., in the range of 4-16 hours. In additional embodiments, tensides and/or preservatives are provided as desired.

The second phase of the bating step usually commences with the addition of the bate itself. In some embodiments, the enzymatic treatment takes place during bating. In some embodiments, the enzymatic treatment takes place during bating, after the deliming phase. In some embodiments, the bating process of the presents invention is performed using conventional conditions (e.g., at a pH in the range pH 6.0-9.0). In some embodiments, the pH range is 6.0 to 8.5. In further embodiments, the temperature is in the range of 20-30° C., while in other embodiments, the temperature is in the range of 25-28° C. In some embodiments, the reaction time is in the range of 20-90 minutes, while in other embodiments, it is in the range 40-80 minutes. Processes for the manufacture of leather are well known to those skilled in the art (See e.g., WO 94/069429 WO 90/1121189, U.S. Pat. No. 3,840,433, EP 505920, GB 2233665, and U.S. Pat. No. 3,986,926, all of which are herein incorporated by reference).

In further embodiments, the present invention provides bates comprising at least one protease of the present invention. A bate is an agent or an enzyme-containing preparation comprising the chemically active ingredients for use in beamhouse processes, in particular in the bating step of a process for the manufacture of leather. In some embodiments, the present invention provides bates comprising protease and suitable excipients. In some embodiments, agents including, but not limited to chemicals known and used in the art, e.g. diluents, emulgators, delimers and carriers. In some embodiments, the bate comprising at least one protease of the present invention is formulated as known in the art (See e.g., GB-A2250289, WO 96/11285, and EP 0784703).

In some embodiments, the bate of the present invention contains from 0.00005 to 0.01 g of active protease per g of bate, while in other embodiments, the bate contains from 0.0002 to 0.004 g of active protease per g of bate.

Thus, the proteases of the present invention find use in numerous applications and settings.

Experimental

The present invention is described in further detail in the following Examples which are not in any way intended to limit the scope of the invention as claimed. The attached Figures are meant to be considered as integral parts of the specification and description of the invention. All references cited are herein specifically incorporated by reference for all that is described therein. The following Examples are offered to illustrate, but not to limit the claimed invention In the experimental disclosure which follows, the following abbreviations apply: PI (proteinase inhibitor), ppm (parts per million); M (molar); mM (millimolar); μM (micromolar); nM (nanomolar); mol (moles); mmol (millimoles); μmol (micromoles); nmol (nanomoles); gm (grams); mg (milligrams); μg (micrograms); pg (picograms); L (liters); ml and mL (milliliters); μl and μL (microliters); cm (centimeters); mm (millimeters); μm (micrometers); nm (nanometers); U (units); V (volts); MW (molecular weight); sec (seconds); min(s) (minute/minutes); h(s) and hr(s) (hour/hours); ° C. (degrees Centigrade); QS (quantity sufficient); ND (not done); NA (not applicable); rpm (revolutions per minute); $H_2O$ (water); $dH_2O$ (deionized water); (HCl (hydrochloric acid); aa (amino acid); bp (base pair); kb (kilobase pair); kD (kilodaltons); cDNA (copy or complementary DNA); DNA (deoxyribonucleic acid); ssDNA (single stranded DNA); dsDNA (double stranded DNA); dNTP (deoxyribonucleotide triphosphate); RNA (ribonucleic acid); $MgCl_2$ (magnesium chloride); NaCl (sodium chloride); w/v (weight to volume); v/v (volume to volume); g (gravity); OD (optical density); Dulbecco's phosphate buffered solution (DPBS); SOC (2% Bacto-Tryptone, 0.5% Bacto Yeast Extract, 10 mM NaCl, 2.5 mM KCl); Terrific Broth (TB; 12 g/l Bacto Tryptone, 24 g/l glycerol, 2.31 g/l $KH_2PO_4$, and 12.54 g/l $K_2HPO_4$); $OD_{280}$ (optical density at 280 nm); $OD_{600}$ (optical density at 600 nm); $A_{405}$ (absorbance at 405 nm); Vmax (the maximum initial velocity of an enzyme catalyzed reaction); PAGE (polyacrylamide gel electrophoresis); PBS (phosphate buffered saline [150 mM NaCl, 10 mM sodium phosphate buffer, pH 7.2]); PBST (PBS+0.25% TWEEN® 20); PEG (polyethylene glycol); PCR (polymerase chain reaction); RT-PCR (reverse transcription PCR); SDS (sodium dodecyl sulfate); Tris (tris(hydroxymethyl)aminomethane); HEPES (N-[2-Hydroxyethyl]piperazine-N-[2-ethanesulfonic acid]); HBS (HEPES buffered saline); SDS (sodium dodecylsulfate); Tris-HCl (tris[Hydroxymethyl]aminomethane-hydrochloride); Tricine (N-[tris-(hydroxymethyl)-methyl]-glycine); CHES (2-(N-cyclo-hexylamino) ethane-sulfonic acid); TAPS (3-{[tris-(hydroxymethyl)-methyl]-amino}-propanesulfonic acid); CAPS (3-(cyclo-hexylamino)-propane-sulfonic acid; DMSO (dimethyl sulfoxide); DTT (1,4-dithio-DL-threitol); SA (sinapinic acid (s,5-dimethoxy-4-hydroxy cinnamic acid); TCA (trichloroacetic acid); Glut and GSH (reduced glutathione); GSSG (oxidized glutathione); TCEP (Tris[2-carboxyethyl]phosphine); Ci (Curies); mCi (milliCuries); μCi (microCuries); HPLC (high pressure liquid chromatography); RP-HPLC (reverse phase high pressure liquid chromatography); TLC (thin layer chromatography); MALDI-TOF (matrix-assisted laser desorption/ionization--time of flight); Ts (tosyl); Bn (benzyl); Ph (phenyl); Ms (mesyl); Et (ethyl), Me (methyl); Taq (Thermus aquaticus DNA polymerase); Klenow (DNA polymerase I large (Klenow) fragment); rpm (revolutions per minute); EGTA (ethylene glycol-bis(β-aminoethyl ether) N,N,N',N'-tetraacetic acid); EDTA (ethylenediaminetetracetic acid); bla (β-lactamase or ampicillin-resistance gene); HDL (high density liquid); MJ Research (MJ Research, Reno, Nev.); Infors (InforsAG, Bottmingen-Basel, Switzerland); Baseclear (Baseclear BV, Inc., Leiden, the Netherlands); PerSeptive (PerSeptive Biosystems, Framingham, Mass.); ThermoFinnigan (ThermoFinnigan, San Jose, Calif.); Argo (Argo BioAnalytica, Morris Plains, N.J.);Seitz EKS (SeitzSchenk Filtersystems GmbH, Bad Kreuznach, Germany); Pall (Pall Corp., East Hills, N.Y.); Spectrum (Spectrum Laboratories, Dominguez Rancho, Calif.); Molecular Structure (Molecular Structure Corp., Woodlands, Tex.); Accelrys (Accelrys, Inc., San Diego, Calif.); Chemical Computing (Chemical Computing Corp., Montreal, Canada); New Brunswick (New Brunswick Scientific, Co., Edison, N.J.); CFT (Center for Test Materials, Vlaardingeng, the Netherlands); Procter & Gamble (Procter & Gamble, Inc., Cincinnati, Ohio); GE Healthcare (GE Healthcare, Chalfont St. Giles, United Kingdom); DNA2.0 (DNA2.0, Menlo Park, Calif.); OXOID (Oxoid, Basingstoke, Hampshire, UK); Megazyme (Megazyme International Ireland Ltd., Bray Business Park, Bray, Co., Wicklow, Ireland); Finnzymes (Finnzymes Oy, Espoo, Finland); Kelco (CP Kelco, Wilmington, Del.); Corning (Corning Life Sciences, Corning, N.Y.); (NEN (NEN Life Science Products, Boston, Mass.); Pharma AS (Pharma AS, Oslo, Norway); Dynal (Dynal, Oslo, Norway); Bio-Synthesis (Bio-Synthesis, Lewisville, Tex.); ATCC (American Type Culture Collection, Rockville, Md.); Gibco/BRL (Gibco/BRL, Grand Island, N.Y.); Sigma (Sigma Chemical Co., St. Louis, Mo.); Pharmacia (Pharmacia Biotech, Piscataway, N.J.); NCBI (National Center for Biotechnology Information); Applied Biosystems (Applied Biosystems, Foster City, Calif.); BD Biosciences and/or Clontech (BD Biosciences CLONTECH Laboratories, Palo Alto, Calif.); Operon Technologies (Operon Technologies, Inc., Alameda, Calif.); MWG Biotech (MWG Biotech, High Point, N.C.); Oligos Etc (Oligos Etc. Inc, Wilsonville, Oreg.); Bachem (Bachem Bioscience, Inc., King of Prussia, Pa.); Difco (Difco Laboratories, Detroit, Mich.); Mediatech (Mediatech, Herndon, Va.; Santa Cruz (Santa Cruz Biotechnology, Inc., Santa Cruz, Calif.); Oxoid (Oxoid Inc., Ogdensburg, N.Y.); Worthington (Worthington Biochemical Corp., Freehold, N.J.); GIBCO BRL or Gibco BRL (Life Technologies, Inc., Gaithersburg, Md.); Millipore (Millipore, Billerica, Mass.); Bio-Rad (Bio-Rad, Hercules, Calif.); Invitrogen (Invitrogen Corp., San Diego, Calif.); NEB (New England Biolabs, Beverly, Mass.); Sigma (Sigma Chemical Co., St. Louis, Mo.); Pierce (Pierce Biotechnology, Rockford, Ill.); Takara (Takara Bio Inc. Otsu, Japan); Roche (Hoffmann-La Roche, Basel, Switzerland); EM Science (EM Science, Gibbstown, N.J.); Qiagen (Qiagen, Inc., Valencia, Calif.); Biodesign (Biodesign Intl., Saco, Me.); Aptagen (Aptagen, Inc., Herndon, Va.); Sorvall (Sorvall brand, from Kendro Laboratory Products, Asheville, N.C.); Molecular Devices (Molecular Devices, Corp., Sunnyvale, Calif.); R&D Systems (R&D Systems, Minneapolis, Minn.); Stratagene (Stratagene Cloning Systems, La Jolla, Calif.); Marsh (Marsh Biosciences, Rochester, N.Y.); Bio-Tek (Bio-Tek Instruments, Winooski, Vt.); (Biacore (Biacore, Inc., Piscataway, N.J.); PeproTech (PeproTech, Rocky Hill, N.J.); SynPep (SynPep, Dublin, Calif.); New Objective (New Objective brand; Scientific Instrument Services, Inc., Ringoes, N.J.); Waters (Waters, Inc., Milford, Mass.); Matrix Science (Matrix Science, Boston, Mass.); Dionex (Dionex, Corp., Sunnyvale, Calif.); Monsanto (Monsanto Co., St. Louis, Mo.); Wintershall (Wintershall AG, Kassel, Germany); BASF (BASF Co., Florham Park, N.J.); Huntsman (Huntsman Petrochemical Corp., Salt Lake City, Utah); Enichem (Enichem Iberica, Barcelona, Spain); Fluka Chemie AG (Fluka Chemie AG, Buchs, Switzerland); Gist-Brocades (Gist-Brocades, NV, Delft, the Netherlands); Dow Corning (Dow Corning Corp., Midland, Mich.); ServiceXS (Service XS, the Netherlands) and Microsoft (Microsoft, Inc., Redmond, Wash.). hexylamino)-propane-sulfonic In some Examples below various detergent formulations are provided. The following Table provides definitions for some of the components utilized in these detergents.

| Detergent Definitions | |
|---|---|
| LAS | Sodium linear $C_{11-13}$ alkyl benzene sulfonate. |
| TAS | Sodium tallow alkyl sulphate. |
| CxyAS | Sodium $C_{1x}$-$C_{1y}$ alkyl sulfate. |
| CxyEz | $C_{1x}$-$C_{1y}$ predominantly linear primary alcohol condensed with an average of z moles of ethylene oxide. |
| CxyAEzS | $C_{1x}$-$C_{1y}$ sodium alkyl sulfate condensed with an average of z moles of ethylene oxide. Added molecule name in the examples. |
| Nonionic | Mixed ethoxylated/propoxylated fatty alcohol e.g. Plurafac LF404 being an alcohol with an average degree of ethoxylation of 3.8 and an average degree of propoxylation of 4.5. |
| QAS | $R_2 \bullet N + (CH_3)_2(C_2H_4OH)$ with $R_2 = C_{12}$-$C_{14}$. |
| Silicate | Amorphous Sodium Silicate ($SiO_2$:$Na_2O$ ratio = 1.6-3.2:1). |
| Metasilicate | Sodium metasilicate ($SiO_2$:$Na_2O$ ratio = 1.0). |
| Zeolite A | Hydrated Aluminosilicate of formula $Na_{12}(AlO_2SiO_2)_{12} \bullet 27H_2O$ |
| SKS-6 | Crystalline layered silicate of formula $\delta$-$Na_2Si_2O_5$. |
| Sulfate | Anhydrous sodium sulphate. |
| STPP | Sodium Tripolyphosphate. |
| MA/AA | Random copolymer of 4:1 acrylate/maleate, average molecular weight about 70,000-80,000. |
| AA | Sodium polyacrylate polymer of average molecular weight 4,500. |
| Polycarboxylate | Copolymer comprising mixture of carboxylated monomers such as acrylate, maleate and methyacrylate with a MW ranging between 2,000-80,000 such as Sokolan commercially available from BASF, being a copolymer of acrylic acid, MW4,500. |
| BB1 | 3-(3,4-Dihydroisoquinolinium)propane sulfonate |
| BB2 | 1-(3,4-dihydroisoquinolinium)-decane-2-sulfate |
| PB1 | Sodium perborate monohydrate. |
| PB4 | Sodium perborate tetrahydrate of nominal formula $NaBO_3 \bullet 4H_2O$. |
| Percarbonate | Sodium percarbonate of nominal formula $2Na_2CO_3 \bullet 3H_2O_2$. |
| TAED | Tetraacetyl ethylene diamine. |
| NOBS | Nonanoyloxybenzene sulfonate in the form of the sodium salt. |
| DTPA | Diethylene triamine pentaacetic acid. |
| HEDP | 1,1-hydroxyethane diphosphonic acid. |
| DETPMP | Diethyltriamine penta (methylene) phosphonate, marketed by Monsanto under the Trade name Dequest 2060. |
| EDDS | Ethylenediamine-N,N'-disuccinic acid, (S,S) isomer in the form of its sodium salt |
| Diamine | Dimethyl aminopropyl amine; 1,6-hezane diamine; 1,3-propane diamine; 2-methyl-1,5-pentane diamine; 1,3-pentanediamine; 1-methyl-diaminopropane. |
| DETBCHD | 5,12-diethyl-1,5,8,12-tetraazabicyclo [6,6,2] hexadecane, dichloride, Mn(II) salt |
| PAAC | Pentaamine acetate cobalt(III) salt. |
| Paraffin | Paraffin oil sold under the tradename Winog 70 by Wintershall. |
| Paraffin Sulfonate | A Paraffin oil or wax in which some of the hydrogen atoms have been replaced by sulfonate groups. |
| Aldose oxidase | Oxidase enzyme sold under the tradename Aldose Oxidase by Novozymes A/S |
| Galactose oxidase | Galactose oxidase from Sigma |
| Protease | Proteolytic enzyme sold under the tradename Savinase, Alcalase, Everlase by Novo Nordisk A/S, and the following from Genencor International, Inc: "Protease A" described in US RE 34,606 in FIGS. 1A, 1B, and 7, and at column 11, lines 11-37; "Protease B" described in U.S. Pat. No. 5,955,340 and U.S. Pat. No. 5,700,676 in FIGS. 1A, 1B and 5, as well as Table 1; and "Protease C" described in U.S. Pat. No. 6,312,936 and U.S. Pat. No. 6,482,628 in FIGS. 1-3 [SEQ ID 3], and at column 25, line 12, "Protease D" being the variant 101G/103A/104I/159D/232V/236H/245R/248D/252K (BPN' numbering) described in WO 99/20723. |
| Amylase | Amylolytic enzyme sold under the tradename Purafect ® Ox Am described in WO 94/18314, WO96/05295 sold by Genencor; Natalase ®, Termamyl ®, Fungamyl ® and Duramyl ®, all available from Novozymes A/S. |
| Lipase | Lipolytic enzyme sold under the tradename Lipolase Lipolase Ultra by Novozymes A/S and Lipomax by Gist-Brocades. |
| Cellulase | Cellulytic enzyme sold under the tradename Carezyme, Celluzyme and/or Endolase by Novozymes A/S. |
| Pectin Lyase | Pectaway ® and Pectawash ® available from Novozymes A/S. |
| PVP | Polyvinylpyrrolidone with an average molecular weight of 60,000 |
| PVNO | Polyvinylpyridine-N-Oxide, with an average molecular weight of 50,000. |
| PVPVI | Copolymer of vinylimidazole and vinylpyrrolidone, with an average molecular weight of 20,000. |
| Brightener 1 | Disodium 4,4'-bis(2-sulphostyryl)biphenyl. |
| Silicone antifoam | Polydimethylsiloxane foam controller with siloxane-oxyalkylene copolymer as dispersing agent with a ratio of said foam controller to said dispersing agent of 10:1 to 100:1. |

-continued

| Detergent Definitions | |
|---|---|
| Suds Suppressor | 12% Silicone/silica, 18% stearyl alcohol, 70% starch in granular form. |
| SRP 1 | Anionically end capped poly esters. |
| PEG X | Polyethylene glycol, of a molecular weight of x. |
| PVP K60 ® | Vinylpyrrolidone homopolymer (average MW 160,000) |
| Jeffamine ® ED-2001 | Capped polyethylene glycol from Huntsman |
| Isachem ® AS | A branched alcohol alkyl sulphate from Enichem |
| MME PEG (2000) | Monomethyl ether polyethylene glycol (MW 2000) from Fluka Chemie AG. |
| DC3225C | Silicone suds suppresser, mixture of Silicone oil and Silica from Dow Corning. |
| TEPAE | Tetreaethylenepentaamine ethoxylate. |
| BTA | Benzotriazole. |
| Betaine | $(CH_3)_3N^+CH_2COO^-$ |
| Sugar | Industry grade D-glucose or food grade sugar |
| CFAA | $C_{12}$-$C_{14}$ alkyl N-methyl glucamide |
| TPKFA | $C_{12}$-$C_{14}$ topped whole cut fatty acids. |
| Clay | A hydrated aluminumu silicate in a general formula $Al_2O_3SiO_2 \cdot xH_2O$. Types: Kaolinite, montmorillonite, atapulgite, illite, bentonite, halloysite. |
| pH | Measured as a 1% solution in distilled water at 20° C. |

EXAMPLE 1

Isolation of Microbial Strains and Cultivation

In this Example, the isolation and cultivation of *Streptomyces* 1AG3 are described. Strain 1AG3. The isolation medium used as an alkaline soil extract agar with rifampicin selective pressure. The soil extract medium was prepared as described below:

Preparation of Soil Extract Medium

Solution A:

Suspend 1 kg of garden soil in 1 litre water and autoclave for 20 min. at 120° C. Cool to room temperature and pour the suspension over a glass fibre filter to obtain a clear filtrate. Wash the soil retentate twice with 200 ml and 100 ml demineralized water. Add enough water to make the volume 1 litre.

Solution B:

| NaCl | 80 g/L |
|---|---|
| $Na_2CO_3$ | 20 g/L |

Mix and sterilize at 120° C. for 20 min.

Rifampicin Stock Solution:

Rifampicin (Sigma R3501) 50 mg/ml dissolved in DMSO and sterilized by filtration through a 20 μm membrane.

First, 20 g agar were added to 500 ml of solution A and the solution was sterilized at 120° C. for 20 min. Then, 500 ml of solution A were mixed with 500 ml of solution B and cooled to 60° C. Rifampicin was then added to give a final concentration of 50 μg/ml. The agar mixture was then poured into Petri plates and stored at 4° C. in closed polythene bags until inoculated with organisms.

Lake sediment and water were mixed with solution B in a ratio 1:1 and shaken thoroughly. After sedimentation, serial dilutions of supernatant were plated out on soil extract agar, pH 10 containing rifampicin. The plates were incubated at 30° C. in a tightly closed plastic box lined with damp paper towels to maintain humidity and to prevent evaporation, for several weeks. The plates were examined periodically by stereomicroscopy. Filamentous colonies observed during these examinations were picked and inoculated onto fresh medium.

EXAMPLE 2

Characterization of Strain 1AG3 by 16S rRNA Sequencing

In this Example, experiments conducted to characterize *Streptomyces* strain 1AG3 by 16S rDNA sequencing are described. A chromosomal DNA fraction containing the first 500 base pairs of the 16S rRNA gene was obtained by PCR as described below. The nucleotide sequence of the fragment was determined. The same primers were used for synthesis and sequencing.

Primers

```
                                          (SEQ ID NO: 22)
3338    5' - G(A/T)A TTA CCG CGG C(G/T)G CTG - 3'

(SEQ ID NO: 19)
3572    5' - AGA GTT TGA TCC TGG CTC AG - 3'
```

PCR Protocol

The reaction mixture contained 10 μL Pwo buffer (Boehringer Mannheim), 80.5 μL deionised water, 2 μL dNTP's (10 mM each), 1 μL of each primer (10 μg/L), 0.5 μL Pwo polymerase (5 U/μL) (Boehringer Mannheim) in a 500 μl Eppendorf tube.

The conditions for the PCR were: 25 cycles of 95° C. for 45 sec., followed by 55° C. for 45 sec., and then 72° C. for 2 min. The PCR fragments were purified by agarose gel electrophoresis followed by excision and isolation from the gel using the QIAquick® Gel Extraction Kit (Qiagen), using the manufacturer's reagents and instructions. The partial 16S rRNA gene of *Streptomyces* strain 1AG3 identified herein has the following sequence:

```
  1 GATCCTGGCT CAGGACGAAC GCTGGCGGCG TGCTTAACAC ATGCAAGTCG  (SEQ ID NO: 12)

51 AACGATGAAG CCGCTTCGGT GGTGGATTAG TGGCGAACGG GTGAGTAACA

101 CGTGGGCAAT CTGCCCTGCA CTCTGGGACA AGCCCGGGAA ACTGGGTCTA

151 ATACCGGATA TGACTGCTTC GGGCATCCGA GGTGGTGGAA AGCTCCGGCG

201 GTGCAGGATG GGCCCGCGGC CTATCAGCTT GTTGGTGGGG TGATGGCCTA

251 CCAAGGCGAC GACGGGTAGC CGGCCTGAGA GGGCGACCGG CCACACTGGG

301 ACTGAGACAC GGCCCAGACT CCTACGGGAG GCAGCAGTGG GGAATATTGC

351 ACAATGGGCG CAAGCCTGAT GCAGCGACGC CGCGTGAGGG ATGACGGCCT

401 TCGGGTTGTA AACCTCTTTC AGCAGGGAAG AAGC
```

A Blastn search in GenBank revealed that the closest neighbor of strain 1AG3 is *Streptomyces somaliensis* at 97% identity on a 434 bp overlap, indicating that strain 1AG3 is most likely a species of *Streptomyces*.

EXAMPLE 3

Identification of a Partial Gene Sequence of a Novel Protease Present in Alkaliphilic *Streptomyces* Strain 1AG3

In this Example, methods and compositions used to identify a partial sequence of the *Streptomyces* 1AG3 protease gene sequences are described. A PCR with degenerate primers StreptomycProt_FW and StreptomycProt_RV was performed on chromosomal DNA of natural isolate *Streptomyces* 1AG3. PCR resulted in a DNA fragment encoding a novel protease similar to proteins known as "Streptogrisins."

The PCR methods were used with the following degenerate primer set:

```
StreptomycProt_FW
5'-CGCTGYTCVVTSGGCTTC-3'       (SEQ ID NO: 13)

StreptomycProt_RV
5'-GCAGTYGCCNNNGCCGCCGGASGT-3' (SEQ ID NO: 14)
```

PCR was performed on a thermocycler with High Fidelity Platinum Taq polymerase (Invitrogen) according to the instructions of the manufacturer (annealing temperature of 50[deg.] C.). Genomic DNA of *Streptomyces* strain 1AG3 was isolated as described in Kieser et al. (Kieser et al., *Practical Streptomyces Genetics*, The John Innes Foundation, Norwich, United Kingdom [2000]) and used as template DNA in the PCR. The PCR resulted in a PCR fragment of approximately 400 bp and DNA Sequencing (ServiceXS,) revealed that the DNA sequence of this PCR fragment encodes a protein that is similar to other serine proteases. The partial nucleotide sequence of this 1AG3 protease is shown below. In this sequence, the sequence of the degenerate FW primer is underlined. The RV primer was not found, due to the poor sequence information quality at the end of the run (as indicated by the number of N's).

```
  1 CGCTGTTCGC TGGGCTTCCC CGTTCGCCGC GGAACTCAGG CGGGCTTCGC GACCGCGGGT  (SEQ ID NO: 15)

61 CACTGCGGCC GGGTCGGCAC CACCACACGG GGCTTCAACC AGGTGGCGCA GGGCACCTTC

121 CAGGGCTCCA TCTTCCCCGG CGCGGACATG GGCTGGGTCG CGGTCAACTC CAACTGGAAC

181 ACCACCCCCT TCGTCCGCGG CCAGGGGGGC GCGAACGTGA CGGTGGCGGG TTCGCAGCAG

241 GCTCCGGTCG GCTCCTCGGT GTGCCGTTCC GGCTCCACCA CCGGCTGGCA CTGCGGCACC

301 ATCCAGCAGC ACAACACCTC GGTGCGCTAT CCGGAGGGCC ACCATCAGCG GAGTGACCAC

361 GACCTCGGTG TGCGCCGAAC CNTAGTGACT CCGGCGGCGC CTACATCTTT GGGAACCACN

421 GCCCAGGGGC GTNTANGTCC CNTCCACCNA AGGCCANNTG CCA
```

The following sequence is a partial (translated) amino acid sequence of 1AG3 protease

```
                                                      (SEQ ID NO: 16)
RCSLGFPVRR GTQAGFATAG HCGRVGTTTR GFNQVAQGTF

QGSIFPGRDM GWVAVNSNWN TTPFVRGQGG ANVTVAGSQQ

APVGSSVCRS GSTTGWHCGT IQQHNTSVRY PEG
```

A Blast search revealed a similarity with the protein Streptogrisin C from *Streptomyces coelicolor* and other streptogrisins or serine proteases from various *Streptomyces* species and other microorganisms.

EXAMPLE 4

Elucidation of the Complete Gene and Protein Sequence of 1AG3 Protease

In this Example, experiments conducted to elucidate the entire 1AG3 protease gene and protein sequences are described. In these experiments, inverse PCR experiments were performed on chromosomal DNA of novel *Streptomyces* strain 1AG3 to isolate and clone the full-length 1AG3 protease gene from alkaliphilic *Streptomyces* Strain 1AG3. Based on the DNA sequence of approximantly 400 bp fragment of the *Streptomyces* Strain 1AG3_protease gene described in Example 3, novel DNA primers were designed:

```
                                        (SEQ ID NO: 18)
1AG3prot_RV   5'-GCGAAGCCCGCCTGAGTTCCGCGGCGAACG-3'

(SEQ ID NO: 17)
1AG3prot_FW   5'-GTGCCGTTCCGCCTCCACCACCGGCTGGCAC-3'
```

Chromosomal DNA of alkaliphilic *Streptomyces* Strain 1AG3 was digested with the restriction enzymes ApaI, BamHI, BssHII, KpnI, NarI, NcoI, NheI, PvuI, SalI or SstII, purified using the Qiagen PCR purification kit (Qiagen, Catalogue #28106) and self-ligated with T4 DNA ligase (Invitrogen) according to the manufacturers' instructions. accompanying each. Ligation mixtures were purified using the Qiagen PCR purification kit, (Qiagen) and a PCR was performed with primers 1AG3prot_RV and 1AG3prot_FW. PCR on DNA fragments that were digested with NcoI, NarI, BssHII, or SalI and thenr self-ligated, resulting in PCR products between approximately 0.6 and 2.5 kb. PCR was performed on a thermocycler with High Fidelity Platinum Taq polymerase (Invitrogen) according to the manufacturer's instructions (annealing temperature of 55° C., 35 cycles). DNA sequencing analysis (BaseClear, The Netherlands) revealed that the DNA fragment covers the main part of a streptogrisin-like protease gene from *Streptomyces griseus*.

The entire sequence of the 1AG3 protease gene was derived through additional sequence analysis reactions (BaseClear) on the same PCR products with primer 1AG3-up1 (5'-GTGGTGGCCACGACCAGCTCGGCGGTCTC-3'; SEQ ID NO:27) and 1AG3-up2 (5'-TGGTCCAGGAACCGGCGAAGGTGTC; SEQ ID NO:28). Sequence analysis with these primers resulted in the identification of the entire sequence of the 1AG3 protease gene of 1362 bp. The sequence is provided below.

```
  1 GACAGC GAGGAG ACCCCT C ATGCA CCGCAG ACGCGG AGCGCT ATTCGC CGGCGC CGTGGC   (SEQ ID NO: 1)
    CTGTCG CTCCTC TGGGGA GTACGT GGCGTC TGCGCC TCGCGA TAAGCG GCCGCG GCACCG

61 GATAGC CGCCCT GACGAT CGCCGC CGCGCC GGCCAC CGCCGG ACCGGC CCTCGC CCCGCC
    CTATCG GCGGGA CTGCTA GCGGCG GCGCGG CCGGTG GCGGCC TGGCCGGGAGCG GGGCGG

121 ACCGGC CCAGGA GACGGC GGCCCA GGAGAT CCCTGC CGGCAT GCTGCA GGCCAT GCAGCG
    TGGCCG GGTCCT CTGCCG CCGGGT CCTCTA GGGACG GCCGTA CGACGT CCGGTA CGTCGC

181 TGATCT CGGCCT CACCGA GCAGCA GGCCGA GGAGCG CGTGGC CAACGA GTACCA AGCGGG
    ACTAGA GCCGGA GTGGCT CGTCGT CCGGCT CCTCGC GCACCG GTTGCT CATGGT TCGCCC

241 CCAGCT GGAGCC ACGGCT GCGGGC GCAATT GGCGGA CACCTT CGCCGG TTCCTG GACCAG
    GGTCGA CCTCGG TGCCGA CGCCCG CGTTAA CCGCCT GTGGAA GCGGCC AAGGAC CTGGTC

301 GGGCGA GACCGC CGAGCT GGTCGT GGCCAC CACCGA CCGCGA GCAGCT ACCGGC GCTGAC
    CCCGCT CTGGCG GCTCGA CCAGCA CCGGTG GTGGCT GGCGCT CGTCGA TGGCCG CGACTG

361 GGCGGC GGGCGT GCGGGC CACCGT GGCCGA GCACAG CCTGTC CGAGCT CGAGGC CGTGAA
    CCGCCG CCCGCA CGCCCG GTGGCA CCGGCT CGTGTC GGACAG GCTCGA GCTCCG GCACTT

421 GGAGAC ACTGGA CGAGGC CGCCGA GGAGCA CGCCAC GACCGA GGCGCC CGTGTG GTACGT
    CCTCTG TGACCT GCTCCG GCGGCT CCTCGT GCGGTG CTGGCT CCGCGG GCACAC CATGCA

481 GGATGT CACGAG CAACAC GGTCAT CGTGCA CGCCCA GGACGT GACGGC CGGGCG CGACTT
    CCTACA GTGCTC GTTGTG CCAGTA GCACGT GCGGGT CCTGCA CTGCCG GCCCGC GCTGAA

541 CGTCTC GGCCGC GGGCGT GGACCC CGCCGC GGTCCA CGTGCT GCGCTC GGACGA GCAGCC
    GCAGAG CCGGCG CCCGCA CCTGGG GCGGCG CCAGGT GCACGA CGCGAG CCTGCT CGTCGG

601 GCGGCC TTACCA CGACCT GCGGGG TGGGGA GGCGTA CTACAT GGGCAG CGGAGG GCGCTG
    CGCCGG AATGGT GCTGGA CGCCCC ACCCCT CCGCAT GATGTA CCCGTC GCCTCC GCGCAC

661 CTCGGT CGGCTT CTCCGT TCGCCG CGGAAC TCAGGC GGGCTT CGCGAC CGCGGG TCACTG
    GAGCCA GCCGAA GAGGCA AGCGGC GCCTTG AGTCCG CCCGAA GCGCTG GCGCCC AGTGAC

721 CGGCCG GGTCGG CACCAC CACACG GGGCTT CAACCA GGTGGC GCAGGG CACCTT CCAGGG
    GCCGGC CCAGCC GTGGTG GTGTGC CCCGAA GTTGGT CCACCG CGTCCC GTGGAA GGTCCC

781 CTCCAT CTTCCC CGGGCG CGACAT GGGCTG GGTCGC GGTCAA CTCCAA CTGGAA CACCAC
    GAGGTA GAAGGG GCCCGC GCTGTA CCCGAC CCAGCG CCAGTT GAGGTT GACCTT GTGGTG

841 CCCCTT CGTCCG CGGCCA GGGGGG CGCGAA CGTGAC GGTGGC GGGTTC GCAGCA GGCTCC
    GGGGAA GCAGGC GCCGGT CCCCCC GCGCTT GCACTG CCACCG CCCAAG CGTCGT CCGAGG
```

```
-continued
 901 GGTCGG CTCCTC GGTGTG CCGTTC CGGCTC CACCAC CGGCTG GCACTG CGGCAC CATCCA
     CCAGCC GAGGAG CCACAC GGCAAG GCCGAG GTGGTG GCCGAC CGTGAC GCCGTG GTAGGT 961 GCAGCA CAACAC CTCGGT GCGCTA TCCGGA GGGCAC CATCAG CGGAGT GACCAG GACCTC
     CGTCGT GTTGTG GAGCCA CGCGAT AGGCCT CCCGTG GTAGTC GCCTCA CTGGTC CTGGAG 1021 GGTGTG CGCCGA ACCCGG TGACTC CGGCGG CGCCTA CATCTC CGGGAA CCAGGC CCAGGG
     CCACAC GCGGCT TGGGCC ACTGAG GCCGCC GCGGAT GTAGAG GCCCTT GGTCCG GGTCCC 1081 CGTGAC CTCCGG CGGCTC GGGCAA CTGCCG CACCGG TGGCAC CACCTA CCACCA GCCGAT
     GCACTG GAGGCC GCCGAG CCCGTT GACGGC GTGGCC ACCGTG GTGGAT GGTGGT CGGCTA 1141 CAACCC GCTGCT GGCACA GTGGAA CCTGAC CCTCGT GACCAC GGGCAA CGGCGG CGACCC
     GTTGGG CGACGA CCGTGT CACCTT GGACTG GGAGCA CTGGTG CCCGTT GCCGCC GCTGGG 1201 GGGCGA CCCCGG TGACCC GGGCGA CCCGGG TGAGCC CGGCGG CAGCTG GTCCGC CGGGAC
     CCCGCT GGGGCC ACTGGG CCCGCT GGGCCC ACTCGG GCCGCC GTCGAC CAGGCG GCCCTG 1261 CAGTTA CGCGGT CGGCGA CCGGGT GACCTA CGGCGG CGCGGA GTACCG CTGCCT GCAGGC
     GTCAAT GCGCCA GCCGCT GGCCCA CTGGAT GCCGCC GCGCCT CATGGC GACGGA CGTCCG 1321 CCACGT CGCCCA GTCCGG CTGGAC GCCCCC GAACAC GCCCGC CCTCTG GCAGCC CGTGTG
     GGTGCA GCGGGT CAGGCC GACCTG CGGGGG CTTGTG CGGGCG GGAGAC CGTCGC GCACAC

1381 ACACGA CCA
     TGTGCT GGT
```

In the above sequence, the ribosomal binding site is underlined, the start and stop codons are printed in bold, the (predicted) signal sequence is in italics, the (predicted) N-terminal pro-sequence is double underlined, and the mature protease chain sequence is underlined with a wavy line.

ing polynucleotides encoding a polypeptide having proteolytic activity and used such vectors to transform a *Streptomyces lividans* host cell. The transformation methods used herein are known in the art (See e.g., U.S. Pat. No. 6,287,839; and WO 02/50245, herein incorporated by reference).

```
  1 MHRRRGALFA GAVAIAALTI AAAPATAGPA LAPPPAQETA AQEIPAGMLQ   (SEQ ID NO: 3)

51 AMQRDLGLTE QQAEERVANE YQAGQLEPRL RAQLADTFAG SWTRGETAEL

101 VVATTDREQL PALTAAGVRA TVAEHSLSEL EAVKETLDEA AEEHATTEAP

151 VWYVDVTSNT VIVHAQDVTA GRDFVSAAGV DPAAVHVLRS DEQPRPYHDL

201 RGGEAYYMGS GGRCSVGFSV RRGTQAGFAT AGHCGRVGTT TRGFNQVAQG

251 TFQGSIFPGR DMGWVAVNSN WNTTPFVRGQ GGANVTVAGS QQAPVGSSVC

301 RSGSTTGWHC GTTQQHNTSV RYPEGTISGV TRTSVCAEPG DSGGAYISGN

351 QAQGVTSGGS GNCRTGGTTY HQPINPLLAQ WNLTLVTTGN GGDPGDPGDP

401 GDPGEPGGSW SAGTSYAVGD RVTYGGAEYR CLQAHVAQSG WTPPNTPALW

451 QRV
```

In the above sequence, the signal peptide (predicted) is indicated by double underlining, while the pro-sequence (predicted) is indicated by underlining, and the mature chain is shown in bold.

The molecular weight (MW) of 1AG43 protease was determined using LC-MS methods as known in the art. The measured MW (by LC-MS, see chromatograms and spectra below) of the ASP homologue 1AG3 was 21261 Da. This MW fits the 1AG3 sequence [49-256] (calculated MW 21250 Da,).

EXAMPLE 5

Cloning and Expression of 1AG3 Protease Gene in *Streptomyces lividans*

In this Example, cloning and expression of 1AG3 protease is described. Thus, this Example describes plasmids compris- The vector (i.e., plasmid) used in these experiments comprised a polynucleotide encoding a protease of the present invention obtained from alkaliphilic *Streptomyces* Strain 1AG3. This plasmid was used to transform *Streptomyces lividans*. The final plasmid vector is referred to herein as "pSEA4CT-1AG3." As with previous vectors, the construction of pSEA4CT-1AG3 made use of the pSEA4CT plasmid vector (See, above). An *Aspergillus niger* ("A4") regulatory sequence linked to the structural gene encoding the *Streptomyces* 1AG3 protease (1AG3) was used to drive the expression of the protease. A DNA fragment comprising the *Streptomyces* CelA signal-sequence, 1AG3 prosequence and 1AG3 mature protease sequence was constructed by PCR techniques known in the art, as an NheI-BamHI fragment. The polynucleotide primers for the cloning of *Streptomyces* 1AG3 protease (1AG3) in pSEA4CT are based on SEQ ID NO:1. The forward primer and reverse primer are shown below:

pSEA4C-1AG3-Fw:
(SEQ ID NO: 29)
5'-GACTGCGCTAGCCGGCCCCCCGGCACAGGCCACCGCCGGACCGGCCC
TCGCCCCGCCACCG-3' pSEA4C-1AG3-Rv:
(SEQ ID NO: 30)
5'-GCTCGCGGATCCCCATTGTCACACGCGCTGCCAGAGGGCGGGCGTGT
TC-3'

PCR was performed on a thermocycler with High Fidelity Platinum Taq polymerase (Invitrogen) according to the instructions of the manufacturer (annealing temperature of 55° C., 28 cycles). The resulting PCR fragment was digested with the restriction enzymes BamHI and NheI, and the pSEA4CT plasmid was digested with the restriction enzymes BamHI and XbaI. Both the digested 1AG3 PCR and plasmid DNA fragments were purified using the Qiagen PCR purification kit (Qiagen, Catalogue #28106). The 1AG3 protease fragment was cloned in the pSEA4CT plasmid by using the T4 DNA ligase kit (Invitrogen) using the manufacturer's instructions, resulting in the production of plasmid pSEA4CT-1AG3.

The host *Streptomyces lividans* TK23 was transformed with plasmid vector pSEA4CT-1AG3 using the protoplast method described in the previous Example (i.e., using the method of Hopwood et al., supra).

The transformed culture was expanded to provide three fermentation cultures in TS* medium. The composition of TS* medium was (g/L) tryptone (Difco) 16, soytone (Difco) 4, casein hydrolysate (Merck) 20, $K_2HPO_4$ 10, glucose 15, Basildon antifoam 0.6, pH 7.0. Incubation conditions: 30° C. 250 rpm (Infors HT). At various time points, samples of the fermentation broths were removed for analysis. For the purposes of this experiment, a skim milk procedure was used to confirm successful cloning. In this test, 30 µL of the shake flask supernatant were pipetted in punched out holes in skim milk agar plates and incubated at 37° C.

The incubated plates were visually reviewed after overnight incubation for the presence of clearing zones (halos) indicating the expression of proteolytic enzyme. For purposes of this experiment, the samples were also assayed for protease activity and for molecular weight (SDS-PAGE). At the end of the fermentation, full length protease was observed by SDS-PAGE. A sample of the fermentation broth was assayed as follows: 10 µL of the diluted supernatant was collected and added to 190 µL AAPF substrate solution (conc. 1 mg/ml, in 0.1 M Tris/0.005% TWEEN®-80, pH 8.6).

The rate of increase in absorbance at 410 nm due to release of p-nitroaniline was monitored (25° C.). The assay results for 3 clones are shown in Table (5.1), below.

TABLE 5.1

Assay Results

| CLONE | Ppm |
|---|---|
| 1-11 | 130 |
| 2-2 | 170 |
| 2-6 | 110 |

These results clearly show that the polynucleotide from *Streptomyces* sp 1AG3 encodes a polypeptide having proteolytic activity was expressed in *Streptomyces lividans*.

EXAMPLE 6

Relationship of 1AG3 Protease to Other Proteases

In this Example, methods used to determine the relationship between 1AG3 protease and other proteases are described. A BLASTP search of the 1AG3 polypeptide (SEQ ID NO:3) sequence in Swissprot revealed that streptogrisin C (SGPC) (SEQ ID NO:23) from *Streptomyces griseus* is the closest known homologue with 59.7% identity and 68.0% similarity, as indicated in the alignment provided in FIG. 2. When only the mature (i.e., catalytic domain) protease sequences are compared, the identity of 1AG3 protease (SEQ ID NO:9) and SGPC (SEQ ID NO:24) rises to 74.2%, and 80.1% similarity as indicated in FIG. 3. In this Figure, the active site amino acids his-asp-ser are printed in bold and the characteristic 3 disulfide bridges indicated by connecting lines.

1AG3 protease and *Cellulomonas* 69B4 (ASP) protease are orthologues. However, a sequence alignment of the 1AG3 protease (SEQ ID NO:3) and ASP protease (SEQ ID NO:25) reveals that their identity is low at 39.6%, with a similarity of 49.6%, as indicated in FIG. 4. When only the mature (catalytic) portion of the proteases are compared then the identity of 1AG3 (SEQ ID NO:9) to ASP (SEQ ID NO:26) increases to 44.1% and 53.1% similarity, as indicated in FIG. 5. Thus, the results indicate that 1AG3 has more than 50% homology to ASP. In addition, it was noted that 1AG3 has a larger molecular weight (approx. 21 kD) than ASP. Furthermore, it was determined that 1AG3 has a lower pI than ASP.

EXAMPLE 7

Liquid Fabric Cleaning Compositions

This Example provides liquid fabric cleaning compositions that find use in conjunction with the present invention. These compositions are contemplated to find particular utility under Japanese machine wash conditions, as well as for applications involving cleaning of fine and/or delicate fabrics. Table 7-1 provides a suitable composition. However, it is not intended that the present invention be limited to this specific formulation, as many other formulations find use with the present invention.

TABLE 7-1

Liquid Fabric Cleaning Composition

| Component | Amount (%) |
|---|---|
| AE2.5S | 2.16 |
| AS | 3.30 |
| N-Cocoyl N-methyl glucamine | 1.10 |
| Nonionic surfactant | 10.00 |
| Citric acid | 0.40 |
| Fatty acid | 0.70 |
| Base | 0.85 |
| Monoethanolamine | 1.01 |
| 1,2-Propanediol | 1.92 |
| EtOH | 0.24 |
| HXS | 2.09 |
| Protease.sup.1 | 0.01 |
| Amylase | 0.06 |
| Minors/inerts to 100% | |

EXAMPLE 8

Liquid Dishwashing Compositions

This Example provides liquid dishwashing compositions that find use in conjunction with the present invention. These compositions are contemplated to find particular utility under Japanese dish washing conditions. Table 8-1 provides suitable compositions. However, it is not intended that the present invention be limited to this specific formulation, as many other formulations find use with the present invention.

TABLE 8-1

Liquid Dishwashing Compositions

| Component | A | B |
|---|---|---|
| AE1.4S | 24.69 | 24.69 |
| N-cocoyl N-methyl glucamine | 3.09 | 3.09 |
| Amine oxide | 2.06 | 2.06 |
| Betaine | 2.06 | 2.06 |
| Nonionic surfactant | 4.11 | 4.11 |
| Hydrotrope | 4.47 | 4.47 |
| Magnesium | 0.49 | 0.49 |
| Ethanol | 7.2 | 7.2 |
| LemonEase | 0.45 | 0.45 |
| Geraniol/BHT | — | 0.60/0.02 |
| Amylase | 0.03 | 0.005 |
| Protease | 0.01 | 0.43 |
| Balance to 100% | | |

EXAMPLE 9

Liquid Fabric Cleaning Compositions

The proteases of the present invention find particular use in cleaning compositions. For example, it is contemplated that liquid fabric cleaning composition of particular utility under Japanese machine wash conditions be prepared in accordance with the invention. In some embodiments, these compositions comprise the following components shown in Table 9-1. Unless otherwise indicated, the "protease" in this and the Tables in the following Examples is the 1AG3 protease provided herein.

TABLE 9-1

Liquid Fabric Cleaning Composition

| Component | Amount (%) |
|---|---|
| AE2.5S | 15.00 |
| AS | 5.50 |
| N-Cocoyl N-methyl glucamine | 5.50 |
| Nonionic surfactant | 4.50 |
| Citric acid | 3.00 |
| Fatty acid | 5.00 |
| Base | 0.97 |
| Monoethanolamine | 5.10 |
| 1,2-Propanediol | 7.44 |
| EtOH | 5.50 |
| HXS | 1.90 |
| Boric Acid | 3.50 |
| Ethoxylated tetraethylenepentaimine | 3.00 |
| SRP | 0.30 |
| Protease | 0.069 |
| Amylase | 0.06 |
| Cellulase | 0.08 |
| Lipase | 0.18 |
| Brightener | 0.10 |
| Minors/inerts to 100% | |

EXAMPLE 10

Granular Fabric Cleaning Compositions

In this Example, various granular fabric cleaning compositions that find use with the present invention are provided. The following Tables provide suitable compositions. However, it is not intended that the present invention be limited to these specific formulations, as many other formulations find use with the present invention.

TABLE 10-1

Granular Fabric Cleaning Compositions

| | Formulations | | | |
|---|---|---|---|---|
| Component | A | B | C | D |
| Protease1 | 0.10 | 0.20 | 0.03 | 0.05 |
| Protease2 | | | 0.2 | 0.15 |
| C13 linear alkyl benzene sulfonate | 22.00 | 22.00 | 22.00 | 22.00 |
| Phosphate (as sodium tripolyphosphate) | 23.00 | 23.00 | 23.00 | 23.00 |
| Sodium carbonate | 23.00 | 23.00 | 23.00 | 23.00 |
| Sodium silicate | 14.00 | 14.00 | 14.00 | 14.00 |
| Zeolite | 8.20 | 8.20 | 8.20 | 8.20 |
| Chelant (diethylaenetriamine-petaacetic acid) | 0.40 | 0.40 | 0.40 | 0.40 |
| Sodium sulfate | 5.50 | 5.50 | 5.50 | 5.50 |
| Water | Balance to 100% | | | |

TABLE 10-2

Granular Fabric Cleaning Compositions

| | Formulations | | | |
|---|---|---|---|---|
| Component | A | B | C | D |
| Protease1 | 0.10 | 0.20 | 0.30 | 0.05 |
| Protease2 | | | 0.2 | 0.1 |
| C12 alkyl benzene sulfonate | 12.00 | 12.00 | 12.00 | 12.00 |
| Zeolite A (1-10 micrometer) | 26.00 | 26.00 | 26.00 | 26.00 |
| C12-C14 secondary (2,3) alkyl sulfate, Na salt | 5.00 | 5.00 | 5.00 | 5.00 |
| Sodium citrate | 5.00 | 5.00 | 5.00 | 5.00 |
| Optical brightenere | 0.10 | 0.10 | 0.10 | 0.10 |
| Sodium sulfate | 17.00 | 17.00 | 17.00 | 17.00 |
| Fillers, water, minors | Balance to 100% | | | |

The following laundry detergent compositions are contemplated to provide particular utility under European machine wash conditions.

TABLE 10-3

Granular Fabric Cleaning Compositions

| | Formulations | | |
|---|---|---|---|
| Component | A | B | C |
| LAS | 7.0 | 5.61 | 4.76 |
| TAS | | | 1.57 |
| C45AS | 6.0 | 2.24 | 3.89 |
| C25E25 | 1.0 | 0.76 | 1.18 |
| C45E7 | | | 2.0 |
| C25E3 | 4.0 | 5.5 | |
| QAS | 0.8 | 2.0 | 2.0 |
| STPP | | | |
| Zeolite | 25.0 | 19.5 | 19.5 |
| Citric acid | 2.0 | 2.0 | 2.0 |
| NaSKS-6 | 8.0 | 10.6 | 10.6 |
| Carbonate I | 8.0 | 10.0 | 8.6 |
| MA/AA | 1.0 | 2.6 | 1.6 |

TABLE 10-3-continued

Granular Fabric Cleaning Compositions

| Component | Formulations | | |
|---|---|---|---|
| | A | B | C |
| CMC | 0.5 | 0.4 | 0.4 |
| PB4 | | 12.7 | |
| Percarbonate | | | 19.7 |
| TAED | | 3.1 | 5.0 |
| Citrate | 7.0 | | |
| DTPMP | 0.25 | 0.2 | 0.3 |
| HEDP | 0.3 | 0.3 | 0.3 |
| QEA 1 | 0.9 | 1.2 | 1.0 |
| Protease1 | 0.02 | 0.05 | 0.035 |
| Lipase | 0.15 | 0.25 | 0.15 |
| Cellulase | 0.28 | 0.28 | 0.28 |
| Amylase | 0.4 | 0.7 | 0.3 |
| PVPI/PVNO | 0.4 | | 0.1 |
| Photoactivated bleach (ppm) | 15 ppm | 27 ppm | 27 ppm |
| Brightener 1 | 0.08 | 0.19 | 0.19 |
| Brightener 2 | | 0.04 | 0.04 |
| Perfume | 0.3 | 0.3 | 0.3 |
| Effervescent granules (malic acid 40%, sodium bicarbonate 40%, sodium carbonate 20%) | 15 | 15 | 5 |
| Silicon antifoam | 0.5 | 2.4 | 2.4 |
| Minors/inerts to 100% | | Balance to 100% | |

EXAMPLE 11

Detergent Formulations

In this Example, various detergent formulations which find use with 1AG3 and/or 1AG3 variants are provided. It is understood that the test methods provided in this section must be used to determine the respective values of the parameters of the present invention.

In the exemplified detergent compositions, the enzymes levels are expressed by pure enzyme by weight of the total composition and unless otherwise specified, the detergent ingredients are expressed by weight of the total compositions.

The following Table (Table 11-1) provides liquid laundry detergent compositions that are prepared.

TABLE 11-1

Liquid Laundry Detergent Compositions

| Component | I | II | III | IV | V |
|---|---|---|---|---|---|
| LAS | 24.0 | 32.0 | 6.0 | 8.0 | 6.0 |
| $C_{12}$-$C_{15}AE_{1.8}S$ | — | — | 8.0 | 11.0 | 5.0 |
| $C_8$-$C_{10}$ amido propyl dimethyl amine | 2.0 | 2.0 | 2.0 | 2.0 | 1.0 |
| $C_{12}$-$C_{14}$ alkyl dimethyl amine oxide | — | — | — | — | 2.0 |
| $C_{12}$-$C_{15}$ AS | — | — | 17.0 | 7.0 | 8.0 |
| CFAA | — | 5.0 | 4.0 | 4.0 | 3.0 |
| $C_{12}$-$C_{14}$ Fatty alcohol ethoxylate | 12.0 | 6.0 | 1.0 | 1.0 | 1.0 |
| $C_{12}$-$C_{18}$ Fatty acid | 3.0 | — | 4.0 | 4.0 | 3.0 |
| Citric acid (anhydrous) | 6.0 | 5.0 | 3.0 | 3.0 | 2.0 |
| DETPMP | — | — | 1.0 | 1.0 | 0.5 |
| Monoethanolamine | # | # | 5.0 | 5.0 | 2.0 |
| Sodium hydroxide | — | — | 2.5 | 1.0 | 1.5 |
| Propanediol | 12.7 | 14.5 | 13.1 | 10. | 8.0 |

TABLE 11-1-continued

Liquid Laundry Detergent Compositions

| Component | I | II | III | IV | V |
|---|---|---|---|---|---|
| Ethanol | 1.8 | 2.4 | 4.7 | 5.4 | 1.0 |
| DTPA | 0.5 | 0.4 | 0.3 | 0.4 | 0.5 |
| Pectin Lyase | — | — | — | 0.005 | — |
| Amylase | 0.001 | 0.002 | — | — | — |
| Cellulase | — | — | 0.0002 | — | 0.0001 |
| Lipase | 0.1 | — | 0.1 | — | 0.1 |
| ASP | 0.05 | 0.3 | 0.08 | 0.5 | 0.2 |
| Protease A | — | — | — | — | 0.1 |
| Aldose Oxidase | — | — | 0.3 | — | 0.003 |
| DETBCHD | — | — | 0.02 | 0.01 | — |
| SRP1 | 0.5 | 0.5 | — | 0.3 | 0.3 |
| Boric acid | 2.4 | 2.4 | 2.8 | 2.8 | 2.4 |
| Sodium xylene sulfonate | — | — | 3.0 | — | — |
| DC 3225C | 1.0 | 1.0 | 1.0 | 1.0 | 1.0 |
| 2-butyl-octanol | 0.03 | 0.04 | 0.04 | 0.03 | 0.03 |
| Brightener 1 | 0.12 | 0.10 | 0.18 | 0.08 | 0.10 |

Balance to 100% perfume/dye and/or water
added to product to adjust the neat pH of the product to about 4.2 for (I) and about 3.8 for (II).

The following Table (11-2) provides hand dish liquid detergent compositions that are prepared.

TABLE 11-2

Hand Dish Liquid Detergent Compositions

| Component | I | II | III | IV | V | VI |
|---|---|---|---|---|---|---|
| $C_{12}$-$C_{15}AE_{1.8}S$ | 30.0 | 28.0 | 25.0 | — | 15.0 | 10.0 |
| LAS | — | — | — | 5.0 | 15.0 | 12.0 |
| Paraffin Sulfonate | — | — | — | 20.0 | — | — |
| $C_{10}$-$C_{18}$ Alkyl Dimethyl Amine Oxide | 5.0 | 3.0 | 7.0 | — | — | — |
| Betaine | 3.0 | — | 1.0 | 3.0 | 1.0 | — |
| $C_{12}$ poly-OH fatty acid amide | — | — | — | 3.0 | — | 1.0 |
| $C_{14}$ poly-OH fatty acid amide | — | 1.5 | — | — | — | — |
| $C_{11}E_9$ | 2.0 | — | 4.0 | — | — | 20.0 |
| DTPA | — | — | — | — | 0.2 | — |
| Tri-sodium Citrate dihydrate | 0.25 | — | — | 0.7 | — | — |
| Diamine | 1.0 | 5.0 | 7.0 | 1.0 | 5.0 | 7.0 |
| $MgCl_2$ | 0.25 | — | — | 1.0 | — | — |
| ASP | 0.02 | 0.01 | 0.03 | 0.01 | 0.02 | 0.05 |
| Protease A | — | 0.01 | — | — | — | — |
| Amylase | 0.001 | — | — | 0.002 | — | 0.001 |
| Aldose Oxidase | 0.03 | — | 0.02 | — | 0.05 | — |
| Sodium Cumene Sulphonate | — | — | — | 2.0 | 1.5 | 3.0 |
| PAAC | 0.01 | 0.01 | 0.02 | — | — | — |
| DETBCHD | — | — | — | 0.01 | 0.02 | 0.01 |

Balance to 100% perfume/dye and/or water
The pH of these compositions is about 8 to about 11

Table 11-3 provides liquid automatic dishwashing detergent compositions that are prepared.

TABLE 11-3

Liquid Automatic Dishwashing Detergent Compositions

| Component | I | II | III | IV | V |
|---|---|---|---|---|---|
| STPP | 16 | 16 | 18 | 16 | 16 |
| Potassium Sulfate | — | 10 | 8 | — | 10 |
| 1,2 propanediol | 6.0 | 0.5 | 2.0 | 6.0 | 0.5 |
| Boric Acid | 4.0 | 3.0 | 3.0 | 4.0 | 3.0 |
| $CaCl_2$ dihydrate | 0.04 | 0.04 | 0.04 | 0.04 | 0.04 |

TABLE 11-3-continued

Liquid Automatic Dishwashing Detergent Compositions

| Component | I | II | III | IV | V |
|---|---|---|---|---|---|
| Nonionic | 0.5 | 0.5 | 0.5 | 0.5 | 0.5 |
| ASP | 0.1 | 0.03 | 0.05 | 0.03 | 0.06 |
| Protease B | — | — | — | 0.01 | — |
| Amylase | 0.02 | — | 0.02 | 0.02 | — |
| Aldose Oxidase | — | 0.15 | 0.02 | — | 0.01 |
| Galactose Oxidase | — | — | 0.01 | — | 0.01 |
| PAAC | 0.01 | — | — | 0.01 | — |
| DETBCHD | — | 0.01 | — | — | 0.01 |

Balance to 100% perfume/dye and/or water

Table 11-4 provides laundry compositions which may be prepared in the form of granules or tablets that are prepared.

TABLE 11-4

Laundry Compositions

| Base Product | I | II | III | IV | V |
|---|---|---|---|---|---|
| $C_{14}$-$C_{15}$AS or TAS | 8.0 | 5.0 | 3.0 | 3.0 | 3.0 |
| LAS | 8.0 | — | 8.0 | — | 7.0 |
| $C_{12}$-$C_{15}$AE$_3$S | 0.5 | 2.0 | 1.0 | — | — |
| $C_{12}$-$C_{15}$E$_5$ or E$_3$ | 2.0 | — | 5.0 | 2.0 | 2.0 |
| QAS | — | — | — | 1.0 | 1.0 |
| Zeolite A | 20.0 | 18.0 | 11.0 | — | 10.0 |
| SKS-6 (dry add) | — | — | 9.0 | — | — |
| MA/AA | 2.0 | 2.0 | 2.0 | — | — |
| AA | — | — | — | — | 4.0 |
| 3Na Citrate 2H$_2$O | — | 2.0 | — | — | — |
| Citric Acid (Anhydrous) | 2.0 | — | 1.5 | 2.0 | — |
| DTPA | 0.2 | 0.2 | — | — | — |
| EDDS | — | — | 0.5 | 0.1 | — |
| HEDP | — | — | 0.2 | 0.1 | — |
| PB1 | 3.0 | 4.8 | — | — | 4.0 |
| Percarbonate | — | — | 3.8 | 5.2 | — |
| NOBS | 1.9 | — | — | — | — |
| NACA OBS | — | — | 2.0 | — | — |
| TAED | 0.5 | 2.0 | 2.0 | 5.0 | 1.00 |
| BB1 | 0.06 | — | 0.34 | — | 0.14 |
| BB2 | — | 0.14 | — | 0.20 | — |
| Anhydrous Na Carbonate | 15.0 | 18.0 | 8.0 | 15.0 | 15.0 |
| Sulfate | 5.0 | 12.0 | 2.0 | 17.0 | 3.0 |
| Silicate | — | 1.0 | — | — | 8.0 |
| ASP | 0.03 | 0.05 | 1.0 | 0.06 | 0.1 |
| Protease B | — | 0.01 | — | — | — |
| Protease C | — | — | — | 0.01 | — |
| Lipase | — | 0.008 | — | — | — |
| Amylase | 0.001 | — | — | — | 0.001 |
| Cellulase | — | 0.0014 | — | — | — |
| Pectin Lyase | 0.001 | 0.001 | 0.001 | 0.001 | 0.001 |
| Aldose Oxidase | 0.03 | — | 0.05 | — | — |
| PAAC | — | 0.01 | — | — | 0.05 |

Balance to 100% Moisture and/or Minors*
*Perfume, Dye, Brightener/SRP1/Na Carboxymethylcellulose/Photobleach/MgSO$_4$/PVPVI/Suds suppressor/High Molecular PEG/Clay.

Table 11-5 provides liquid laundry detergent formulations which are prepared.

TABLE 11-5

Liquid Laundry Detergent Formulations

| Component | I | I | II | III | IV | V |
|---|---|---|---|---|---|---|
| LAS | 11.5 | 11.5 | 9.0 | — | 4.0 | — |
| $C_{12}$-$C_{15}$AE$_{2.85}$S | — | — | 3.0 | 18.0 | — | 16.0 |
| $C_{14}$-$C_{15}$E$_{2.5}$S | 11.5 | 11.5 | 3.0 | — | 16.0 | — |
| $C_{12}$-$C_{13}$E$_9$ | — | — | 3.0 | 2.0 | 2.0 | 1.0 |
| $C_{12}$-$C_{13}$E$_7$ | 3.2 | 3.2 | — | — | — | — |
| CFAA | — | — | — | 5.0 | — | 3.0 |

TABLE 11-5-continued

Liquid Laundry Detergent Formulations

| Component | I | I | II | III | IV | V |
|---|---|---|---|---|---|---|
| TPKFA | 2.0 | 2.0 | — | 2.0 | 0.5 | 2.0 |
| Citric Acid (Anhydrous) | 3.2 | 3.2 | 0.5 | 1.2 | 2.0 | 1.2 |
| Ca formate | 0.1 | 0.1 | 0.06 | 0.1 | — | — |
| Na formate | 0.5 | 0.5 | 0.06 | 0.1 | 0.05 | 0.05 |
| Na Culmene Sulfonate | 4.0 | 4.0 | 1.0 | 3.0 | 1.2 | — |
| Borate | 0.6 | 0.6 | — | 3.0 | 2.0 | 3.0 |
| Na Hydroxide | 6.0 | 6.0 | 2.0 | 3.5 | 4.0 | 3.0 |
| Ethanol | 2.0 | 2.0 | 1.0 | 4.0 | 4.0 | 3.0 |
| 1,2 Propanediol | 3.0 | 3.0 | 2.0 | 8.0 | 8.0 | 5.0 |
| Mono-ethanolamine | 3.0 | 3.0 | 1.5 | 1.0 | 2.5 | 1.0 |
| TEPAE | 2.0 | 2.0 | — | 1.0 | 1.0 | 1.0 |
| ASP | 0.03 | 0.05 | 0.01 | 0.03 | 0.08 | 0.02 |
| Protease A | — | — | 0.01 | — | — | — |
| Lipase | — | — | — | 0.002 | — | — |
| Amylase | — | — | — | — | 0.002 | — |
| Cellulase | — | — | — | — | — | 0.0001 |
| Pectin Lyase | 0.005 | 0.005 | — | — | — | — |
| Aldose Oxidase | 0.05 | — | — | 0.05 | — | 0.02 |
| Galactose oxidase | — | 0.04 | — | — | — | — |
| PAAC | 0.03 | 0.03 | 0.02 | — | — | — |
| DETBCHD | — | — | — | 0.02 | 0.01 | — |
| SRP 1 | 0.2 | 0.2 | — | 0.1 | — | — |
| DTPA | — | — | — | 0.3 | — | — |
| PVNO | — | — | — | 0.3 | — | 0.2 |
| Brightener 1 | 0.2 | 0.2 | 0.07 | 0.1 | — | — |
| Silicone antifoam | 0.04 | 0.04 | 0.02 | 0.1 | 0.1 | 0.1 |

Balance to 100% perfume/dye and/or water

Table 11-6 provides compact high density dishwashing detergents that are prepared.

TABLE 11-6

Compact High Density Dishwashing Detergents

| Component | I | II | III | IV | V | VI |
|---|---|---|---|---|---|---|
| STPP | — | 45.0 | 45.0 | — | — | 40.0 |
| 3Na Citrate 2H$_2$O | 17.0 | — | — | 50.0 | 40.2 | — |
| Na Carbonate | 17.5 | 14.0 | 20.0 | — | 8.0 | 33.6 |
| Bicarbonate | — | — | — | 26.0 | — | — |
| Silicate | 15.0 | 15.0 | 8.0 | — | 25.0 | 3.6 |
| Metasilicate | 2.5 | 4.5 | 4.5 | — | — | — |
| PB1 | — | — | 4.5 | — | — | — |
| PB4 | — | — | — | 5.0 | — | — |
| Percarbonate | — | — | — | — | — | 4.8 |
| BB1 | — | 0.1 | 0.1 | — | 0.5 | — |
| BB2 | 0.2 | 0.05 | — | 0.1 | — | 0.6 |
| Nonionic | 2.0 | 1.5 | 1.5 | 3.0 | 1.9 | 5.9 |
| HEDP | 1.0 | — | — | — | — | — |
| DETPMP | 0.6 | — | — | — | — | — |
| PAAC | 0.03 | 0.05 | 0.02 | — | — | — |
| Paraffin | 0.5 | 0.4 | 0.4 | 0.6 | — | — |
| ASP | 0.072 | 0.053 | 0.053 | 0.026 | 0.059 | 0.01 |
| Protease B | — | — | — | — | — | 0.01 |
| Amylase | 0.012 | — | 0.012 | — | 0.021 | 0.006 |
| Lipase | — | 0.001 | — | 0.005 | — | — |
| Pectin Lyase | 0.001 | 0.001 | 0.001 | — | — | — |
| Aldose Oxidase | 0.05 | 0.05 | 0.03 | 0.01 | 0.02 | 0.01 |
| BTA | 0.3 | 0.2 | 0.2 | 0.3 | 0.3 | 0.3 |
| Polycarboxylate | 6.0 | — | — | — | 4.0 | 0.9 |
| Perfume | 0.2 | 0.1 | 0.1 | 0.2 | 0.2 | 0.2 |

Balance to 100% Moisture and/or Minors*
*Brightener/Dye/SRP1/Na Carboxymethylcellulose/Photobleach/MgSO$_4$/PVPVI/Suds suppressor/High Molecular PEG/Clay.
The pH of the above compositions is from about 9.6 to about 11.3.

Table 11-7 provides tablet detergent compositions of the present invention that are prepared by compression of a granular dishwashing detergent composition at a pressure of 13KN/cm² using a standard 12 head rotary press:

TABLE 11-7

Tablet Detergent Compositions

| Component | I | II | III | IV | V | VI | VII | VIII |
|---|---|---|---|---|---|---|---|---|
| STPP | — | 48.8 | 44.7 | 38.2 | — | 42.4 | 46.1 | 36.0 |
| 3Na Citrate 2H$_2$O | 20.0 | — | — | — | 35.9 | — | — | — |
| Na Carbonate | 20.0 | 5.0 | 14.0 | 15.4 | 8.0 | 23.0 | 20.0 | 28.0 |
| Silicate | 15.0 | 14.8 | 15.0 | 12.6 | 23.4 | 2.9 | 4.3 | 4.2 |
| Lipase | 0.001 | — | 0.01 | — | 0.02 | — | — | — |
| Protease B | 0.01 | — | — | — | — | — | — | — |
| Protease C | — | — | — | — | — | 0.01 | — | — |
| ASP | 0.01 | 0.08 | 0.05 | 0.04 | 0.052 | 0.023 | 0.023 | 0.029 |
| Amylase | 0.012 | 0.012 | 0.012 | — | 0.015 | — | 0.017 | 0.002 |
| Pectin Lyase | 0.005 | — | — | 0.002 | — | — | — | — |
| Aldose Oxidase | — | 0.03 | — | 0.02 | 0.02 | — | 0.03 | — |
| PB1 | — | — | 3.8 | — | 7.8 | — | — | 8.5 |
| Percarbonate | 6.0 | — | — | 6.0 | — | 5.0 | — | — |
| BB1 | 0.2 | — | 0.5 | — | 0.3 | 0.2 | — | — |
| BB2 | — | 0.2 | — | 0.5 | — | — | 0.1 | 0.2 |
| Nonionic | 1.5 | 2.0 | 2.0 | 2.2 | 1.0 | 4.2 | 4.0 | 6.5 |
| PAAC | 0.01 | 0.01 | 0.02 | — | — | — | — | — |
| DETBCHD | — | — | — | 0.02 | 0.02 | — | — | — |
| TAED | — | — | — | — | — | 2.1 | — | 1.6 |
| HEDP | 1.0 | — | — | 0.9 | — | 0.4 | 0.2 | — |
| DETPMP | 0.7 | — | — | — | — | — | — | — |
| Paraffin | 0.4 | 0.5 | 0.5 | 0.5 | — | — | 0.5 | — |
| BTA | 0.2 | 0.3 | 0.3 | 0.3 | 0.3 | 0.3 | 0.3 | — |
| Polycarboxylate | 4.0 | — | — | — | 4.9 | 0.6 | 0.8 | — |
| PEG 400-30,000 | — | — | — | — | — | 2.0 | — | 2.0 |
| Glycerol | — | — | — | — | — | 0.4 | — | 0.5 |
| Perfume | — | — | — | 0.05 | 0.2 | 0.2 | 0.2 | 0.2 |

Balance to 100% Moisture and/or Minors*
*Brightener/SRP1/Na Carboxymethylcellulose/Photobleach/MgSO$_4$/PVPVI/Suds suppressor/High Molecular PEG/Clay.
The pH of these compositions is from about 10 to about 11.5.
The tablet weight of these compositions is from about 20 grams to about 30 grams.

Table 11-8 provides liquid hard surface cleaning detergent compositions of the present invention that are prepared.

TABLE 11-8

Liquid Hard Surface Cleaning Detergent Compositions

| Component | I | II | III | IV | V | VI | VII |
|---|---|---|---|---|---|---|---|
| C$_9$-C$_{11}$E$_5$ | 2.4 | 1.9 | 2.5 | 2.5 | 2.5 | 2.4 | 2.5 |
| C$_{12}$-C$_{14}$E$_5$ | 3.6 | 2.9 | 2.5 | 2.5 | 2.5 | 3.6 | 2.5 |
| C$_7$-C$_9$E$_6$ | — | — | — | — | 8.0 | — | — |
| C$_{12}$-C$_{14}$E$_{21}$ | 1.0 | 0.8 | 4.0 | 2.0 | 2.0 | 1.0 | 2.0 |
| LAS | — | — | — | 0.8 | 0.8 | — | 0.8 |
| Sodium culmene sulfonate | 1.5 | 2.6 | — | 1.5 | 1.5 | 1.5 | 1.5 |
| Isachem ® AS | 0.6 | 0.6 | — | — | — | 0.6 | — |
| Na$_2$CO$_3$ | 0.6 | 0.13 | 0.6 | 0.1 | 0.2 | 0.6 | 0.2 |
| 3Na Citrate 2H$_2$O | 0.5 | 0.56 | 0.5 | 0.6 | 0.75 | 0.5 | 0.75 |
| NaOH | 0.3 | 0.33 | 0.3 | 0.3 | 0.5 | 0.3 | 0.5 |
| Fatty Acid | 0.6 | 0.13 | 0.6 | 0.1 | 0.4 | 0.6 | 0.4 |
| 2-butyl octanol | 0.3 | 0.3 | — | 0.3 | 0.3 | 0.3 | 0.3 |
| PEG DME-2000 ® | 0.4 | — | 0.3 | 0.35 | 0.5 | — | — |
| PVP | 0.3 | 0.4 | 0.6 | 0.3 | 0.5 | — | — |
| MME PEG (2000) ® | — | — | — | — | — | 0.5 | 0.5 |
| Jeffamine ® ED-2001 | — | 0.4 | — | — | 0.5 | — | — |
| PAAC | — | — | — | 0.03 | 0.03 | 0.03 | — |
| DETBCHD | 0.03 | 0.05 | 0.05 | — | — | — | — |
| ASP | 0.07 | 0.05 | 0.08 | 0.03 | 0.06 | 0.01 | 0.04 |
| Protease B | — | — | — | — | — | 0.01 | — |
| Amylase | 0.12 | 0.01 | 0.01 | — | 0.02 | — | 0.01 |
| Lipase | — | 0.001 | — | 0.005 | — | 0.005 | — |
| Pectin Lyase | 0.001 | — | 0.001 | — | — | — | 0.002 |
| PB1 | — | 4.6 | — | 3.8 | — | — | — |
| Aldose Oxidase | 0.05 | — | 0.03 | — | 0.02 | 0.02 | 0.05 |

Balance to 100% perfume/dye and/or water
The pH of these compositions is from about 7.4 to about 9.5.

Of course, it is to be understood that a wide range of changes and modifications can be made to the embodiment described above. It is therefore intended that the foregoing detailed description be understood in the context of the following claims, including all equivalents, which are intended to define the scope of this invention.

EXAMPLE 12

Animal Feed Comprising 1AG3

The present invention also provides animal feed compositions comprising aAG3 and/or 1AG3 variants. In this Example, one such feed, suitable for poultry is provided. However, it is not intended that the present invention be limited to this specific formulation, as the proteases of the present invention find use with numerous other feed formulations. It is further intended that the feeds of the present invention be suitable for administration to any animal, including but not limited to livestock (e.g., cattle, pigs, sheep, etc.), as well as companion animals (e.g., dogs, cats, horses, rodents, etc.). The following Table provides a formulation for a mash, namely a maize-based starter feed suitable for administration to turkey poults up to 3 weeks of age.

TABLE 12-1

Animal Feed Composition

| Ingredient Amount | (wt. %) |
|---|---|
| Maize | 36.65 |
| Soybean meal (45.6% CP) | 55.4 |
| Animal-vegetable fat | 3.2 |
| Dicalcium phosphate | 2.3 |
| Limestone | 1.5 |
| Mineral premix | 0.3 |
| Vitamin premix | 0.3 |
| Sodium chloride | 0.15 |
| DL methionine | 0.2 |

In some embodiments, this feed formulation is supplemented with various concentrations of the protease(s) of the present invention (e.g., 2,000 units/kg, 4,000 units/kg and 6,000 units/kg).

All patents and publications mentioned in the specification are indicative of the levels of those skilled in the art to which the invention pertains. All patents and publications are herein incorporated by reference to the same extent as if each individual publication was specifically and individually indicated to be incorporated by reference. However, the citation of any publication is not to be construed as an admission that it is prior art with respect to the present invention.

Having described exemplary embodiments of the present invention, it will appear to those ordinarily skilled in the art that various modifications may be made to the disclosed embodiments, and that such modifications are intended to be within the scope of the present invention.

Those of skill in the art readily appreciate that the present invention is well adapted to carry out the objects and obtain the ends and advantages mentioned, as well as those inherent therein. The compositions and methods described herein are representative and are not intended as limitations on the scope of the invention. It is readily apparent to one skilled in the art that varying substitutions and modifications may be made to the invention disclosed herein without departing from the scope and spirit of the invention.

The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

We claim:

1. An isolated protein comprising a serine protease consisting of an amino acid sequence that is at least 95% identical to the *Streptomyces* 1AG3 protease of SEQ ID NO:9.

2. The isolated protein of claim 1, wherein said serine protease consists of the amino acid sequence of said *Streptomyces* 1AG3 protease.

3. The isolated protein of claim 1, wherein said serine protease comprises at least one amino acid substitution relative to said *Streptomyces* 1AG3 protease.

4. A cleaning composition comprising the isolated protein of claim 1.

5. The cleaning composition of claim 4, wherein said cleaning composition further comprises a surfactant.

6. The cleaning composition of claim 5, wherein said surfactant is a sodium alkyl sulfate surfactant that comprises an ethylene oxide moiety.

7. The cleaning composition of claim 4, said composition comprising from about 0.001% to about 0.5% by weight of said isolated protein.

8. The cleaning composition of claim 4, wherein said cleaning composition is formulated as a laundry detergent 9. The cleaning composition of claim 4, wherein said cleaning composition is formulated as a dishwashing detergent 10. The cleaning composition of claim 4, further comprising an additional enzyme selected from a protease, amylase, lipase, mannanase, pectinase, cutinase, oxidoreductase, hemicellulase, and cellulase.

11. The cleaning composition of claim 4, further comprising a stabilizing agent.

12. The cleaning composition of claim 4, wherein said cleaning composition is a solid composition.

13. The cleaning composition of claim 7, wherein said cleaning composition is a liquid composition.

* * * * *

UNITED STATES PATENT AND TRADEMARK OFFICE
CERTIFICATE OF CORRECTION

PATENT NO. : 7,618,801 B2
APPLICATION NO. : 11/929817
DATED : November 17, 2009
INVENTOR(S) : Brian E. Jones, Marc Kolkman and Chris Leeflang Page 1 of 1

It is certified that error appears in the above-identified patent and that said Letters Patent is hereby corrected as shown below:

On the Title page, Item No. 73, delete "Danison US Inc." and insert -- Danisco US Inc. --.

Signed and Sealed this
Twenty-fourth Day of April, 2012

David J. Kappos
*Director of the United States Patent and Trademark Office*

SEQUENCE LISTING

```
<160> NUMBER OF SEQ ID NOS: 30

<210> SEQ ID NO 1
<211> LENGTH: 1389
<212> TYPE: DNA
<213> ORGANISM: Streptomyces sp.

<400> SEQUENCE: 1
gacagcgagg agacccctca tgcaccgcag acgcggagcg ctattcgccg gcgccgtggc      60
gatagccgcc ctgacgatcg ccgccgcgcc ggccaccgcc ggaccggccc tcgccccgcc     120
accggcccag gagacggcgg cccaggagat ccctgccggc atgctgcagg ccatgcagcg     180
tgatctcggc ctcaccgagc agcaggccga ggagcgcgtg gccaacgagt accaagcggg     240
ccagctggag ccacggctgc gggcgcaatt ggcggacacc ttcgccggtt cctggaccag     300
gggcgagacc gccgagctgg tcgtggccac caccgaccgc gagcagctac cggcgctgac     360
ggcggcgggc gtgcgggcca ccgtggccga gcacagcctg tccgagctcg aggccgtgaa     420
ggagacactg gacgaggccg ccgaggagca cgccacgacc gaggcgcccg tgtggtacgt     480
ggatgtcacg agcaacacgg tcatcgtgca cgcccaggac gtgacggccg ggcgcgactt     540
cgtctcggcc gcgggcgtgg accccgccgc ggtccacgtg ctgcgctcgg acgagcagcc     600
gcggccttac cacgacctgc ggggtgggga ggcgtactac atgggcagcg gagggcgctg     660
```

```
ctcggtcggc ttctccgttc gccgcggaac tcaggcgggc ttcgcgaccg cgggtcactg    720
cggccgggtc ggcaccacca cacggggctt caaccaggtg gcgcagggca ccttccaggg    780
ctccatcttc cccgggcgcg acatgggctg ggtcgcggtc aactccaact ggaacaccac    840
ccccttcgtc cgcggccagg ggggcgcgaa cgtgacggtg gcgggttcgc agcaggctcc    900
ggtcggctcc tcggtgtgcc gttccggctc caccaccggc tggcactgcg gcaccatcca    960
gcagcacaac acctcggtgc gctatccgga gggcaccatc agcggagtga ccaggacctc   1020
ggtgtgcgcc gaacccggtg actccggcgg cgcctacatc tccgggaacc aggcccaggg   1080
cgtgacctcc ggcggctcgg gcaactgccg caccggtggc accacctacc accagccgat   1140
caacccgctg ctggcacagt ggaacctgac cctcgtgacc acgggcaacg gcggcgaccc   1200
gggcgacccc ggtgacccgg cgacccgggt gagcccggc ggcagctggt ccgccgggac   1260
cagttacgcg gtcggcgacc gggtgaccta cggcggcgcg gagtaccgct gcctgcaggc   1320
ccacgtcgcc cagtccggct ggacgccccc gaacacgccc ccctctggc agcgcgtgtg   1380 acacgacca                                                           1389
```

<210> SEQ ID NO 2  
<211> LENGTH: 1362  
<212> TYPE: DNA  
<213> ORGANISM: Streptomyces sp.

<400> SEQUENCE: 2

```
atgcaccgca gacgcggagc gctattcgcc ggcgccgtgg cgatagccgc cctgacgatc     60
gccgccgcgc cggccaccgc cggaccggcc ctcgccccgc caccggccca ggagacggcg    120
gcccaggaga tccctgccgg catgctgcag gccatgcagc gtgatctcgg cctcaccgag    180
cagcaggccg aggagcgcgt ggccaacgag taccaagcgg ccagctggac gccacggctg    240
cgggcgcaat tggcggacac cttcgccggt tcctggacca ggggcgagac cgccgagctg    300
gtcgtggcca ccaccgaccg cgagcagcta ccggcgctga cggcggcggg cgtgcgggcc    360
accgtggcca agcacagcct gtccgagctc gaggccgtga aggagacact ggacgaggcc    420
gccgaggagc acgccacgac cgaggcgccc gtgtggtacg tggatgtcac gagcaacacg    480
gtcatcgtgc acgcccagga cgtgacggcc gggcgcgact tcgtctccgg cgcgggcgtg    540
gaccccgccg cggtccacgt gctgcgctcg gacgagcagc cgcggcctta ccacgacctg    600
cggggtgggg aggcgtacta catgggcagc ggagggcgct gctcggtcgg cttctccgtt    660
cgccgcggaa ctcaggcggg cttcgcgacc gcgggtcact gcggccgggt cggcaccacc    720
acacggggct tcaaccaggt ggcgcagggc accttccagg gctccatctt ccccgggcgc    780
gacatgggct gggtcgcggt caactccaac tggaacacca ccccccttcgt ccgcggccag    840 gggggcgcga acgtgacggt ggcgggttcg cagcaggctc cggtcggctc ctcggtgtgc    900
cgttccggct ccaccaccgg ctggcactgc ggcaccatcc agcagcacaa cacctcggtg    960
cgctatccgg agggcaccat cagcggagtg accaggacct cggtgtgcgc cgaacccggt   1020
gactccggcg gcgcctacat ctccgggaac caggcccagg gcgtgacctc cggcggctcg   1080
ggcaactgcc gcaccggtgg caccacctac caccagccga tcaacccgct gctggcacag   1140
tggaacctga ccctcgtgac cacgggcaac ggcggcgacc cgggcgaccc cggtgacccg   1200 gcgacccgg gtgagcccgg cggcagctgg tccgccggga ccagttacgc ggtcggcgac   1260
cgggtgacct acggcggcgc ggagtaccgc tgcctgcagg cccacgtcgc ccagtccggc   1320
```
tggacgcccc cgaacacgcc cgccctctgg cagcgcgtgt ga                    1362

<210> SEQ ID NO 3
<211> LENGTH: 453
<212> TYPE: PRT
<213> ORGANISM: Streptomyces sp.

<400> SEQUENCE: 3

Met His Arg Arg Gly Ala Leu Phe Ala Gly Ala Val Ala Ile Ala
1               5                   10                  15

Ala Leu Thr Ile Ala Ala Ala Pro Ala Thr Ala Gly Pro Ala Leu Ala
            20                  25                  30

Pro Pro Pro Ala Gln Glu Thr Ala Ala Gln Glu Ile Pro Ala Gly Met
        35                  40                  45

Leu Gln Ala Met Gln Arg Asp Leu Gly Leu Thr Gln Gln Ala Glu
    50                  55                  60

Glu Arg Val Ala Asn Glu Tyr Gln Ala Gly Gln Leu Glu Pro Arg Leu
65                  70                  75                  80

Arg Ala Gln Leu Ala Asp Thr Phe Ala Gly Ser Trp Thr Arg Gly Glu
                85                  90                  95

Thr Ala Glu Leu Val Val Ala Thr Thr Asp Arg Glu Gln Leu Pro Ala
            100                 105                 110

Leu Thr Ala Ala Gly Val Arg Ala Thr Val Ala Glu His Ser Leu Ser
        115                 120                 125

Glu Leu Glu Ala Val Lys Glu Thr Leu Asp Glu Ala Ala Glu Glu His
    130                 135                 140

Ala Thr Thr Glu Ala Pro Val Trp Tyr Val Asp Val Thr Ser Asn Thr
145                 150                 155                 160

Val Ile Val His Ala Gln Asp Val Thr Ala Gly Arg Asp Phe Val Ser
                165                 170                 175

Ala Ala Gly Val Asp Pro Ala Ala Val His Val Leu Arg Ser Asp Glu
            180                 185                 190

Gln Pro Arg Pro Tyr His Asp Leu Arg Gly Gly Glu Ala Tyr Tyr Met
        195                 200                 205

Gly Ser Gly Gly Arg Cys Ser Val Gly Phe Ser Val Arg Arg Gly Thr
    210                 215                 220

Gln Ala Gly Phe Ala Thr Ala Gly His Cys Gly Arg Val Gly Thr Thr
225                 230                 235                 240

Thr Arg Gly Phe Asn Gln Val Ala Gln Gly Thr Phe Gln Gly Ser Ile
                245                 250                 255

Phe Pro Gly Arg Asp Met Gly Trp Val Ala Val Asn Ser Asn Trp Asn
            260                 265                 270

Thr Thr Pro Phe Val Arg Gly Gln Gly Gly Ala Asn Val Thr Val Ala
        275                 280                 285

Gly Ser Gln Gln Ala Pro Val Gly Ser Ser Val Cys Arg Ser Gly Ser
    290                 295                 300

Thr Thr Gly Trp His Cys Gly Thr Ile Gln Gln His Asn Thr Ser Val
305                 310                 315                 320

Arg Tyr Pro Glu Gly Thr Ile Ser Gly Val Thr Arg Thr Ser Val Cys
                325                 330                 335

Ala Glu Pro Gly Asp Ser Gly Gly Ala Tyr Ile Ser Gly Asn Gln Ala
            340                 345                 350

Gln Gly Val Thr Ser Gly Gly Ser Gly Asn Cys Arg Thr Gly Gly Thr
        355                 360                 365

```
Thr Tyr His Gln Pro Ile Asn Pro Leu Leu Ala Gln Trp Asn Leu Thr
        370                 375                 380

Leu Val Thr Thr Gly Asn Gly Gly Asp Pro Gly Asp Pro Gly Asp Pro
385                 390                 395                 400

Gly Asp Pro Gly Glu Pro Gly Gly Ser Trp Ser Ala Gly Thr Ser Tyr
                405                 410                 415

Ala Val Gly Asp Arg Val Thr Tyr Gly Gly Ala Glu Tyr Arg Cys Leu
                420                 425                 430

Gln Ala His Val Ala Gln Ser Gly Trp Thr Pro Pro Asn Thr Pro Ala
            435                 440                 445

Leu Trp Gln Arg Val
    450
```

<210> SEQ ID NO 4
<211> LENGTH: 75
<212> TYPE: DNA
<213> ORGANISM: Streptomyces sp.

<400> SEQUENCE: 4
atgcaccgca acgcggagc gctattcgcc ggcgccgtgg cgatagccgc cctgacgatc    60
gccgccgcgc cggcc                                                   75

<210> SEQ ID NO 5
<211> LENGTH: 25
<212> TYPE: PRT
<213> ORGANISM: Streptomyces sp.

<400> SEQUENCE: 5

```
Met His Arg Arg Arg Gly Ala Leu Phe Ala Gly Ala Val Ala Ile Ala
1               5                   10                  15

Ala Leu Thr Ile Ala Ala Ala Pro Ala
            20                  25
```

<210> SEQ ID NO 6
<211> LENGTH: 516
<212> TYPE: DNA
<213> ORGANISM: Streptomyces sp.

<400> SEQUENCE: 6
accgccggac cggccctcgc cccgccaccg gcccaggaga cggcggccca ggagatccct    60
gccggcatgc tgcaggccat gcagcgtgat ctcggcctca ccgagcagca ggccgaggag   120
cgcgtggcca acgagtacca agcgggccag ctggagccac ggctgcgggc gcaattggcg   180
gacaccttcg ccggttcctg gaccaggggc gagaccgccg agctggtcgt ggccaccacc   240
gaccgcgagc agctaccggc gctgacgcg gcgggcgtgc gggccaccgt ggccgagcac   300
agcctgtccg agctcgaggc cgtgaaggag acactggacg aggccgccga ggagcacgcc   360
acgaccgagg cgcccgtgtg gtacgtggat gtcacgagca cacggtcat cgtgcacgcc   420 caggacgtga cggccgggcg cgacttcgtc tcggccgcgg gcgtggaccc cgccgcggtc   480
cacgtgctgc gctcggacga gcagccgcgg ccttac                            516

<210> SEQ ID NO 7
<211> LENGTH: 172
<212> TYPE: PRT
<213> ORGANISM: Streptomyces sp.

<400> SEQUENCE: 7

Thr Ala Gly Pro Ala Leu Ala Pro Pro Pro Ala Gln Glu Thr Ala Ala

```
                1               5                  10                  15
Gln Glu Ile Pro Ala Gly Met Leu Gln Ala Met Gln Arg Asp Leu Gly
                20                  25                  30

Leu Thr Glu Gln Gln Ala Glu Glu Arg Val Ala Asn Glu Tyr Gln Ala
            35                  40                  45

Gly Gln Leu Glu Pro Arg Leu Arg Ala Gln Leu Ala Asp Thr Phe Ala
        50                  55                  60

Gly Ser Trp Thr Arg Gly Glu Thr Ala Glu Leu Val Val Ala Thr Thr
65                  70                  75                  80

Asp Arg Glu Gln Leu Pro Ala Leu Thr Ala Ala Gly Val Arg Ala Thr
                85                  90                  95

Val Ala Glu His Ser Leu Ser Glu Leu Glu Ala Val Lys Glu Thr Leu
            100                 105                 110

Asp Glu Ala Ala Glu Glu His Ala Thr Thr Glu Ala Pro Val Trp Tyr
        115                 120                 125

Val Asp Val Thr Ser Asn Thr Val Ile Val His Ala Gln Asp Val Thr
    130                 135                 140

Ala Gly Arg Asp Phe Val Ser Ala Ala Gly Val Asp Pro Ala Ala Val
145                 150                 155                 160

His Val Leu Arg Ser Asp Glu Gln Pro Arg Pro Tyr
                165                 170

<210> SEQ ID NO 8
<211> LENGTH: 768
<212> TYPE: DNA
<213> ORGANISM: Streptomyces sp.

<400> SEQUENCE: 8
cacgacctgc ggggtgggga ggcgtactac atgggcagcg agggcgctg  ctcggtcggc      60
ttctccgttc gccgcggaac tcaggcgggc ttcgcgaccg cgggtcactg cggccgggtc     120
ggcaccacca cacggggctt caaccaggtg gcgcagggca ccttccaggg ctccatcttc     180
cccgggcgcg acatgggctg gtcgcggtc  aactccaact ggaacaccac ccccttcgtc     240
cgcggccagg ggggcgcgaa cgtgacggtg gcgggttcgc agcaggctcc ggtcggctcc     300
tcggtgtgcc gttccggctc caccaccggc tggcactgcg caccatcca  gcagcacaac     360
acctcggtgc gctatccgga gggcaccatc agcggagtga ccaggacctc ggtgtgcgcc     420
gaacccggtg actccggcgg cgcctacatc tccgggaacc aggcccaggg cgtgacctcc     480
ggcggctcgg gcaactgccg caccggtggc accacctacc accagccgat caacccgctg     540
ctggcacagt ggaacctgac cctcgtgacc acgggcaacg gcggcgaccc gggcgacccc     600
ggtgaccgg  cgaccgggg  tgagcccggc ggcagctggt ccgccgggac cagttacgcg     660
gtcggcgacc gggtgaccta cggcggcgcg gagtaccgct gcctgcaggc ccacgtcgcc     720
cagtccggct ggacgccccc gaacacgccc gccctctggc agcgcgtg                  768

<210> SEQ ID NO 9
<211> LENGTH: 256
<212> TYPE: PRT
<213> ORGANISM: Streptomyces sp.

<400> SEQUENCE: 9

His Asp Leu Arg Gly Gly Glu Ala Tyr Tyr Met Gly Ser Gly Gly Arg
1               5                   10                  15

Cys Ser Val Gly Phe Ser Val Arg Arg Gly Thr Gln Ala Gly Phe Ala
            20                  25                  30
```

```
Thr Ala Gly His Cys Gly Arg Val Gly Thr Thr Arg Gly Phe Asn
        35                  40                  45

Gln Val Ala Gln Gly Thr Phe Gln Gly Ser Ile Phe Pro Gly Arg Asp
    50                  55                  60

Met Gly Trp Val Ala Val Asn Ser Asn Trp Asn Thr Thr Pro Phe Val
65                  70                  75                  80

Arg Gly Gln Gly Gly Ala Asn Val Thr Val Ala Gly Ser Gln Gln Ala
                85                  90                  95

Pro Val Gly Ser Ser Val Cys Arg Ser Gly Ser Thr Thr Gly Trp His
            100                 105                 110

Cys Gly Thr Ile Gln Gln His Asn Thr Ser Val Arg Tyr Pro Glu Gly
        115                 120                 125

Thr Ile Ser Gly Val Thr Arg Thr Ser Val Cys Ala Glu Pro Gly Asp
    130                 135                 140

Ser Gly Gly Ala Tyr Ile Ser Gly Asn Gln Ala Gln Gly Val Thr Ser
145                 150                 155                 160

Gly Gly Ser Gly Asn Cys Arg Thr Gly Thr Thr Tyr His Gln Pro
                165                 170                 175

Ile Asn Pro Leu Leu Ala Gln Trp Asn Leu Thr Leu Val Thr Thr Gly
            180                 185                 190

Asn Gly Gly Asp Pro Gly Asp Pro Gly Asp Pro Gly Asp Pro Gly Glu
        195                 200                 205

Pro Gly Gly Ser Trp Ser Ala Gly Thr Ser Tyr Ala Val Gly Asp Arg
    210                 215                 220

Val Thr Tyr Gly Gly Ala Glu Tyr Arg Cys Leu Gln Ala His Val Ala
225                 230                 235                 240

Gln Ser Gly Trp Thr Pro Pro Asn Thr Pro Ala Leu Trp Gln Arg Val
                245                 250                 255

<210> SEQ ID NO 10
<211> LENGTH: 1287
<212> TYPE: DNA
<213> ORGANISM: Streptomyces sp.

<400> SEQUENCE: 10
accgccggac cggccctcgc cccgccaccg gcccaggaga cggcggccca ggagatccct      60
gccggcatgc tgcaggccat gcagcgtgat ctcggcctca ccgagcagca ggccgaggag     120
cgcgtggcca acgagtacca agcgggccag ctggagccac ggctgcgggc caattggcg      180 gacaccttcg ccggttcctg gaccaggggc gagaccgccg agctggtcgt ggccaccacc     240
gaccgcgagc agctaccggc gctgacggcg cgggcgtgc gggccaccgt ggccgagcac      300
agcctgtccg agctcgaggc cgtgaaggag acactggacg aggccgccga ggagcacgcc     360
acgaccgagg cgcccgtgtg gtacgtggat gtcacgagca cacggtcat cgtgcacgcc      420 caggacgtga cggccgggcg cgacttcgtc tcggccgcgg gcgtggaccc cgccgcggtc     480
cacgtgctgc gctcggacga gcagccgcgg cctaccacg acctgcgggg tggggaggcg      540
tactacatgg gcagcggagg gcgctgctcg gtcggcttct ccgttcgccg cggaactcag     600
gcgggcttcg cgaccgcggg tcactgcggc cgggtcggca ccaccacg gggcttcaac       660 caggtggcgc agggcaccctt ccagggctcc atcttccccg ggcgcgacat gggctgggtc    720
gcggtcaact ccaactggaa caccaccccc ttcgtccgcg ccagggggg gcgcgaacgtg    780 acggtggcgg gttcgcagca ggctccggtc ggctcctcgg tgtgccgttc cggctccacc    840
```

-continued

```
accggctggc actgcggcac catccagcag cacaacacct cggtgcgcta tccggagggc      900
accatcagcg gagtgaccag gacctcggtg tgcgccgaac ccgtgactc cggcggcgcc       960 tacatctccg ggaaccaggc ccagggcgtg acctccggcg gctcgggcaa ctgccgcacc     1020
ggtggcacca cctaccacca gccgatcaac ccgctgctgg cacagtggaa cctgaccctc     1080
gtgaccacgg caacggcgg cgaccccggc gaccccggtg acccgggcga cccgggtgag     1140
cccggcggca gctggtccgc cgggaccagt tacgcggtcg cgaccgggt gacctacggc      1200 ggcgcggagt accgctgcct gcaggcccac gtcgcccagt ccggctggac gccccgaac     1260 acgcccgccc tctggcagcg cgtgtga                                         1287
```

<210> SEQ ID NO 11
<211> LENGTH: 428
<212> TYPE: PRT
<213> ORGANISM: Streptomyces sp.

<400> SEQUENCE: 11

```
Thr Ala Gly Pro Ala Leu Ala Pro Pro Ala Gln Glu Thr Ala Ala
1               5                   10                  15

Gln Glu Ile Pro Ala Gly Met Leu Gln Ala Met Gln Arg Asp Leu Gly
            20                  25                  30

Leu Thr Glu Gln Gln Ala Glu Glu Arg Val Ala Asn Glu Tyr Gln Ala
        35                  40                  45

Gly Gln Leu Glu Pro Arg Leu Arg Ala Gln Leu Ala Asp Thr Phe Ala
    50                  55                  60

Gly Ser Trp Thr Arg Gly Glu Thr Ala Glu Leu Val Val Ala Thr Thr
65                  70                  75                  80

Asp Arg Glu Gln Leu Pro Ala Leu Thr Ala Ala Gly Val Arg Ala Thr
                85                  90                  95

Val Ala Glu His Ser Leu Ser Glu Leu Glu Ala Val Lys Glu Thr Leu
            100                 105                 110

Asp Glu Ala Ala Glu Glu His Ala Thr Thr Glu Ala Pro Val Trp Tyr
        115                 120                 125

Val Asp Val Thr Ser Asn Thr Val Ile Val His Ala Gln Asp Val Thr
    130                 135                 140

Ala Gly Arg Asp Phe Val Ser Ala Ala Gly Val Asp Pro Ala Ala Val
145                 150                 155                 160

His Val Leu Arg Ser Asp Glu Gln Pro Arg Pro Tyr His Asp Leu Arg
                165                 170                 175

Gly Gly Glu Ala Tyr Tyr Met Gly Ser Gly Arg Cys Ser Val Gly
            180                 185                 190

Phe Ser Val Arg Arg Gly Thr Gln Ala Gly Phe Ala Thr Ala Gly His
        195                 200                 205

Cys Gly Arg Val Gly Thr Thr Thr Arg Gly Phe Asn Gln Val Ala Gln
    210                 215                 220

Gly Thr Phe Gln Gly Ser Ile Phe Pro Gly Arg Asp Met Gly Trp Val
225                 230                 235                 240

Ala Val Asn Ser Asn Trp Asn Thr Thr Pro Phe Val Arg Gly Gln Gly
                245                 250                 255

Gly Ala Asn Val Thr Val Ala Gly Ser Gln Gln Ala Pro Val Gly Ser
            260                 265                 270

Ser Val Cys Arg Ser Gly Ser Thr Thr Gly Trp His Cys Gly Thr Ile
        275                 280                 285

Gln Gln His Asn Thr Ser Val Arg Tyr Pro Glu Gly Thr Ile Ser Gly
```

```
            290                 295                 300
Val Thr Arg Thr Ser Val Cys Ala Glu Pro Gly Asp Ser Gly Gly Ala
305                 310                 315                 320

Tyr Ile Ser Gly Asn Gln Ala Gln Gly Val Thr Ser Gly Gly Ser Gly
                325                 330                 335

Asn Cys Arg Thr Gly Gly Thr Thr Tyr His Gln Pro Ile Asn Pro Leu
            340                 345                 350

Leu Ala Gln Trp Asn Leu Thr Leu Val Thr Thr Gly Asn Gly Gly Asp
        355                 360                 365

Pro Gly Asp Pro Gly Asp Pro Gly Asp Pro Gly Glu Pro Gly Gly Ser
    370                 375                 380

Trp Ser Ala Gly Thr Ser Tyr Ala Val Gly Asp Arg Val Thr Tyr Gly
385                 390                 395                 400

Gly Ala Glu Tyr Arg Cys Leu Gln Ala His Val Ala Gln Ser Gly Trp
                405                 410                 415

Thr Pro Pro Asn Thr Pro Ala Leu Trp Gln Arg Val
            420                 425

<210> SEQ ID NO 12
<211> LENGTH: 434
<212> TYPE: DNA
<213> ORGANISM: Streptomyces sp.

<400> SEQUENCE: 12
gatcctggct caggacgaac gctggcggcg tgcttaacac atgcaagtcg aacgatgaag      60
ccgcttcggt ggtggattag tggcgaacgg gtgagtaaca cgtgggcaat ctgccctgca     120
ctctgggaca gcccgggaaa ctgggtctaa taccggata tgactgcttc gggcatccga     180
ggtggtggaa agctccggcg gtgcaggatg ggcccgcggc ctatcagctt gttggtgggg     240
tgatggccta ccaaggcgac gacgggtagc cggcctgaga gggcgaccgg ccacactggg     300
actgagacac ggcccagact cctacgggag gcagcagtgg ggaatattgc acaatgggcg     360
caagcctgat gcagcgacgc cgcgtgaggg atgacggcct cgggttgta aacctctttc      420 agcagggaag aagc                                                      434

<210> SEQ ID NO 13
<211> LENGTH: 18
<212> TYPE: DNA
<213> ORGANISM: Artificial
<220> FEATURE:
<223> OTHER INFORMATION: primer

<400> SEQUENCE: 13
cgctgytcvv tsggcttc                                                   18

<210> SEQ ID NO 14
<211> LENGTH: 24
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (10)..(12)
<223> OTHER INFORMATION: n is a, c, g, or t

<400> SEQUENCE: 14
gcagtygccn nngccgccgg asgt                                            24
```

<210> SEQ ID NO 15
<211> LENGTH: 463
<212> TYPE: DNA
<213> ORGANISM: Streptomyces sp.
<220> FEATURE:
<221> NAME/KEY: misc_feature
<222> LOCATION: (382)..(382)
<223> OTHER INFORMATION: n is a, c, g, or t
<220> FEATURE:
<221> NAME/KEY: misc_feature
<222> LOCATION: (420)..(420)
<223> OTHER INFORMATION: n is a, c, g, or t
<220> FEATURE:
<221> NAME/KEY: misc_feature
<222> LOCATION: (433)..(433)
<223> OTHER INFORMATION: n is a, c, g, or t
<220> FEATURE:
<221> NAME/KEY: misc_feature
<222> LOCATION: (436)..(436)
<223> OTHER INFORMATION: n is a, c, g, or t
<220> FEATURE:
<221> NAME/KEY: misc_feature
<222> LOCATION: (442)..(442)
<223> OTHER INFORMATION: n is a, c, g, or t
<220> FEATURE:
<221> NAME/KEY: misc_feature
<222> LOCATION: (449)..(449)
<223> OTHER INFORMATION: n is a, c, g, or t
<220> FEATURE:
<221> NAME/KEY: misc_feature
<222> LOCATION: (457)..(458)
<223> OTHER INFORMATION: n is a, c, g, or t

<400> SEQUENCE: 15

```
cgctgttcgc tgggcttccc cgttcgccgc ggaactcagg cgggcttcgc gaccgcgggt      60
cactgcggcc gggtcggcac caccacacgg ggcttcaacc aggtggcgca gggcaccttc     120
cagggctcca tcttccccgg gcgcgacatg ggctgggtcg cggtcaactc caactggaac     180
accaccccct tcgtccgcgg ccaggggggc gcgaacgtga cggtggcggg ttcgcagcag     240
gctccggtcg gctcctcggt gtgccgttcc ggctccacca ccggctggca ctgcggcacc     300
atccagcagc acaacacctc ggtgcgctat ccggagggcc accatcagcg gagtgaccac     360
gacctcggtg tgcgccgaac cntagtgact ccggcggcgc ctacatcttt gggaaccacn     420
gcccaggggc gtntangtcc cntccaccna aggccanntg cca                       463
```

<210> SEQ ID NO 16
<211> LENGTH: 113
<212> TYPE: PRT
<213> ORGANISM: Streptomyces sp.

<400> SEQUENCE: 16

```
Arg Cys Ser Leu Gly Phe Pro Val Arg Arg Gly Thr Gln Ala Gly Phe
1               5                   10                  15

Ala Thr Ala Gly His Cys Gly Arg Val Gly Thr Thr Arg Gly Phe
            20                  25                  30

Asn Gln Val Ala Gln Gly Thr Phe Gln Gly Ser Ile Phe Pro Gly Arg
        35                  40                  45

Asp Met Gly Trp Val Ala Val Asn Ser Asn Trp Asn Thr Thr Pro Phe
    50                  55                  60

Val Arg Gly Gln Gly Gly Ala Asn Val Thr Val Ala Gly Ser Gln Gln
65                  70                  75                  80

Ala Pro Val Gly Ser Ser Val Cys Arg Ser Gly Ser Thr Thr Gly Trp
                85                  90                  95

His Cys Gly Thr Ile Gln Gln His Asn Thr Ser Val Arg Tyr Pro Glu
            100                 105                 110
```

Gly

<210> SEQ ID NO 17
<211> LENGTH: 31
<212> TYPE: DNA
<213> ORGANISM: Artificial
<220> FEATURE:
<223> OTHER INFORMATION: primer

<400> SEQUENCE: 17
gtgccgttcc gcctccacca ccggctggca c                          31

<210> SEQ ID NO 18
<211> LENGTH: 30
<212> TYPE: DNA
<213> ORGANISM: Artificial
<220> FEATURE:
<223> OTHER INFORMATION: primer

<400> SEQUENCE: 18
gcgaagcccg cctgagttcc gcggcgaacg                            30

<210> SEQ ID NO 19
<211> LENGTH: 20
<212> TYPE: DNA
<213> ORGANISM: Artificial
<220> FEATURE:
<223> OTHER INFORMATION: primer

<400> SEQUENCE: 19
agagtttgat cctggctcag                                       20

<210> SEQ ID NO 20
<211> LENGTH: 8
<212> TYPE: DNA
<213> ORGANISM: Artificial
<220> FEATURE:
<223> OTHER INFORMATION: primer

<400> SEQUENCE: 20 ttgwhcgt                                                     8

<210> SEQ ID NO 21
<211> LENGTH: 5
<212> TYPE: DNA
<213> ORGANISM: Artificial
<220> FEATURE:
<223> OTHER INFORMATION: primer

<400> SEQUENCE: 21 gdsgg                                                        5

<210> SEQ ID NO 22
<211> LENGTH: 18
<212> TYPE: DNA
<213> ORGANISM: Artificial
<220> FEATURE:
<223> OTHER INFORMATION: primer

<400> SEQUENCE: 22
gwattaccgc ggckgctg                                         18

<210> SEQ ID NO 23
<211> LENGTH: 457
<212> TYPE: PRT

<213> ORGANISM: Streptomyces griseus

<400> SEQUENCE: 23

| | | | | | | | | | | | | | | |
|---|---|---|---|---|---|---|---|---|---|---|---|---|---|---|
| Val | Glu | Arg | Thr | Thr | Leu | Arg | Arg | Ala | Leu | Val | Ala | Gly | Thr | Ala |
| 1 | | | | 5 | | | | | 10 | | | | | 15 |
| Thr | Val | Ala | Val | Gly | Ala | Leu | Ala | Leu | Ala | Gly | Leu | Thr | Gly | Val | Ala |
| | | | 20 | | | | | 25 | | | | | 30 | | |
| Ser | Ala | Asp | Pro | Ala | Ala | Thr | Ala | Ala | Pro | Val | Ser | Ala | Asp | Ser |
| | | 35 | | | | | 40 | | | | | 45 | | |
| Leu | Ser | Pro | Gly | Met | Leu | Ala | Ala | Leu | Glu | Arg | Asp | Leu | Gly | Leu | Asp |
| | 50 | | | | | 55 | | | | | 60 | | | | |
| Glu | Asp | Ala | Ala | Arg | Ser | Arg | Ile | Ala | Asn | Glu | Tyr | Arg | Ala | Ala |
| 65 | | | | | 70 | | | | | 75 | | | | | 80 |
| Val | Ala | Ala | Gly | Leu | Glu | Lys | Ser | Leu | Gly | Ala | Arg | Tyr | Ala | Gly | Ala |
| | | | | 85 | | | | | 90 | | | | | 95 | |
| Arg | Val | Ser | Gly | Ala | Lys | Ala | Thr | Leu | Thr | Val | Ala | Thr | Thr | Asp | Ala |
| | | | 100 | | | | | 105 | | | | | 110 | | |
| Ser | Glu | Ala | Ala | Arg | Ile | Thr | Glu | Ala | Gly | Ala | Arg | Ala | Glu | Val | Val |
| | | 115 | | | | | 120 | | | | | 125 | | | |
| Gly | His | Ser | Leu | Asp | Arg | Phe | Glu | Gly | Val | Lys | Lys | Ser | Leu | Asp | Lys |
| | 130 | | | | | 135 | | | | | 140 | | | | |
| Ala | Ala | Leu | Asp | Lys | Ala | Pro | Lys | Asn | Val | Pro | Val | Trp | Tyr | Val | Asp |
| 145 | | | | | 150 | | | | | 155 | | | | | 160 |
| Val | Ala | Ala | Asn | Arg | Val | Val | Asn | Ala | Ala | Ser | Pro | Ala | Ala | Gly |
| | | | | 165 | | | | | 170 | | | | | 175 |
| Gln | Ala | Phe | Leu | Lys | Val | Ala | Gly | Val | Asp | Arg | Gly | Leu | Val | Thr | Val |
| | | | 180 | | | | | 185 | | | | | 190 | | |
| Ala | Arg | Ser | Ala | Glu | Gln | Pro | Arg | Ala | Leu | Ala | Asp | Ile | Arg | Gly | Gly |
| | 195 | | | | | 200 | | | | | 205 | | | | |
| Asp | Ala | Tyr | Tyr | Met | Asn | Gly | Ser | Gly | Arg | Cys | Ser | Val | Gly | Phe | Ser |
| 210 | | | | | 215 | | | | | 220 | | | | | |
| Val | Thr | Arg | Gly | Thr | Gln | Asn | Gly | Phe | Ala | Thr | Ala | Gly | His | Cys | Gly |
| 225 | | | | | 230 | | | | | 235 | | | | | 240 |
| Arg | Val | Gly | Thr | Thr | Thr | Asn | Gly | Val | Asn | Gln | Ala | Gln | Gly | Thr |
| | | | | 245 | | | | | 250 | | | | | 255 |
| Phe | Gln | Gly | Ser | Thr | Phe | Pro | Gly | Arg | Asp | Ile | Ala | Trp | Val | Ala | Thr |
| | | | 260 | | | | | 265 | | | | | 270 | | |
| Asn | Ala | Asn | Trp | Thr | Pro | Arg | Pro | Leu | Val | Asn | Gly | Tyr | Gly | Arg | Gly |
| | | 275 | | | | | 280 | | | | | 285 | | | |
| Asp | Val | Thr | Val | Ala | Gly | Ser | Thr | Ala | Ser | Val | Val | Gly | Ala | Ser | Val |
| | 290 | | | | | 295 | | | | | 300 | | | | |
| Cys | Arg | Ser | Gly | Ser | Thr | Thr | Gly | Trp | His | Cys | Gly | Thr | Ile | Gln | Gln |
| 305 | | | | | 310 | | | | | 315 | | | | | 320 |
| Leu | Asn | Thr | Ser | Val | Thr | Tyr | Pro | Glu | Gly | Thr | Ile | Ser | Gly | Val | Thr |
| | | | | 325 | | | | | 330 | | | | | 335 | |
| Arg | Thr | Ser | Val | Cys | Ala | Glu | Pro | Gly | Asp | Ser | Gly | Gly | Ser | Tyr | Ile |
| | | | 340 | | | | | 345 | | | | | 350 | | |
| Ser | Gly | Ser | Gln | Ala | Gln | Gly | Val | Thr | Ser | Gly | Gly | Ser | Gly | Asn | Cys |
| | | 355 | | | | | 360 | | | | | 365 | | | |
| Ser | Ser | Gly | Gly | Thr | Thr | Tyr | Phe | Gln | Pro | Ile | Asn | Pro | Leu | Leu | Gln |
| | 370 | | | | | 375 | | | | | 380 | | | | |
| Ala | Tyr | Gly | Leu | Thr | Leu | Val | Thr | Ser | Gly | Gly | Gly | Thr | Pro | Thr | Asp |
| 385 | | | | | 390 | | | | | 395 | | | | | 400 |

```
Pro Pro Thr Thr Pro Pro Thr Asp Ser Pro Gly Gly Thr Trp Ala Val
            405                 410                 415

Gly Thr Ala Tyr Ala Ala Gly Ala Thr Val Thr Tyr Gly Gly Ala Thr
            420                 425                 430

Tyr Arg Cys Leu Gln Ala His Thr Ala Gln Pro Gly Trp Thr Pro Ala
            435                 440                 445

Asp Val Pro Ala Leu Trp Gln Arg Val
    450                 455

<210> SEQ ID NO 24
<211> LENGTH: 255
<212> TYPE: PRT
<213> ORGANISM: Streptomyces griseus

<400> SEQUENCE: 24

Ala Asp Ile Arg Gly Gly Asp Ala Tyr Tyr Met Asn Gly Ser Gly Arg
1               5                   10                  15

Cys Ser Val Gly Phe Ser Val Thr Arg Gly Thr Gln Asn Gly Phe Ala
            20                  25                  30

Thr Ala Gly His Cys Gly Arg Val Gly Thr Thr Thr Asn Gly Val Asn
            35                  40                  45

Gln Gln Ala Gln Gly Thr Phe Gln Gly Ser Thr Phe Pro Gly Arg Asp
    50                  55                  60

Ile Ala Trp Val Ala Thr Asn Ala Asn Trp Thr Pro Arg Pro Leu Val
65                  70                  75                  80

Asn Gly Tyr Gly Arg Gly Asp Val Thr Val Ala Gly Ser Thr Ala Ser
                85                  90                  95

Val Val Gly Ala Ser Val Cys Arg Ser Gly Ser Thr Thr Gly Trp His
            100                 105                 110

Cys Gly Thr Ile Gln Gln Leu Asn Thr Ser Val Thr Tyr Pro Glu Gly
            115                 120                 125

Thr Ile Ser Gly Val Thr Arg Thr Ser Val Cys Ala Glu Pro Gly Asp
    130                 135                 140

Ser Gly Gly Ser Tyr Ile Ser Gly Ser Gln Ala Gln Gly Val Thr Ser
145                 150                 155                 160

Gly Gly Ser Gly Asn Cys Ser Ser Gly Gly Thr Thr Tyr Phe Gln Pro
                165                 170                 175

Ile Asn Pro Leu Leu Gln Ala Tyr Gly Leu Thr Leu Val Thr Ser Gly
            180                 185                 190

Gly Gly Thr Pro Thr Asp Pro Thr Pro Thr Pro Thr Asp Ser Pro
            195                 200                 205

Gly Gly Thr Trp Ala Val Gly Thr Ala Tyr Ala Ala Gly Ala Thr Val
            210                 215                 220

Thr Tyr Gly Gly Ala Thr Tyr Arg Cys Leu Gln Ala His Thr Ala Gln
225                 230                 235                 240

Pro Gly Trp Thr Pro Ala Asp Val Pro Ala Leu Trp Gln Arg Val
                245                 250                 255

<210> SEQ ID NO 25
<211> LENGTH: 495
<212> TYPE: PRT
<213> ORGANISM: Cellulomonas sp.

<400> SEQUENCE: 25

Met Thr Pro Arg Thr Val Thr Arg Ala Leu Ala Val Ala Thr Ala Ala
1               5                   10                  15
```

```
Ala Thr Leu Leu Ala Gly Gly Met Ala Ala Gln Ala Asn Glu Pro Ala
             20                  25                  30

Pro Pro Gly Ser Ala Ser Ala Pro Pro Arg Leu Ala Glu Lys Leu Asp
             35                  40                  45

Pro Asp Leu Leu Glu Ala Met Glu Arg Asp Leu Gly Leu Asp Ala Glu
 50                  55                  60

Glu Ala Ala Ala Thr Leu Ala Phe Gln His Asp Ala Ala Glu Thr Gly
 65                  70                  75                  80

Glu Ala Leu Ala Glu Glu Leu Asp Glu Asp Phe Ala Gly Thr Trp Val
                 85                  90                  95

Glu Asp Asp Val Leu Tyr Val Ala Thr Thr Asp Glu Asp Ala Val Glu
            100                 105                 110

Glu Val Glu Gly Glu Gly Ala Thr Ala Val Thr Val Glu His Ser Leu
            115                 120                 125

Ala Asp Leu Glu Ala Trp Lys Thr Val Leu Asp Ala Ala Leu Glu Gly
130                 135                 140

His Asp Asp Val Pro Thr Trp Tyr Val Asp Val Pro Thr Asn Ser Val
145                 150                 155                 160

Val Val Ala Val Lys Ala Gly Ala Gln Asp Val Ala Ala Gly Leu Val
                165                 170                 175

Glu Gly Ala Asp Val Pro Ser Asp Ala Val Thr Phe Val Glu Thr Asp
            180                 185                 190

Glu Thr Pro Arg Thr Met Phe Asp Val Ile Gly Gly Asn Ala Tyr Thr
            195                 200                 205

Ile Gly Gly Arg Ser Arg Cys Ser Ile Gly Phe Ala Val Asn Gly Gly
            210                 215                 220

Phe Ile Thr Ala Gly His Cys Gly Arg Thr Gly Ala Thr Thr Ala Asn
225                 230                 235                 240

Pro Thr Gly Thr Phe Ala Gly Ser Ser Phe Pro Gly Asn Asp Tyr Ala
                245                 250                 255

Phe Val Arg Thr Gly Ala Gly Val Asn Leu Leu Ala Gln Val Asn Asn
            260                 265                 270

Tyr Ser Gly Gly Arg Val Gln Val Ala Gly His Thr Ala Ala Pro Val
            275                 280                 285

Gly Ser Ala Val Cys Arg Ser Gly Ser Thr Thr Gly Trp His Cys Gly
            290                 295                 300

Thr Ile Thr Ala Leu Asn Ser Ser Val Thr Tyr Pro Glu Gly Thr Val
305                 310                 315                 320

Arg Gly Leu Ile Arg Thr Thr Val Cys Ala Glu Pro Gly Asp Ser Gly
                325                 330                 335

Gly Ser Leu Leu Ala Gly Asn Gln Ala Gln Gly Val Thr Ser Gly Gly
            340                 345                 350

Ser Gly Asn Cys Arg Thr Gly Gly Thr Thr Phe Phe Gln Pro Val Asn
            355                 360                 365

Pro Ile Leu Gln Ala Tyr Gly Leu Arg Met Ile Thr Thr Asp Ser Gly
 370                 375                 380

Ser Ser Pro Ala Pro Ala Pro Thr Ser Cys Thr Gly Tyr Ala Arg Thr
385                 390                 395                 400

Phe Thr Gly Thr Leu Ala Ala Gly Arg Ala Ala Gln Pro Asn Gly
                405                 410                 415

Ser Tyr Val Gln Val Asn Arg Ser Gly Thr His Ser Val Cys Leu Asn
            420                 425                 430

Gly Pro Ser Gly Ala Asp Phe Asp Leu Tyr Val Gln Arg Trp Asn Gly
```

```
                435                 440                 445
Ser Ser Trp Val Thr Val Ala Gln Ser Thr Ser Pro Gly Ser Asn Glu
    450                 455                 460

Thr Ile Thr Tyr Arg Gly Asn Ala Gly Tyr Tyr Arg Tyr Val Val Asn
465                 470                 475                 480

Ala Ala Ser Gly Ser Gly Ala Tyr Thr Met Gly Leu Thr Leu Pro
                485                 490                 495

<210> SEQ ID NO 26
<211> LENGTH: 189
<212> TYPE: PRT
<213> ORGANISM: Cellulomonas sp.

<400> SEQUENCE: 26

Phe Asp Val Ile Gly Gly Asn Ala Tyr Thr Ile Gly Gly Arg Ser Arg
1               5                   10                  15

Cys Ser Ile Gly Phe Ala Val Asn Gly Gly Phe Ile Thr Ala Gly His
            20                  25                  30

Cys Gly Arg Thr Gly Ala Thr Thr Ala Asn Pro Thr Gly Thr Phe Ala
        35                  40                  45

Gly Ser Ser Phe Pro Gly Asn Asp Tyr Ala Phe Val Arg Thr Gly Ala
    50                  55                  60

Gly Val Asn Leu Leu Ala Gln Val Asn Asn Tyr Ser Gly Gly Arg Val
65                  70                  75                  80

Gln Val Ala Gly His Thr Ala Ala Pro Val Gly Ser Ala Val Cys Arg
                85                  90                  95

Ser Gly Ser Thr Thr Gly Trp His Cys Gly Thr Ile Thr Ala Leu Asn
            100                 105                 110

Ser Ser Val Thr Tyr Pro Glu Gly Thr Val Arg Gly Leu Ile Arg Thr
        115                 120                 125

Thr Val Cys Ala Glu Pro Gly Asp Ser Gly Gly Ser Leu Leu Ala Gly
    130                 135                 140

Asn Gln Ala Gln Gly Val Thr Ser Gly Gly Ser Gly Asn Cys Arg Thr
145                 150                 155                 160

Gly Gly Thr Thr Phe Phe Gln Pro Val Asn Pro Ile Leu Gln Ala Tyr
                165                 170                 175

Gly Leu Arg Met Ile Thr Thr Asp Ser Gly Ser Ser Pro
            180                 185

<210> SEQ ID NO 27
<211> LENGTH: 29
<212> TYPE: DNA
<213> ORGANISM: Artificial
<220> FEATURE:
<223> OTHER INFORMATION: primer

<400> SEQUENCE: 27
gtggtggcca cgaccagctc ggcggtctc                                    29

<210> SEQ ID NO 28
<211> LENGTH: 25
<212> TYPE: DNA
<213> ORGANISM: Artificial
<220> FEATURE:
<223> OTHER INFORMATION: primer

<400> SEQUENCE: 28
tggtccagga accggcgaag gtgtc                                        25
```

```
<210> SEQ ID NO 29
<211> LENGTH: 61
<212> TYPE: DNA
<213> ORGANISM: Artificial
<220> FEATURE:
<223> OTHER INFORMATION: primer

<400> SEQUENCE: 29
gactgcgcta gccggccccc cggcacaggc caccgccgga ccggccctcg ccccgccacc        60
g                                                                       61

<210> SEQ ID NO 30
<211> LENGTH: 49
<212> TYPE: DNA
<213> ORGANISM: Artificial
<220> FEATURE:
<223> OTHER INFORMATION: primer

<400> SEQUENCE: 30
gctcgcggat ccccattgtc acacgcgctg ccagagggcg ggcgtgttc                    49
```